(12) United States Patent
Arculus-Meanwell et al.

(10) Patent No.: US 9,925,265 B2
(45) Date of Patent: *Mar. 27, 2018

(54) METHODS OF TREATING OR PREVENTING STENT THROMBOSIS

(75) Inventors: Clive Arthur Arculus-Meanwell, Bernardsville, NJ (US); Simona Skerjanec, Basel (CH)

(73) Assignee: Chiesi Farmaceutici S.p.A., Parma (IT)

( * ) Notice: Subject to any disclaimer, the term of this patent is extended or adjusted under 35 U.S.C. 154(b) by 49 days.

This patent is subject to a terminal disclaimer.

(21) Appl. No.: 12/943,717

(22) Filed: Nov. 10, 2010

(65) Prior Publication Data

US 2011/0112030 A1 May 12, 2011

Related U.S. Application Data

(60) Provisional application No. 61/260,361, filed on Nov. 11, 2009.

(51) Int. Cl.
| | | |
|---|---|---|
| A61K 31/7076 | (2006.01) | |
| A61K 38/10 | (2006.01) | |
| A61K 38/58 | (2006.01) | |
| A61K 47/26 | (2006.01) | |
| A61K 9/00 | (2006.01) | |
| A61K 9/19 | (2006.01) | |
| A61K 45/06 | (2006.01) | |
| A61K 47/02 | (2006.01) | |

(52) U.S. Cl.
CPC .......... *A61K 47/26* (2013.01); *A61K 9/0019* (2013.01); *A61K 9/19* (2013.01); *A61K 31/7076* (2013.01); *A61K 38/10* (2013.01); *A61K 38/58* (2013.01); *A61K 45/06* (2013.01); *A61K 47/02* (2013.01)

(58) Field of Classification Search
CPC .... A61K 31/52; A61K 31/7076; A61K 38/10; A61K 38/58; C07D 473/24; C07H 19/20; C07K 7/08

See application file for complete search history.

(56) References Cited

U.S. PATENT DOCUMENTS

| | | |
|---|---|---|
| 4,529,596 A | 7/1985 | Aubert et al. |
| 5,196,404 A | 3/1993 | Maraganore et al. |
| 5,288,726 A | 2/1994 | Koike |
| 5,721,219 A | 2/1998 | Ingall et al. |
| 5,955,447 A | 7/1999 | Ingall et al. |
| 6,114,313 A | 9/2000 | Bland et al. |
| 6,130,208 A | 10/2000 | Broadhead |
| 6,693,115 B2 | 2/2004 | Asai et al. |
| 6,861,424 B2 | 3/2005 | Bryant |
| 7,026,323 B2 | 4/2006 | Bryant et al. |
| 8,680,052 B1* | 3/2014 | Arculus-Meanwell ............ A61K 9/0019 514/14.7 |
| 8,871,736 B2 | 3/2014 | Arculus-Meanwell et al. |
| 8,716,261 B2 | 5/2014 | Ruderman Chen et al. |
| 8,759,316 B2* | 6/2014 | Chen ................. A61K 31/7076 514/327 |
| 9,427,448 B2* | 8/2016 | Arculus-Meanwell ............ A61K 9/0019 |
| 2002/0123791 A1* | 9/2002 | Harrison ................. A61F 2/91 623/1.15 |
| 2006/0270607 A1 | 11/2006 | Dixon et al. |
| 2007/0082840 A1* | 4/2007 | Porter et al. ...................... 514/9 |
| 2007/0254324 A1 | 11/2007 | Rechner |
| 2007/0276460 A1* | 11/2007 | Davis ...................... A61F 2/856 623/1.2 |
| 2009/0043380 A1* | 2/2009 | Blaha ...................... A61L 31/10 623/1.46 |
| 2009/0088834 A1* | 4/2009 | Wang ...................... A61L 31/148 623/1.15 |
| 2009/0247465 A1 | 10/2009 | Baldo et al. |
| 2009/0304770 A1* | 12/2009 | Lewis ................... C08F 220/18 424/423 |
| 2010/0120718 A1* | 5/2010 | Perzborn ............ A61K 31/4365 514/81 |
| 2011/0112030 A1 | 5/2011 | Arculus-Meanwell et al. |

(Continued)

FOREIGN PATENT DOCUMENTS

| | | |
|---|---|---|
| EP | 2 105 137 A1 | 9/2009 |
| WO | 199418216 A1 | 2/1994 |

(Continued)

OTHER PUBLICATIONS

Steinhubl et al. Thrombosis Research 2008 121, 527-534.*
Schneider et al. (Coronary Artery Disease Mar. 2009, vol. 20, No. 2, pp. 175-178).*
Steinhubl et al. (Thrombosis Research 2008, 121, pp. 527-534).*
Lehman and Chew (Vascular Heart and Risk Management 2006:2 (4) 357-363).*
Feldman et al. Impact of bivalirudin on outcomes after percutaneous coronary revascularization with drug-eluting stents. American Heart Journal. Oct. 2007. vol. 154, No. 4, pp. 695-701.*
Lincoff et al. Bivalirudin with planned or provisional abciximab versus low-dose heparin . . . American Heart Journal. May 2002. vol. 143, No. 5, pp. 847-853.*
Abbracchio MP, et al., International union of pharmacology LVIII: update on the P2Y G protein-coupled nucleotide receptors: from molecular mechanisms and pathophysiology to therapy, Pharmacol Rev, 2006, pp. 281-341,vol. 58, No. 3.

(Continued)

*Primary Examiner* — Jeffrey E. Russel
(74) *Attorney, Agent, or Firm* — Beck & Thomas, P.C.

(57) ABSTRACT

The present invention is directed to the following: methods of treating or preventing stent thrombosis using pharmaceutical compositions comprising cangrelor and optionally bivalirudin; methods of reducing mortality in a subject undergoing stent implantation using pharmaceutical compositions comprising cangrelor and optionally bivalirudin; medicaments comprising cangrelor and optionally bivalirudin useful for treating or preventing stent thrombosis, or useful for reducing mortality in a subject undergoing stent implantation; pharmaceutical compositions comprising cangrelor and bivalirudin; and methods of preparing a medicament comprising cangrelor and optionally bivalirudin useful for treating or preventing stent thrombosis, or useful for reducing mortality in a subject undergoing stent implantation.

27 Claims, 9 Drawing Sheets

(56) References Cited

U.S. PATENT DOCUMENTS

| | | | |
|---|---|---|---|
| 2011/0178594 A1* | 7/2011 | Kim, II | A61L 27/26 623/1.44 |
| 2011/0276123 A1* | 11/2011 | Davies | A61F 2/88 623/1.15 |
| 2011/0288043 A1 | 11/2011 | Chen et al. | |
| 2012/0141468 A1 | 6/2012 | Chen et al. | |
| 2012/0184504 A1* | 7/2012 | Strony et al. | 514/47 |
| 2013/0040898 A1 | 2/2013 | Johansson et al. | |
| 2013/0190265 A1 | 7/2013 | Arculus-Meanwell et al. | |
| 2013/0303477 A1 | 11/2013 | Ruderman Chen et al. | |
| 2013/0303478 A1 | 11/2013 | Ruderman Chen et al. | |
| 2013/0316968 A1 | 11/2013 | Ruderman Chen et al. | |
| 2013/0324492 A1 | 12/2013 | Ruderman Chen et al. | |
| 2014/0107032 A1 | 4/2014 | Arculus-Meanwell et al. | |
| 2015/0038449 A1 | 2/2015 | Ruderman Chen et al. | |

FOREIGN PATENT DOCUMENTS

| | | | |
|---|---|---|---|
| WO | | 200139781 A1 | 6/2001 |
| WO | | 2005097814 A1 | 10/2005 |
| WO | | 2005097814 A2 | 10/2005 |
| WO | | 2006119507 A2 | 11/2006 |
| WO | | 2007024472 A2 | 1/2007 |
| WO | WO 2008/052671 A2 * | | 5/2008 |
| WO | | 2008127682 A2 | 8/2008 |
| WO | | 2009140092 A1 | 11/2009 |
| WO | | 2011060066 A2 | 5/2011 |
| WO | | 2011134478 A2 | 11/2011 |
| WO | WO-2013-025476 | | 2/2013 |

OTHER PUBLICATIONS

Aleil B, et al., Flow cytometric analysis of intraplatelet VASP phosphorylation for the detection of clopidogrel resistance in patients with ischemic cardiovascular diseases, J Thromb Haemost, 2005, pp. 85-92.

Angiolillo DJ, ADP Receptor Antagonism. What's in the Pipeline?, Am J Cardiovasc Drugs, 2007, pp. 423-432. vol. 7 No. 6.

Angiolillo DJ, et al., Pharmacology of emerging novel platelet inhibitors, Am Heart J, 2008, pp. S10-S15, vol. 156, No. 2, Supp. 1.

Angiolillo DJ, et al., Clinical overview of promising nonthienopyridine antiplatelet agents, Am Heart J, 2008, pp. S23-S28, vol. 156, No. 2, Supp 1.

Becker RC, Platelet surface physiology and its importance in pharmacotherapy design and development: The adenosine diphosphate receptor antagonists, J Thromb Thrombolysis, 2000, pp. 35-53.

Boeynaems JM, Van Giezen H, Savi P, Herbert JM, P2Y receptor antagonists in thrombosis, Curr Opin Investig Drugs, 2005, pp. 275-282, vol. 6, No. 3.

Cattaneo M, Platelet P2 receptors: old and new targets for antithrombotic drugs, Expert Rev Cardiovasc Ther, 2007, pp. 45-55, vol. 5, No. 1.

Chattaraj SC, Cangrelor astra Zeneca, Curr Opin Investig Drugs, 2001, pp. 250-255, vol. 2, No. 2.

Christensen K, Larsson R, Emanuelsson H, et al., Effects on blood compatibility in vitro by combining a direct P2Y12 receptor inhibitor and heparin coating of stents, Platelets, 2006, pp. 318-327, vol. 17, No. 5.

Cohen M, Diez J, Levine GN, et al., Pharmacoinvasive management of acute coronary syndrome: incorporating the 2007 ACC/AHA Guidelines. The CATH (Cardiac Catherization and Antithrombotic Therapy in the Hospital) Clinical Consensus Panel Report-III, J Invasive Cardiology, 2007, pp. 525-540, vol. 19, No. 12.

Dalal AR, D'Souza S, Shulman MS, Brief review: coronary drug-eluting stents and anesthesia, Can J Anaest, 2006, pp. 1230-1243, vol. 53, No. 12.

Diaz-Ricart M, Cangrelor tetrasodium, Drugs of the Future, 2008, pp. 101-110, vol. 33, No. 2.

Ding Z, Kim S, Kunapuli SP, Identification of a potent inverse agonist at a constitutively active mutant of human P2Y12 receptor, Mol Pharmacol, 2005, pp. 338-345, vol. 69, No. 1.

Dovlatova NL, Jakubowski JA, Sugidachi A, et al., The reversible P2Y12 antagonist cangrelor influences the ability of the active metabolites of clopidogrel and prasugrel to produce irreversible inhibition of platelet function, J Thromb Haemost, 2008, pp. 1153-1159, vol. 6.

Dovlatova N, Wijeyeratne YD, Fox SC, et al., Detection of P2Y(14) protein in platelets and investigation of the role of P2Y(14) in platelet function in comparison with the EP(3) receptor, Thromb Haemost, 2008, pp. 261-270, vol. 100.

Fugate SE, Cudd LA, Cangrelor for treatment of coronary thrombosis, Ann Pharmacother, 2006, pp. 925-930, vol. 40.

Gitt AK, Betriu A., Antiplatelet therapy in acute coronary syndromes, Eur Heart J, 2008, pp. A4-A12, 10 Supp. A.

Greenbaum AB, Ohman EM, Gibson CM, et al., Preliminary experience with intravenous P2Y12 platelet receptor inhibition as an adjunct to reduced-dose alteplase during acute myocardial infarction: Results of the Safety, Tolerability and Effect on Patency in Acute Myocardial Infarction (STEP-AMI) angiographic trial, Am Heart J, 2007 pp. 702-709, vol. 54, No. 4.

Greenbaum AB, Grines CL, Bittl JA, et al., Initial experience with an intravenous P2Y12 platelet receptor antagonist in patients undergoing percutaneous coronary intervention: Results from a 2-part, phase II, multicenter, randomized, placebo- and active-controlled trial, Am Heart J, 2006, pp. 689.e1-689.e10.

Greenbaum AB, Ohman EM, Gibson MS, et al., Intravenous adenosine diphosphate P2T platelet receptor antagonism as an adjunct to fibrinolysis for acute myocardial infarction, JACC, 2002, Abstract 1002-45, vol. 39, Issue 5, Supp. A.

Huang J, Driscoll EM, Gonzales ML, Prevention of arterial thrombosis by intravenously administered platelet P2T receptor antagonist AR-C66931MX in a canine model, J Pharmacol Exp Ther, 2000, pp. 492-499, vol. 295, No. 2.

Humphries RG, Pharmacology of AR-C69931MX and related compounds: from pharmacological tools to clinical trials, Haematologica, 2000, pp. 66-72, 85(the Platelet ADP Receptors Supp.).

Ingall AH, P2T receptor antagonists: novel inhibitors of platelet aggregation, Arch Pharm, 1999, pp. 11-12, Supp. 1.

Ingall AH, Dixon J, Bailey A, et al., Antagonists of the platelet P2T receptor: a novel approach to antithrombotic therapy, J Med Chem, 1999, pp. 213-220, vol. 42.

Jacobsson F, Swahn E, Wallentin L, et al., Safety profile and tolerability of intravenous AR C69931MX, a new antiplatelet drug, in unstable angina pectoris and non Q wave myocardial infarction, Clin Ther, 2002, pp. 752-765, vol. 24, No. 5.

Jacobsson F, Dellborg M, Swahn E, et al., JACC, 2000, p. 343, vol. 35, Issue, 2, Supp. A.

Jarvis GE, Nassim MA, Humphries RG, et al., The P2T antagonist AR C69931MX is a more effective inhibitor of ADP induced platelet aggregation than clopidogrel, Blood, 1999, p. 194, (10 Supp. pt. 1):22a.

Jarvis GE, Nassim MA, Humphries RG, et al., Superior inhibition of ADP induced human platelet aggregation by AR C69931MX than clopidogrel, Drug Dev Res, 2000, p. 90. vol. 50, No. 1.

Judge HM, Buckland RJ, Holgate CE, et al, Glycoprotein IIb/IIIa and P2Y12 receptor antagonists yield additive inhibition of platelet aggregation, granule secretion, soluble CD40L release and procoagulant responses, Platelets, 2005, pp. 398-407, vol. 16, No. 7.

Kandzari DE, Evolving antithrombotic treatment strategies for acute ST-elevation myocardial infarction, Rev Cardiovasc Med, 2006, pp. S29-S37, vol. 7, Supp. 4.

Kuijpers MJ, Nieuwenhuys CM, Feijge MA, et al., Regulation of tissue factor-induced coagulation and platelet aggregation in flowing whole blood, Thromb Haemost, 2005; 93, pp. 97-105.

Kunapuli SP, Ding Z, Dorsam RT, et al., ADP receptors target for developing antithrombotic agents, Curr Pharm Des, 2003, vol. 9, pp. 2303-2316.

Leon C, Alex M, Klocke A, et al., Platelet ADP receptors contribute to the initiation of intravascular coagulation, Blood, 2004, pp. 594-600, vol. 103, No. 2.

(56) References Cited

OTHER PUBLICATIONS

Mazzucato M, Cozzi MR, Pradella P, et al., Crucial role of the ADP receptor P2Y1 in platelet adhesion and signaling under high flow, Blood, 2002, p. 100, 11.
Michelson AD, P2Y12 Antagonism. Promises and challenges, Arterioscler Thromb Vasc Biol, 2008, pp. S33-S38.
Murugappan S, Kunapuli S, The role of ADP receptors in platelet function, Front Biosci, 2006, pp. 1977-1986, vol. 11.
Nassim MA, Sanderson JB, Clarke C, et al., Investigation of the novel P2T receptor antagonist AR C69931MX on ex vivo adenosine diphosphate induced platelet aggregation and bleeding time in healthy volunteers, JACC, 1999, p. 33, vol. 33 (Supp A).
Niitsu Y, Jakubowski JA, Sugidachi A, et al., Pharmacology of CS-747 (Prasugrel, LY640315), a novel, potent antiplatelet agent with in vivo P2Y12 receptor antagonist activity, Semin Thromb Hemost, 2005, pp. 184-194, vol. 31, No. 2.
Nogard NB, Abu-Fadel M, Future prospects in anti-platelet therapy: A review of potential P2Y12 and thrombin receptor antagonists, Recent Patents Cardiovasc Drug Discovery, 2008, pp. 194-200, vol. 3.
Nurden AT, Nurden P, Advantages of fast-acting ADP receptor blockade in ischemic heart disease (Editorial to K. Wang article p. 357), Arterioscler Thromb Vasc Biol, 2003, pp. 158-159.
Nylander S, Mattsson C, Lindahl TL, Characterisation of species differences in the platelet ADP and thrombin response, Thromb Res, 2003, pp. 65-73, vol. 111.
Park SJ, Lee SW, Optimal management of platelet function after coronary stenting, Curr Treat Options Cardiovasc Med, 2007, pp. 37-45.
Parravicini C, Ranghino G, Abbracchio MP, et al., GPR17: Molecular modeling and dynamics studies of the 3-D structure and purinergic ligand binding features in comparison with P2Y receptors, BMC Bioinformatics, 2008, pp. 1-19, vol. 9, No. 263.
Penz SM, Reininger AJ, Toth O, et al., Glycoprotein Ibα inhibition and ADP receptor antagonists, but not aspirin, reduce platelet thrombus formation in flowing blood exposed to atherosclerotic plaques, Thromb Haemost, 2007, pp. 435-443, vol. 97.
Price MJ, New antiplatelet therapies in development, Am J Health-Syst Pharm, 2008, pp. S11-S15, vol. 65.
Raju NC, Eikelboom JW, Hirsh J, Platelet ADP-receptor antagonists for cardiovascular disease: past, present and future, Nat Clin Pract Cardiovasc Med, 2008, pp. 766-780, vol. 5, No. 12.
Rich J, Wiviott SD, New antiplatelet therapies for acute coronary syndromes, Curr Cardiol Rep, 2007, pp. 303-311, vol. 9.
Steinhubl SR, OH JJ, Oestreich JH, et al., Transitioning patients from cangrelor to clopidogrel: Pharmacodynamic evidence of a competitive effect, Thromb Res, 2007, pp. 527-534, vol. 121.
Steinhubl S, Roe MT, Optimizing platelet P2Y12 inhibition for patients undergoing PCI, Cardiovasc Drug Rev, 2007, pp. 188-203, vol. 25, No. 2.
Storey RF, Oldroyd KG, Wilcox RG, First clinical study of the novel platelet ADP receptor (P2T) antagonist AR-C69931MX, assessing safety, tolerability and activity in patients with acute coronary syndromes, Circulation, 1999, p. 1-170 vol. 100, No. 18.
Storey RF, Sanderson HM, White AE, et al., The central role of the P(2T) receptor in amplification of human platelet activation, aggregation, secretion and procoagulant activity, Br J Haematol, 2000, pp. 925-934, vol. 110.
Storey RF, Cameron KE, Pascoe JS, et al., Potential therapeutic effect of the novel platelet adenosine diphosphate receptor (P2T) antagonist, AR C69931MX, as assessed by in vitro studies in human whole blood. A possible adjunct to aspirin therapy?, Eur Heart J, 1998, p. 493, 19(SUPP):54.
Storey RF, Oldroyd KG, Wilcox RG, Open multicentre study of the P2T receptor antagonist AR-C69931MX assessing safety, tolerability and activity in patients with acute coronary syndromes, Thromb Haemost, 2001, pp. 401-407, vol. 85.
Storey RF, Variability of response to antiplatelet therapy, Eur Heart J, 2008, pp. A21-A27, 10(Supp A).
Storey RF, New developments in antiplatelet therapy, Eur Heart J, 2008, pp. D30-D37,10 (Supp D).
Storey RF, Clinical experience with antithrombotic drugs acting on purine receptor pathways, Drug Dev Res, 2001, pp. 202-212, vol. 52.
Storey RF, The P2Y12 receptor as a therapeutic target in cardiovascular disease, Platelets, 2001, pp. 197-209, vol. 12.
Storey RF, Wilcox RG, Heptinstall S, Comparison of the pharmacodynamic effects of the platelet ADP receptor antagonists clopidogrel and AR-C69931MX in patients with ischaemic heart disease, Platelets, 2002, pp. 407-413, vol. 13.
Storey RF, Judge HM, Wilcox RG, et al., Inhibition of ADP-induced p-selection expression and platelet-leukocyte conjugate formation by clopidogrel and the P2Y12 receptor antagonist AR-C69931MX but not aspirin, Thromb Res, 2002, pp. 488-494, vol. 88.
Harrington RA, Stone GW, McNulty S, et al., Platelet inhibition with cangrelor in patients undergoing PCI, N Engl J Med, 2009, pp. 2318-2319, vol. 361.
Iyu D, Glenn JR, White AE, et al., Mode of action of P2Y12 antagonists as inhibitors of platelet function, Thromb Haemost, 2011, pp. 96-105, vol. 105.
Leonardi S, Stebbins A, Lopes RD, et al., Maintenance therapy with thienopyridines may reduce enzymatic infarct size in patients with acute coronary syndrome undergoing PCI: Insights from the Champion PCI trial, AHA Chicago, IL, 2010.
Testa L, Biondi Zoccai GG, Valgimigli M, et al., Current concepts on antiplatelet therapy: focus on the novel thienopyridine and non-thienopyridine agents, Adv Hematol, 2010, pp. 1-7, vol. 2010.
Ueno M, Ferreiro JL, Angiolillo DJ, Update on the clinical development of cangrelor, Expert Rev Cardiovasc, 2010, pp. 1069-1077, vol. 8L.
Ahrens I, Bode C, Novel antiplatelet therapies following percutaneous coronary interventions, Curr Opin Investig Drugs, 2009, pp. 902-911, vol. 10.
Akers WS, OH JJ, Oestreich JH, et al., Pharmacokinetics and pharmacodynamics of a bolus and infusion of cangrelor: a direct, parenteral P2Y12 receptor antagonist, J Clin Pharm, 2010, pp. 27-35, vol. 50.
Bellemain-Appaix A, Brieger D, Beygiu F, et al., New P2Y12 inhibitors versus clopidogrel in percutaneous coronary intervention. A meta-analysis, J Am Coll Cardiol, 2010, pp. 1542-1551, vol. 56.
Bhatt DL, Lincoff AM, Gibson CM, et al., Intravenous platelet blockade with cangrelor during PCI, N Engl J Med, 2009, pp. 2330-41, vol. 361.
Buckland RJ, Judge HM, Sugidachi A, et al., Reversible binding of cangrelor to the P2Y12 receptor prevents the binding of clopidogrel and prasugrel active metabolites, J Thromb Haemost, 2009, p. 942, vol. 7(Suppl 2).
Buckland R, Judge HM, Sugidachi A, et al., Cangrelor inhibits the binding of clopidogrel and prasugrel active metabolites to the P2Y12 receptor, Eur Heart J, 2009, p. 193, vol. 30(Suppl 1).
Desai NR, Bhatt DL, The state of periprocedural antiplatelet therapy after recent trials, J Am Coll Cardiol Into, 2010, pp. 571-83, vol. 3.
Faxon DP, Cangrelor for ACS—lessons from the Champion trials, Nat Rev Cardiol, 2010, pp. 124-125, vol. 7.
Ferreiro JL, Ueno M, Angiolillo DJ, Cangrelor: a review on its mechanism of action and clinical development, Expert Rev Cardiovasc Ther, 2009, pp. 1195-1201, vol. 7.
Norgard NB, Cangrelor: a novel P2Y12 receptor antagonist, Expert Opin Investig Drugs, 2009, pp. 1219-1230, vol. 18.
Oestreich JH, Steinhubl SR, Cangrelor in percutaneous coronary intervention, Expert Rev Clin Pharmcol, 2009, pp. 137-145, vol. 2.
Oliphant CS, Doby JB, Blade CL, et al., Emerging P2Y12 receptor antagonists:role in coronary artery disease, Curr Vasc Pharmacol, 2010, pp. 93-101, vol. 8.
Paikin JS, Eikelboom JW, Cairns JA, et al., New antithrombotic agents-insights from clinical trials, Nat Rev Cardiol, 2010, pp. 498-509, vol. 7.
Ravnefjord A, Delavaux P, Tornvall J, et al., Ongoing treatment with cangrelor, but not ticagrelor, is associated with a significant reduction in the efficacy of clopidogrel in an ex-vivo canine model, J Thromb Haemost, 2009, p. 349, vol. 7(Suppl 2).

(56) References Cited

OTHER PUBLICATIONS

Sabatine MS, Novel antiplatelet strategies in acute coronary syndromes, Clev Clin J Med, 2009, pp. S8-S15, vol. 76(suppl 1).
Siddique A, Butt M, Shantsila E, et al., New antiplatelet drugs: beyond aspirin and clopidogrel, Int J Clin Pract, 2009, pp. 776-789, vol. 63.
Van Giezen JJ, Humphries RG, Preclinical and clinical studies with selective reversible direct P2Y12 antagonists, Semin Thromb Hemost, 2005, pp. 195-204, vol. 31, No. 2.
Van Giezen JJ, Optimizing platelet inhibition, Eur Heart J, 2008, pp. D23-D29, vol. 10(Suppl D).
Vasiljev KS, Uri A, Laitinen JT, 2-Alkylthio-substituted platelet P2Y12 receptor antagonists reveal pharmacological identity between the rat brain Gi-linked Adp receptors and P2Y12, Neuropharmcol, 2003, pp. 145-154, vol. 45, No. 1.
Wang K, Zhou X, Zhou Z, et al.,Blockade of the platelet P2Y12 receptor by AR-C69931MX sustains coronary artery recanalization and improves the myocardial tissue perfusion in a canine thrombosis model, Arterioscler Thromb Vasc Biol, 2003, pp. 357-362, vol. 23, No. 1.
Wang K, Zhou X, Zhou Z, et al., Sustained coronary artery recanalization with adjunctive infusion of a novel P2T-receptor antagonist AR-C69931 in a canine model, JACC, 2000, pp. 281A-82A, vol. 35(2 Suppl).
Wang K, Zhou X, Zhou Z, et al., Blockade of the ADP P2T receptor sustains coronary artery recanalization and improves the myocardium tissue perfusion in the canine thrombosis model, Circulation, 2001, p. 96, vol. 104 (17 Suppl).
Weaver WD, Becker R, Harrington R, et al., Safety and efficacy of a novel direct P2T receptor antagonist, AR C6991MX, in patients undergoing percutaneous coronary intervention, Eur Heart J, 2000, p. 382, vol. 21 (Suppl).
Weaver WD, Harrington RA, Grines CL, et al., Intravenous AR C69931MX, a novel P2T platelet receptor antagonist, in patients undergoing percutaneous coronary interventions preliminary results from a placebo or active controlled trial, JACC, 2000, pp. 36A-37A, vol. 35 (2SupplA).
Wiviott SD, De Lemos JA, Antiplatelet agents make a comeback in ST-elevation myocardial infarction, Am Heart J, 2007, pp. 603-606, vol. 154.
Wiviott SD, Michelson AD, Berger PB, et al., Therapeutic goals for effective platelet inhibition: a consensus document, Rev Cardiovasc Med, 2006, pp. 214-225, vol. 7.
Barker CM, Price MJ, Antiplatelet therapy in acute coronary syndromes, Curr Cardiol Rep, 2008, pp. 327-333, vol. 10, No. 4.
Geisler T, Gawaz M, Steinhubl SR, et al., Current strategies in antiplatelet therapy—Does identification of risk and adjustment of therapy contribute to more effective, personalized medicine in cardiovascular disease?, Pharmacol Ther, 2010, pp. 95-107, vol. 127.
Phillips DR, Conley PB, Sinha U, Andre P, Therapeutic approaches in arterial thrombosis, J Thromb Haemost, 2005, pp. 1577-1589, vol. 3.
Schneider DJ, Sobel BE, Streamlining the design of promising clinical trials: in-vitro testing of antithrombotic regimens and multiple agonists of platelet activation, Coron Artery Dis, 2009, pp. 175-178, vol. 20, No. 2.
Schomig A. et al., Ticagrelor-is there need for a new player in the antiplatelet-therapy field? N Engl J Med 361:1108-11 (2009).
Stone G.W. et al., Paclitaxel-eluting stents versus bare-metal stents in acute myocardial infarction. N Engl J Med 360:1946-59 (2009).
Bavry A.A. et al., Appropriate use of drug-eluting stents: balancing the reduction in restenosis with the concern of late thrombosis Lancet 371:2134-33 (2008).
Thygesen K. et al, Universal definition of myocardial infarction. Circulation 116:2634-53 (2007).
Cutlip D.E. et al., Clinical end points in coronary stent trials: a case for standardized definitions. Circulation 115:2344-51 (2007).
The GUSTO Investigators. An international randomized trial comparing four thrombolytic strategies for acute myocardial infarction. N Engl J Med 329:673-82 (1993).
Chesebro J.H. et al., Thrombolysis in Myocardial Infarction (TIMI) Trial, Phase I: A comparison between intravenous tissue plasminogen activator and intravenous streptokinase. Clinical findings through hospital discharge. Circulation 76: 142-54 (1987).
Stone G.W. et al., Bivalirudin for patients with acute coronary syndromes. N Engl J Med 355:2203-16 (2006).
International Conference on Harmonization (ICH) Guidance Documents. U.S. Food and Drug Administration Web site. (Accessed on Oct. 8, 2009, at the FDA website beginning with "www." and ending with "fda.gov/Regulatory Information/Guidances/ucm 122049.htm".
Mahaffey K.W. et al., Misreporting of myocardial infarction end points: results of adjudication by a central clinical avents committee in the Paragon-B trial. Second Platelet IIb/IIIa Antagonist for the Reduction of Acute Coronary Syndrome Events in a Global Organization Network Trial. Am Heart J 143:242-8 (2002).
Trissel L.A. et al., Physical compatibility of melphalan with selected drugs during simulated Y-site administration. Am J Hosp Pharm 50:2359-63 (1993).
Trissel L.A. et al. Turbidimetric assessment of the compatibility of taxol with 42 other drugs during simulated Y-site Injection. Am J Hosp Pharm 50:300-4 (1993).
Trissel et al.Turbidimetric assessment of the compatibility of taxol with 42 other drugs during simulated Y-site injection. Am J Hosp Pharm, 49:1716-9 (1992).
The article "What are the risks of percutaneous coronary intervention" (NHLBI, NIH. http://www.nhlbi.nih.gov/health/health-topics/topics/angioplasty/risks.html, Aug. 28, 2014.
Leonardi et al. A novel approach to systematically implement the universal definition of myocardial infarction: insights from the Champion Platform trial, Heart, 2013, pp. 1282-1287, vol. 99.
Angiolillo et al. Pharmacodynamic effects of cangrelor and clopidogrel: the platelet function substudy from the angrelor versus standard therapy to achieve optimal management of platelet inhibition (Champion) trials. J Thromb Thrombolysis 2012, pp. 44-55, vol. 44.
Fox et al. Effects on platelet function of an EP3 receptor antagonist used alone and in combination with a P2Y12 antagonist both in-vitro and ex-vivo in human volunteers. Platelets,2013, pp. 392-400, vol. 24, No. 5.
Ravnefjord et al. Evaluation of ticagrelor pharmacodynamic interactions with reversibly binding or non-reversibly binding P2Y(12) antagonists in an ex-vivo canine model. Thromb Res. Oct. 2012;130(4):622-8.
Ansel et al. "Pharmaceutical Dosage forms and Drug Delivery Systems", Lippincott Williams and Wilkins, 1999, pp. 48-53.
Beers et al., (eds.) :Coronary Artery Disease, Chapter 73 in the Merck manual of Diagnosis and Therapy, 18th edition, Merck & Co., Inc., Rahway, NJ, Jan. 2006, title pages and text pp. 626-652.
Lepantalo et al., Anti platelet effect of clopidogrel in patients with aspirin therapy undergoing percutaneous coronary interventions— limited inhibition of the P2Y12 receptor, Thromb. Res., 2009, pp. 193-198, vol. 124, No. 2.
Angiolillo, D. J. et al. Bridging Antiplatelet Therapy With Cangrelor in Patients Undergoing Cardiac Surgery: a randomized controlled trial, Supplementary Online Content, JAMA, 2012, pp. 265-274, vol. 307, No. 3.
Steg, P. G. et al. Ticagrelor Versus Clopidogrel in Patients With ST-Elevation Acute Coronary Syndromes Intended for Reperfusion With Primary Percutaneous Coronary Intervention A Platelet Inhibition and Patient Outcomes (PLATO) Trial Subgroup Analysis. Circulation, 2010, pp. 2131-2141, vol. 122, No. 3.
NCT00305162 Clinical Trials.gov Archive, https://clinicaltrials.gov/ct2/archive/NCT00305162, May 19, 2009.
Iyu D, Glenn JR, White AE, et al., Adenosine derived from ADP can contribute to inhibition of platelet aggregation in the presence of a P2YI2 antagonist, Arterioscler Thromb Vasc Biol, 2011, pp. 416-422, vol. 31.

(56) References Cited

OTHER PUBLICATIONS

Leonardi S, Mahaffey KW, White HD, et al., Rationale and design of the cangrelor versus standard therapy to acHieve optimal management of platelet inhibitiON PHOENIX trial, Am Heart J, 2012, pp. 768- 776.e2, vol. 163.
White HD, Chew DP, Dauerman HL, et al., Reduced immediate ischemic events with cangrelor in PCI: A pooled analysis of the Champion trials using the universal definition of myocardial infarction, Am Heart J, 2012, pp. 182-190.e4, vol. 163.
Bhatt DL, Stone GW, Mahaffey KW, et al. Effect of platelet inhibition with cangrelor during PCI on ischemic events. N Engl J Med, 2013, pp. 1303-1313, vol. 368.
Wallentin, "P2Y12 inhibitors: differences in properties and mechanisms of action and potential consequences for clinical use", European Heart Journal, 2009, pp. 1964-1977; published ahead of print Jul. 24, 2009.
Firstenberg, M.S., et al., P4-Safety and Efficacy of Cangrelor, An Intravenous, Short-Acting Platelet Inhibitor in Patients Requiring Cardiac Surgery, American Association for Thoracic Surgery, 2012.
Becker, R.C., et al., Management of Platelet-Directed Pharmacotherapy in Patients With Atherosclerotic Coronary Artery Disease Undergoing Elective Endoscopic Gastrointestinal Procedures, JACC, 2009, pp. 2261-2276, vol. 54, No. 24.
Bassand, J-P, Unmet needs in antiplatelet therapy, EHJ Supplements, 2008, pp. D3-DI 1, vol. 10, Supp. D.
Krajewski, S., et al., Short-acting P2Y 12 blockade to reduce platelet dysfunction and coagulopathy during experimental extracorporeal circulation and hypothennia, BJA, 2012, pp. 912-921, vol. 108, No. 6.
Xiang, B., et al., The P2Y 12 Antagonists, 2MeSAMP and Cangrelor, Inhibit Platelet Activation through P2Y12/Gi-Dependent Mechanism, PLOS One, 2012, pp. 1-10, vol. 7, Issue 12.
Straub, A., et al., Evidence of Platelet Activation at Medically Used Hypothennia and Mechanistic Data Indicating ADP as a Key Mediator and Therapeutic Target, JARA, 2011, pp. 1607-1016.
Bhatt, D.L., et al., Effect of platelet inhibition with cagrelor during PCI on ischemic events, 2013, N Engl J Med, pp. 1-15. Supplementary Appendix, Champion Phoenix.
Storey, R.F., et al., Inhibition of Platelet Aggregation by AZD6140, A Reversible Oral P2YI2 Receptor Antagonist, Compared with Clopidogrel in Patients with Acute Coronary Syndromes, JACC, 2007, pp. 1852-1856, vol. 50, No. 19.
Gurbel, P., et al., Oral Dosing of PRT060128, a Novel Direct-Acting, Reversible-P2Y(I2) Antagonist Overcomes High Platelet Reactivity in Patients Non-Responsive to Clopidogrel Therapy, Circulation, 2008, p. S972, vol. 118, No. 18.
Brilakis et al., Perioperative Management of Patients with Coronary Stents, JACC, 2007, pp. 2145-2150, vol. 49.
Bonello, et al., Consensus and Future Directions on the Definition of High On-Treatment Platelet Reactivity to Adenosine Diphosphate, JACC, 2010, pp. 919-933, vol. 56.
Price, et al., Standard- vs High-Dose Clopidogrel Based on Platelet Function Testing After Percutaneous Coronary Intervention, JAMA, 2011, pp. 1097-1105, vol. 305, No. 11.
Gurbel, et al., Peri-Operative Platelet Function Testing: The Potential for Reducing Ischaemic and Bleeding Risks, Thromb. Haemost., 2011, pp. 248-252, vol. 106.
Accumetric, LLC, VerifyNow User System User Manual, 2009.
Voisin, et al., Are P2Y12 Reaction Unit (PRU) and % Inhibition Index Equivalent for the Expression of P2Y12 Inhibition by the VerifyNowe® Assay? Role of Haematocrit and Haemoglobin Levels, Thromb. Haemost, 2011, pp. 227-229, vol. 106.
International Search Report and Written Opinion by the International Searching Authority, dated Jun. 30, 2009, in the PCT Application No. PCT/US09/43820.
International Search Report and Written Opinion by the International Searching Authority, dated Jan. 3, 2014, in the PCT Application No. PCT/US2013/048735.
International Search Report and Written Opinion by the International Searching Authority, dated Jun. 11, 2009, in the PCT Application No. PCT/US09/42681.
Angiolillo DJ, et al., Randomized Comparison of a High Clopidogrel Maintenance Dose in Patients with Diabetes Mellitus and Coronary Artery Disease, Circulation, 2007, 708-716, 115.
International Search Report and Written Opinion by the International Searching Authority, dated Feb. 10, 2015, in the PCT Application No. PCT/US2014/059972.
International Search Report and Written Opinion by the International Searching Authority, dated Jun. 2, 2014, in the PCT Application No. PCT/US2013/048741.
Leonardi S, et al, Pre-treatment with thienopyridines reduces the amount of myonecrosis in acute coronary syndrome patients invasively managed: insights from the Champion trials, Circulation, 2010, p. AI4813, vol. 122, No. 21, Suppl. S.
Hall R, et al., Antiplatelet drugs: a review of their pharmacology and management in the perioperative period, Anesthesia & Analgesia, 2011, pp. 292-318, vol. 112, No. 2.
NCT00767507 Clinical Trials.gov Archive, https://clinicaltrials.gov/archive/NCT00767507/2011_08_08, Aug. 8, 2011.
NCT00767507 Clinical Trials.gov Archive, https://clinicaltrials.gov/archive/NCT00767507/2008_10_06, Oct. 6, 2008.
Dovlatova et al., "Competition Between Reversible and Irreversible P2Y12 Antagonists and Its Influence on ADP-Mediated Platelet Activation," Journal of Thrombosis and Haemostasis, 5(Suppl. 2), Abstract No. S-340 (2007), only Abstract supplied.
Firstenberg, M.S., et al., Safety and Efficacy of Cangrelor, an Intravenous, Short-Acting Platelet Inhibitor in Patients Requiring Coronary Artery Bypass Surgery, The Heart Surgery Forum, 2013, pp. E60-E69, vol. 16, No. 2.
Windecker S. et al., Late Coronary Stent Thrombosis Circulation 116:1952-65 (2007).
Maisel W.H., Unanswered Questions—Drug-Eluting Stents and the Risk of Late Thrombosis N Engl J Med 356:981-4 (2007).
Popma J.J. et al., Antithrombotic therapy during percutaneous coronary intervention: the Seventh ACCP Conference on Antithrombotic and Thrombolytic Therapy.Chest 126:576S-99S (2004).
Gruntzig A.R. et al., Nonoperative dilatation of coronary-artery stenosis: percutaneous transluminal coronary angioplasty. N Engl J Med 301:61-8 (1979).
King S.B. 3rd. et al., 2007 Focused Update of the ACC/AHA/SCAI 2005 Guideline Update for Percutaneous Coronary Intervention: a report of the American College of Cardiology/American Heart Association Task Force on Practice Guidelines: 2007 Writing Group to Review New Evidence and Update the ACC/AHA/SCAI 2005 Guideline Update for Percutaneous Coronary Intervention, Writing on Behalf of the 2005 Writing Committee. Circulation 117:261-95 (2008).
Silber S. et al., Guidelines for percutaneous coronary interventions. The Task Force for Percutaneous Coronary Interventions of the European Society of Cardiology. Eur Heart J 26:804-47 (2005).
Gurbel P.A. et al., The relation of dosing to clopidogrel responsiveness and the incidence of high post-treatment platelet aggregation in patients undergoing coronary stenting. J Am Coll Cardiol 45: 1392-6 (2005).
Collet J.P. et al., Cytochrome P450 2C19 polymorphism in young patients treated with clopidogrel after myocardial nfarction: a cohort study. Lancet 373:309-17 (2009).
Mega J.L. et al., Cytochrome p-450 polymorphisms and response to clopidogrel. N Engl J Med 360:354-62 (2009).
Surbel P.A. et al., Drug insight: Clopidogrel nonresponsiveness. Nature Clin Pract Cardiovasc Med 3:387-95 (2006).
Meadows T.A. et al. Clinical aspects of platelet inhibitors and thrombus formation. Circ Res 100:1261-75 (2007).
Wiviott S.D. et al. Prasugrel versus clopidogrel in patients with acute coronary syndromes. N Engl J M ed 357:2001-15 (2007).
Bhatt D.L, Intensifying platelet inhibition—navigating between Scylla and Charybdis. N Engl J Med 357:2078-81 (2007).
Bhatt D.L, Prasugrel in clinical practice. N Engl J M ed 361:940-2 (2009).

(56) References Cited

OTHER PUBLICATIONS

Wallentin L et al., Ticagrelor versus clopidogrel in patients with acute coronary syndromsyndromes. N Engl J Med 361:1045-57 (2009).

* cited by examiner

METHODS OF TREATING OR PREVENTING STENT THROMBOSIS

BACKGROUND OF THE INVENTION

Stent thrombosis is a serious medical complication associated with the implantation of stents into the vasculature system, such as in the coronary artery. The presence of both bare-metal stents (BMS) and drug-eluting stents (DES) can induce platelet adhesion, activation and thrombus formation on or near the stent. Windecker S. et al., *Circulation* 116:1952-65 (2007); Maisel W. H., *N Engl J Med* 356:981-4 (2007). Stent thrombosis can occur during the implantation of a stent into a patient, such as during percutaneous coronary intervention (PCI). Popma J. J. et al., *Chest* 126:576 S-99S (2004). Thrombus formation may also develop over time, with acute (<24 hours post implantation), sub-acute (>24 hours and <30 days post implantation), late (>30 days and <12 months post implantation) or very late (>12 months post implantation) stent thrombosis comprising additional complications associated with the presence of a stent within the vasculature. Given the risk of thrombus formation, anti-thrombotic therapy has been an important adjunct to PCI since its inception. Grüntzig A. R. et al., *N Engl J Med* 301:61-8 (1979).

Recommended anti-platelet treatments include clopidogrel, a thienopyridine platelet adenosine diphosphate (ADP) receptor blocker, which is administered during and after PCI. King S. B. 3rd. et al., *Circulation* 117:261-95 (2008); Silber S. et al., *Eur Heart J* 26:804-47 (2005). The optimal timing, loading dose, and duration of clopidogrel therapy has not been definitively established by randomized clinical trials, but current guidelines recommend a 300-600 mg clopidogrel load (preferably before the procedure) followed by 75 mg daily.

Anti-platelet treatments, such as clopidogrel treatment, are not without a risk of complications. Multiple studies have now demonstrated that the pharmacokinetic and pharmacodynamic effects of clopidogrel are highly variable (Gurbel P. A. et al., *J Am Coll Cardiol* 45:1392-6 (2005); Collet J. P. et al., *Lancet* 373:309-17 (2009)) and may be influenced by genetic polymorphisms. Mega J. L. et al., *N Engl J Med* 360:354-62 (2009). These biologic interactions translate into differential pharmacodynamic and therapeutic responses, leading to the notion of clopidogrel "non-responders." Gurbel P. A. et al., *Nature Clin Pract Cardiovasc Med* 3:387-95 (2006). Clopidogrel also has a delayed onset of action even when given with a loading dose. Meadows T. A. et al., *Circ Res* 100:1261-75 (2007). Moreover, many physicians refrain from administering clopidogrel prior to angiographic definition of coronary anatomy, as this irreversible platelet inhibitor has been associated with an increased risk of perioperative bleeding if coronary artery bypass surgery is required rather than percutaneous revascularization. More potent oral ADP blockers have been tested and found to reduce ischemic outcomes even further, but with increased rates of bleeding. Wiviott S. D. et al., *N Engl J Med* 357:2001-15 (2007); Bhatt D. L., *N Engl J Med* 357:2078-81 (2007); Bhatt D. L., *N Engl J Med* 361:940-2 (2009); Wallentin L. et al., *N Engl J Med* 361:1045-57 (2009); Schomig A. et al., *N Engl J Med* 361:1108-11 (2009).

Thus, even in the contemporary era, the vexing problem of stent thrombosis has not been eliminated. Stone G. W. et al., *N Engl J Med* 360:1946-59 (2009); Bavry A. A. et al., *Lancet* 371:2134-33 (2008). Accordingly, there is a continuing need for potent anti-thrombotic agents with fast onset and fast offset of action that provide a desirable combination of effectiveness in treating or preventing stent thrombosis and an absence of an excessive risk of bleeding.

SUMMARY OF THE INVENTION

As shown herein, the present invention demonstrates that the excellent properties of cangrelor may be utilized in the treatment and/or prevention of stent thrombosis. The properties of cangrelor may also be utilized in the treatment and/or prevention of myocardial infarction.

In a first embodiment, the present invention is directed to a method of treating or preventing stent thrombosis in a subject in need thereof, comprising administering to the subject an effective amount of a pharmaceutical composition comprising cangrelor, thereby treating or preventing stent thrombosis in a subject.

The skilled artisan will understand that some combinations of therapy may be beneficial due to additive or synergistic effects of the compounds in the combination therapy. Therefore, a second embodiment of the invention is directed to the use of cangrelor and bivalirudin in the treatment or prevention of stent thrombosis in a subject. Thus, the invention is also directed to a method of treating or preventing stent thrombosis in a subject in need thereof, comprising administering to the subject an effective amount of a pharmaceutical composition comprising cangrelor and bivalirudin, thereby treating or preventing stent thrombosis in a subject.

The skilled artisan will further understand that combination therapy may be accomplished through the separate administration of the therapeutic agents, whether concurrently or sequentially. Therefore, in a third embodiment the present invention is directed to a method of treating or preventing stent thrombosis in a subject in need thereof, comprising administering to the subject an effective amount of a first pharmaceutical composition comprising cangrelor and administering to the subject an effective amount of a second pharmaceutical composition comprising bivalirudin, thereby treating or preventing stent thrombosis in a subject.

In related embodiments, cangrelor may be used in methods of reducing mortality in a subject undergoing implantation of a stent. Thus, in a fourth embodiment, the invention is directed to a method of reducing mortality in a subject undergoing stent implantation, comprising administering to the subject an effective amount of a pharmaceutical composition comprising cangrelor, thereby reducing mortality in a subject undergoing stent implantation.

As in the methods discussed above, methods of reducing mortality in a subject may be practiced using combination therapy. The invention is therefore directed, in a fifth embodiment, to a method of reducing mortality in a subject undergoing stent implantation, comprising administering to the subject an effective amount of a pharmaceutical composition comprising cangrelor and bivalirudin, thereby reducing mortality in a subject undergoing stent implantation. And in a sixth embodiment, where the combination therapy may be accomplished through the separate administration of the therapeutic agents, whether concurrently or sequentially, the invention is directed to a method of reducing mortality in a subject undergoing stent implantation, comprising administering to the subject an effective amount of a first pharmaceutical composition comprising cangrelor and administering to the subject an effective amount of a second pharmaceutical composition comprising bivalirudin, thereby reducing mortality in a subject undergoing stent implantation.

In a seventh embodiment, the invention is directed to a method of treating or preventing myocardial infarction in a subject in need thereof, comprising administering to the subject an effective amount of a pharmaceutical composition comprising cangrelor, thereby treating or preventing myocardial infarction in a subject.

In an eighth embodiment, the invention is directed to a method of treating or preventing myocardial infarction in a subject in need thereof, comprising administering to the subject an effective amount of a pharmaceutical composition comprising cangrelor and bivalirudin, thereby treating or preventing myocardial infarction in a subject.

In a ninth embodiment, the invention is directed to a method of treating or preventing myocardial infarction in a subject in need thereof, comprising administering to the subject an effective amount of a first pharmaceutical composition comprising cangrelor and administering to the subject an effective amount of a second pharmaceutical composition comprising bivalirudin, thereby treating or preventing myocardial infarction in a subject.

In related embodiments, cangrelor may be used in methods of reducing mortality in a subject experiencing myocardial infarction. Thus, in a tenth embodiment, the invention is directed to a method of reducing mortality in a subject experiencing myocardial infarction, comprising administering to the subject an effective amount of a pharmaceutical composition comprising cangrelor, thereby reducing mortality in a subject experiencing myocardial infarction.

As in the methods discussed above, methods of reducing mortality in a subject may be practiced using combination therapy. The invention is therefore directed, in an eleventh embodiment, to a method of reducing mortality in a subject experiencing myocardial infarction, comprising administering to the subject an effective amount of a pharmaceutical composition comprising cangrelor and bivalirudin, thereby reducing mortality in a subject experiencing myocardial infarction. And in a twelfth embodiment, where the combination therapy may be accomplished through the separate administration of the therapeutic agents, whether concurrently or sequentially, the invention is directed to a method of reducing mortality in a subject experiencing myocardial infarction, comprising administering to the subject an effective amount of a first pharmaceutical composition comprising cangrelor and administering to the subject an effective amount of a second pharmaceutical composition comprising bivalirudin, thereby reducing mortality in a subject experiencing myocardial infarction.

In a thirteenth embodiment, the invention encompasses a medicament comprising an effective amount of cangrelor useful for treating or preventing stent thrombosis. In a related, fourteenth embodiment, the invention encompasses a medicament comprising an effective amount of cangrelor and bivalirudin useful for treating or preventing stent thrombosis.

In a fifteenth embodiment, the invention encompasses a medicament comprising an effective amount of cangrelor useful for treating or preventing myocardial infarction. In a related, sixteenth embodiment, the invention encompasses a medicament comprising an effective amount of cangrelor and bivalirudin useful for treating or preventing myocardial infarction.

In a seventeenth embodiment, the invention encompasses a medicament comprising an effective amount of cangrelor useful for reducing mortality in a subject undergoing stent implantation. In a related, eighteenth embodiment, the invention encompasses a medicament comprising an effective amount of cangrelor and bivalirudin useful for reducing mortality in a subject undergoing stent implantation.

In a nineteenth embodiment, the invention encompasses a medicament comprising an effective amount of cangrelor useful for reducing mortality in a subject experiencing myocardial infarction. In a related, twentieth embodiment, the invention encompasses a medicament comprising an effective amount of cangrelor and bivalirudin useful for reducing mortality in a subject experiencing myocardial infarction.

In a twenty-first embodiment, the present invention includes a pharmaceutical composition comprising cangrelor and bivalirudin. The pharmaceutical composition may further comprise a pharmaceutically acceptable carrier or diluent. For example, the pharmaceutical composition may comprise 1 mg/mL cangrelor and 1 mg/mL bivalirudin in 0.9% NaCl; 1 mg/mL cangrelor and 5 mg/mL bivalirudin in 0.9% NaCl; 5 mg/mL cangrelor and 1 mg/mL bivalirudin in 0.9% NaCl; 5 mg/mL cangrelor and 5 mg/mL bivalirudin in 0.9% NaCl; 1 mg/mL cangrelor and 1 mg/mL bivalirudin in 5% dextrose; 1 mg/mL cangrelor and 5 mg/mL bivalirudin in 5% dextrose; 5 mg/mL cangrelor and 1 mg/mL bivalirudin in 5% dextrose; or 5 mg/mL cangrelor and 5 mg/mL bivalirudin in 5% dextrose. In this twenty-first embodiment, the pharmaceutical composition is effective in treating or preventing stent thrombosis, and in reducing mortality in a subject undergoing stent implantation. In this twenty-first embodiment, the pharmaceutical composition is also effective in treating or preventing myocardial infarction, as well as in reducing mortality in a subject experiencing myocardial infarction.

In a twenty-second embodiment, the present invention includes a method of preparing a medicament useful for treating or preventing stent thrombosis, comprising admixing cangrelor with a pharmaceutically acceptable carrier or diluent. In a related, twenty-third embodiment, the present invention includes a method of preparing a medicament useful for treating or preventing stent thrombosis, comprising admixing cangrelor and bivalirudin with a pharmaceutically acceptable carrier or diluent.

In a twenty-fourth embodiment, the present invention includes a method of preparing a medicament useful for treating or preventing myocardial infarction, comprising admixing cangrelor with a pharmaceutically acceptable carrier or diluent. In a related, twenty-fifth embodiment, the present invention includes a method of preparing a medicament useful for treating or preventing myocardial infarction, comprising admixing cangrelor and bivalirudin with a pharmaceutically acceptable carrier or diluent.

In a twenty-sixth embodiment, the present invention includes a method of preparing a medicament useful for reducing mortality in a subject undergoing stent implantation, comprising admixing cangrelor with a pharmaceutically acceptable carrier or diluent. In a related, twenty-seventh embodiment, the present invention includes a method of preparing a medicament useful for reducing mortality in a subject undergoing stent implantation, comprising admixing cangrelor and bivalirudin with a pharmaceutically acceptable carrier or diluent.

In a twenty-eighth embodiment, the present invention includes a method of preparing a medicament useful for reducing mortality in a subject experiencing myocardial infarction, comprising admixing cangrelor with a pharmaceutically acceptable carrier or diluent. In a related, twenty-ninth embodiment, the present invention includes a method of preparing a medicament useful for reducing mortality in a subject experiencing myocardial infarction, comprising admixing cangrelor and bivalirudin with a pharmaceutically acceptable carrier or diluent.

In each of the relevant embodiments, stent thrombosis may result from any means related to the implantation, presence, or maintenance of a stent in the vasculature of a subject. For example, stent thrombosis may be induced by implantation of a stent, such as bare-metal stent or a drug-eluting stent, into a subject. Similarly, stent thrombosis may develop over time due to the presence of a stent, such as a bare-metal stent or a drug-eluting stent, in the subject. Thus, in each of these embodiments, stent thrombosis may be intraprocedural stent thrombosis, acute stent thrombosis, sub-acute stent thrombosis, late stent thrombosis or very late stent thrombosis. Further, in each of these embodiments, the prevention of stent thrombosis may be prevention during percutaneous coronary intervention (PCI) or other vascular stent implantation.

In each of the relevant embodiments, the stent implantation includes implantation of a stent, such as a bare-metal stent or a drug-eluting stent, into a subject. The stent implantation is implantation during percutaneous coronary intervention (PCI) or other vascular stent implantation.

In each of the relevant embodiments, myocardial infarction may be any form of myocardial infarction, including acute myocardial infarction, healing myocardial infarction, healed myocardial infarction, acute non-ST-elevated myocardial infarction and acute ST-elevated myocardial infarction. Myocardial infarction may be induced by any mechanism, including implantation of a stent, such as a bare-metal stent or a drug-eluting stent, into the subject, or other vascular stent implantation, or arise during percutaneous coronary intervention (PCI).

In each of the relevant embodiments, mortality may be caused by intraprocedural stent thrombosis, acute stent thrombosis, sub-acute stent thrombosis, late stent thrombosis or very late stent thrombosis, or occlusion of a coronary artery.

The pharmaceutical compositions comprising cangrelor, comprising bivalirudin, or comprising both cangrelor and bivalirudin, may be independently administered to a subject orally, as an intravenous bolus, as a continuous intravenous infusion, or as an intravenous bolus followed by a continuous intravenous infusion.

DETAILED DESCRIPTION OF THE INVENTION

Figure 1:
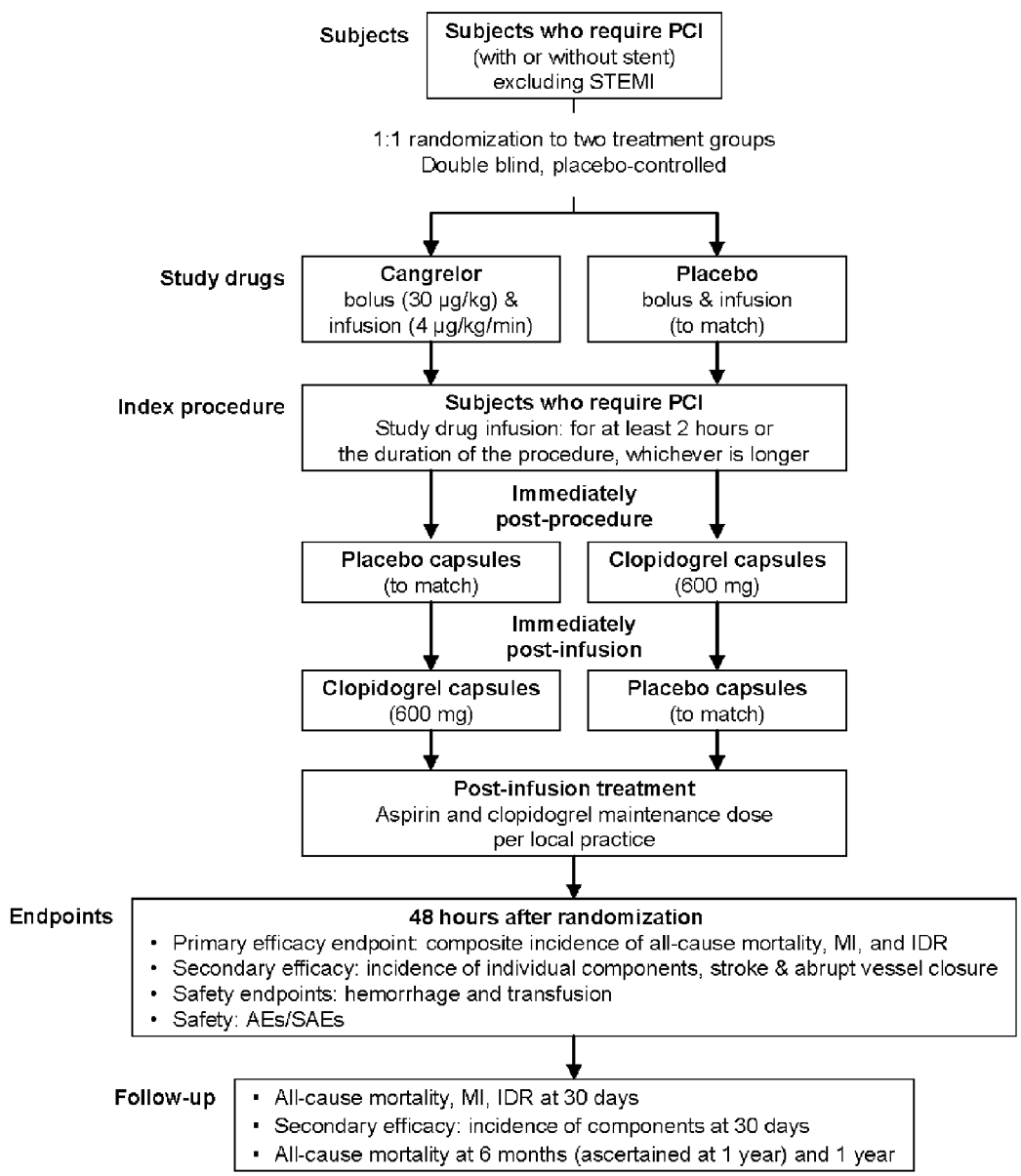
FIG. 1—diagram showing trial designed for a study of the efficacy of cangrelor versus placebo administered to patients during percutaneous coronary intervention (PCI).

The present invention is based on the discovery that the cangrelor, a reversible, fast acting, adenosine triphosphate analogue inhibitor of the P2Y$_{12}$ ADP receptor, is effective in treating and preventing thrombus formation associated with implanted vascular stents. Cangrelor is effective, whether administered alone or in combination with one or more other anti-thrombotic agents, such as bivalirudin, in the treatment and prevention of stent thrombosis.

Cangrelor is a non-thienopyridine adenosine triphosphate analogue which reversibly binds to and inhibits the P2Y$_{12}$ ADP receptor. Cangrelor is direct-acting, reversible, and selective, and it has a short half-life. It is metabolized through dephosphorylation pathways and has a plasma half-life of 3-5 minutes; platelet function returns to normal within 30-60 minutes of drug termination. Storey R. F. et al., *Br J Haematol* 110:925-34 (2000). When given as a bolus plus infusion, it quickly and consistently inhibits platelets to a high degree with normalization of platelet function shortly after discontinuation. A phase 2 trial in patients undergoing PCI demonstrated dose-dependent platelet inhibition similar to that achieved with abciximab, less bleeding time prolongation, and more rapid return to platelet function. Greenbaum A. B. et al., *Am Heart J* 151:689.e1-10 (2006). The chemical structure of cangrelor is shown in Formula I.

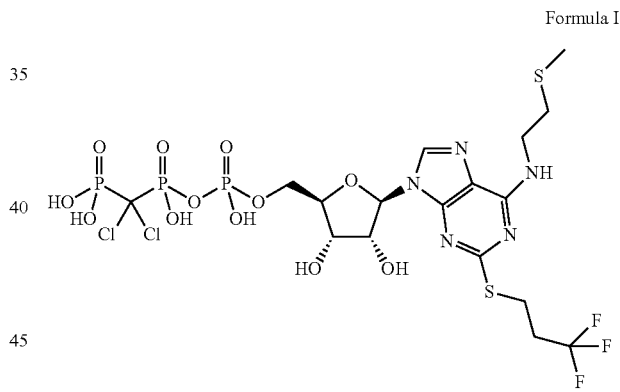

Formula I

In each of the embodiments of the present invention, the term "cangrelor" encompasses the compound of Formula I, as well as tautomeric, enantiomeric and diastereomeric forms thereof, and racemix mixtures thereof, other chemically active forms thereof, and pharmaceutically acceptable salts of these compounds, including a tetrasodium salt. These alternative forms and salts, processes for their production, and pharmaceutical compositions comprising them, are well known in the art and set forth, for example, in U.S. Pat. No. 5,721,219. Additional disclosure relevant to the production and use of cangrelor may be found in U.S. Pat. Nos. 5,955,447, 6,130,208 and 6,114,313, as well as in U.S. Appln. Publication No. 2006/0270607.

Bivalirudin is a potent, reversible inhibitor of the serine protease thrombin. Thrombin is critical in the thrombotic process, cleaving fibrinogen into fibrin monomers and converting Factor XIII to Factor XIIIa, thereby allowing fibrin to develop into a covalently cross-linked framework which leads to clot formation. The chemical structure of bivalirudin is shown in Formula II.

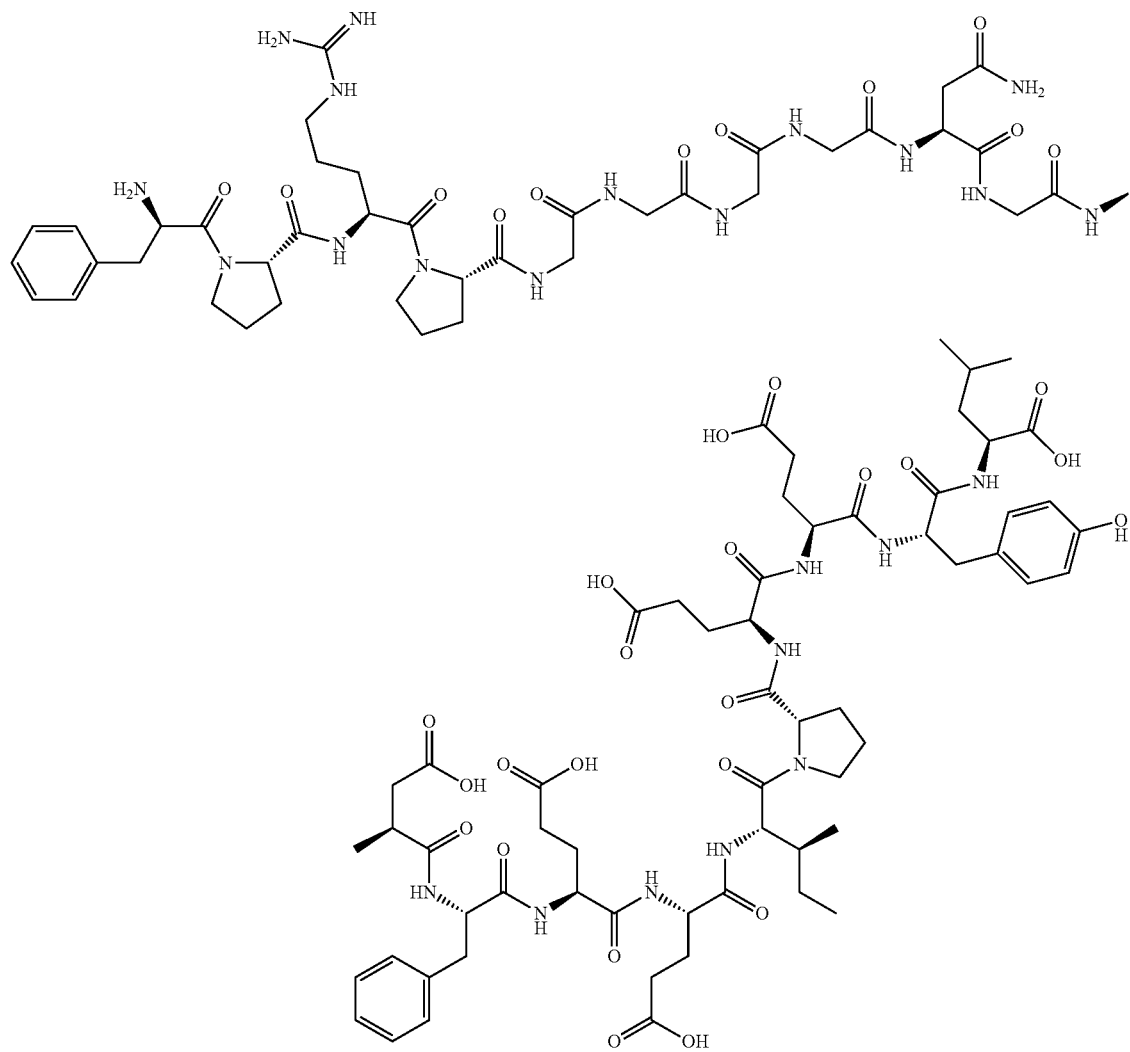

Formula II

In each of the embodiments of the present invention, the term "bivalirudin" encompasses the compound of Formula II as well as pharmaceutically acceptable salts thereof. Salts of bivalirudin, processes for the production of bivalirudin, and pharmaceutical compositions comprising bivalirudin, are well known in the art and set forth, for example, in U.S. Pat. No. 5,196,404.

Stent Thrombosis and Stent Implantation

In each of the embodiments of the invention related to the treatment or prevention of stent thrombosis, stent thrombosis may result from any means related to the implantation, presence, or maintenance of the stent in the vasculature of a subject. For example, stent thrombosis may be induced by implantation of a stent, such as a bare-metal stent, a drug-eluting stent, or other type of stent into the subject. Similarly, stent thrombosis may develop over time due to the presence of a stent, such as a bare-metal stent, a drug-eluting stent, or other type of stent in the subject. Thus, in each of the embodiments of the present invention stent thrombosis may be intraprocedural stent thrombosis, acute stent thrombosis (<24 hours post implantation), sub-acute stent thrombosis (>24 hours and <30 days post implantation), late stent thrombosis (>30 days and <12 months post implantation) or very late stent thrombosis (>12 months post implantation).

Further, in each of these embodiments, the prevention of stent thrombosis may be prevention in the course of stent implantation during percutaneous coronary intervention (PCI) or other vascular stent implantation procedure.

In each of the embodiments of the invention related to the implantation of a stent, the stent implantation may be implantation of a bare-metal stent, a drug-eluting stent, or other type of stent into a subject. The stent implantation is implantation during percutaneous coronary intervention (PCI) or other vascular stent implantation. The mortality associated with stent implantation may be mortality due to intraprocedural stent thrombosis, acute stent thrombosis, sub-acute stent thrombosis, late stent thrombosis or very late stent thrombosis.

Myocardial Infarction

In each of the embodiments of the invention related to the treatment or prevention of myocardial infarction, or reducing mortality in a subject experiencing myocardial infarction, myocardial infarction may be any form of myocardial infarction, including acute myocardial infarction (first few hours to 7 days), healing myocardial infarction (7 to 28 days), healed myocardial infarction (29 days and beyond), acute non-ST-elevated myocardial infarction and acute ST-elevated myocardial infarction. Myocardial infarction may be induced by any mechanism, including implantation of a bare-metal stent or a drug-eluting stent into the subject, or other vascular stent implantation, or arise during percutaneous coronary intervention (PCI). Myocardial infarction may also be caused by intraprocedural stent thrombosis, acute stent thrombosis, sub-acute stent thrombosis, late stent thrombosis, very late stent thrombosis or occlusion of a coronary artery. Mortality may be caused by intraprocedural stent thrombosis, acute stent thrombosis, sub-acute stent thrombosis, late stent thrombosis or very late stent thrombosis, or occlusion of a coronary artery.

Pharmaceutical Compositions

In each aspect and embodiment of the present invention, cangrelor and bivalirudin (when present) are formulated and administered to a subject in the form of a pharmaceutical composition comprising the active agent(s) and, optionally, a pharmaceutically acceptable carrier, diluent and/or excipient. Thus, the present invention encompasses: (i) a pharmaceutical composition comprising cangrelor, and optionally a pharmaceutically acceptable carrier, diluent and/or excipient; (ii) a pharmaceutical composition comprising bivalirudin, and optionally a pharmaceutically acceptable carrier, diluent and/or excipient; and (iii) a pharmaceutical composition comprising cangrelor and bivalirudin, and optionally a pharmaceutically acceptable carrier, diluent and/or excipient. As used herein, the term "medicament" is synonymous with "pharmaceutical composition."

Suitable carriers and diluents are well known to those skilled in the art and include saline, such as 0.9% NaCl, buffered saline, dextrose (e.g., 5% dextrose in water), water, Water-for-Injection (WFI), glycerol, ethanol, propylene glycol, polysorbate 80 (Tween-80™), 0.002% polysorbate 80 (Tween-80™), poly(ethylene)glycol 300 and 400 (PEG 300 and 400), PEGylated castor oil (e.g. Cremophor EL), poloxamer 407 and 188, a cyclodextrin or a cyclodextrin derivative (including HPCD ((2-hydroxypropyl)-cyclodextrin) and (2-hydroxyethyl)-cyclodextrin, hydrophilic and hydrophobic carriers, and combinations thereof. Hydrophobic carriers include, for example, fat emulsions, lipids, PEGylated phospholipids, polymer matrices, biocompatible polymers, liposhperes, vesicles, particles, and liposomes. The terms specifically exclude cell culture medium.

Excipients included in a pharmaceutical composition have different purposes depending, for example on the nature of the drugs, and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweeteners, perfuming agents, flavouring agents, coloring agents, administration aids, and combinations thereof.

The pharmaceutical composition may contain common carriers and excipients, such as cornstarch or gelatin, lactose, sucrose, microcrystalline cellulose, kaolin, mannitol, dicalcium phosphate, sodium chloride, alginic acid, croscarmellose sodium, and sodium starch glycolate.

The particular carrier, diluent or excipient used will depend upon the means and purpose for which the active ingredient is being applied.

The pharmaceutical compositions of the present invention may be formulated, for example, for oral, sublingual, intranasal, intraocular, rectal, transdermal, mucosal, topical or parenteral administration. Parenteral modes of administration include without limitation, intradermal, subcutaneous (s.c., s.q., sub-Q, Hypo), intramuscular (i.m.), intravenous (i.v.), intraperitoneal (i.p.), intra-arterial, intramedulary, intracardiac, intra-articular (joint), intrasynovial (joint fluid area), intracranial, intraspinal, and intrathecal (spinal fluids). Any known device useful for parenteral injection or infusion of drug formulations can be used to effect such administration. In noted aspects and embodiments of the present invention, administration of the pharmaceutical compositions is via parenteral administration, preferably intravenous administration, or oral administration.

In intravenous (IV) administration, a sterile formulation of the pharmaceutical compositions of the present invention and optionally one or more additives, including solubilizers or surfactants, can be dissolved or suspended in any of the commonly used intravenous fluids and administered by infusion. Intravenous fluids include, without limitation, physiological saline, 0.9% NaCl, phosphate buffered saline, 5% dextrose in water, 0.002% polysorbate 80 (Tween-80™) in water or Ringer's™ solution.

In intramuscular preparations, a sterile formulation of the pharmaceutical compositions of the present invention can be dissolved and administered in a pharmaceutical diluent such as Water-for-Injection (WFI), physiological saline, 0.9% NaCl or 5% dextrose in water.

For oral use, the oral pharmaceutical composition may be made in the form of a unit dosage containing a therapeutically-effective amount of the pharmaceutical compositions. Solid formulations such as tablets and capsules are particularly useful. Sustained released or enterically coated preparations may also be devised. For pediatric and geriatric applications, suspension, syrups and chewable tablets are especially suitable. For oral administration, the pharmaceutical compositions are in the form of, for example, tablets, capsules, suspensions or liquid syrups or elixirs, wafers and the like. For general oral administration, excipient or additives include, but are not limited to inert diluents, fillers, disintegrating agents, binding agents, wetting agents, lubricating agents, sweetening agents, flavoring agents, coloring agents and preservatives.

For therapeutic purposes, the tablets and capsules can contain, in addition to the active agents, conventional carriers such as: inert diluents (e.g., sodium and calcium carbonate, sodium and calcium phosphate, and lactose), binding agents (e.g., acacia gum, starch, gelatin, sucrose, polyvinylpyrrolidone (Povidone), sorbitol, tragacanth methylcellulose, sodium carboxymethylcellulose, hydroxypropyl methylcellulose, and ethylcellulose), fillers (e.g., calcium phosphate, glycine, lactose, maize-starch, sorbitol, or sucrose), wetting agents, lubricating agents (e.g., metallic stearates, stearic acid, polyethylene glycol, waxes, oils, silica and colloical silica, silicon fluid or talc), disintegrating agents (e.g., potato starch, corn starch and alginic acid), flavouring (e.g. peppermint, oil of wintergreen, fruit flavoring, cherry, grape, bubblegum, and the like), and coloring agents. Carriers may also include coating excipients such as glyceryl monostearate or glyceryl distearate, to delay absorption in the gastrointestinal tract.

Pharmaceutical compositions comprising cangrelor of the present invention include pharmaceutical compositions comprising from about 0.1 to about 50 mg/ml of cangrelor. Particular examples of pharmaceutical compositions comprising cangrelor include the following: (i) cangrelor at a concentration of about 0.1, 0.5, 1, 2, 3, 4, 5, 6, 7, 8, 9, or 10 mg/mL in 0.9% NaCl, and (ii) cangrelor at a concentration of about 0.1, 0.5, 1, 2, 3, 4, 5, 6, 7, 8, 9, or 10 mg/mL in 5% dextrose. The pharmaceutical composition may further comprise a pharmaceutically acceptable carrier or diluent.

Pharmaceutical compositions comprising bivalirudin of the present invention include pharmaceutical compositions comprising from about 0.1 to about 50 mg/ml of bivalirudin. Particular examples of pharmaceutical compositions comprising bivalirudin include the following: (i) bivalirudin at a concentration of about 0.1, 0.5, 1, 2, 3, 4, 5, 6, 7, 8, 9, or 10 mg/mL in 0.9% NaCl, and (ii) bivalirudin at a concentration of about 0.1, 0.5, 1, 2, 3, 4, 5, 6, 7, 8, 9, or mg/mL in 5% dextrose. The pharmaceutical composition may further comprise a pharmaceutically acceptable carrier or diluent.

When the pharmaceutical composition comprises both cangrelor and bivalirudin, the relative amounts of cangrelor and bivalirudin can vary widely depending on the use to which the final formulations will be put. However, in preferred embodiments cangrelor and bivalirudin will be present in the pharmaceutical composition at a molecular weight ratio of from about 25:1 to about 1:25, such as about 25:1, 20:1, 15:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, 1:20, 1:25. Pharmaceutical compositions comprising cangrelor and bivalirudin of the present invention include pharmaceutical compositions comprising from about 0.1 to about 50 mg/ml of cangrelor, and from about 0.1 to about 50 mg/ml of bivalirudin. Particular examples of pharmaceutical compositions comprising cangrelor and bivalirudin include the following: cangrelor at a concentration of about 0.1, 0.5, 1, 2, 3, 4, 5, 6, 7, 8, 9, or 10 mg/mL and bivalirudin at a concentration of about 0.1, 0.5, 1, 2, 3, 4, 5, 6, 7, 8, 9, or 10 mg/mL in 0.9% NaCl. Specific examples include: (i) about 1 mg/mL cangrelor and about 1 mg/mL bivalirudin in 0.9% NaCl, (ii) about 1 mg/mL cangrelor and about 5 mg/mL bivalirudin in 0.9% NaCl, (iii) about 5 mg/mL cangrelor and about 1 mg/mL bivalirudin in 0.9% NaCl, and (iv) about 5 mg/mL cangrelor and about 5 mg/mL bivalirudin in 0.9% NaCl. The pharmaceutical composition may further comprise a pharmaceutically acceptable carrier or diluent.

Further examples of pharmaceutical compositions comprising cangrelor and bivalirudin include the following: (i) cangrelor at a concentration of about 0.1, 0.5, 1, 2, 3, 4, 5, 6, 7, 8, 9, or mg/mL and bivalirudin at a concentration of about 0.1, 0.5, 1, 2, 3, 4, 5, 6, 7, 8, 9, or 10 mg/mL in 5% dextrose. Specific examples include: (i) about 1 mg/mL cangrelor and about 1 mg/mL bivalirudin in 5% dextrose, (ii) about 1 mg/mL cangrelor and about 5 mg/mL bivalirudin in 5% dextrose, (iii) about 5 mg/mL cangrelor and about 1 mg/mL bivalirudin in 5% dextrose, and (iv) about 5 mg/mL cangrelor and about 5 mg/mL bivalirudin in 5% dextrose. The pharmaceutical composition may further comprise a pharmaceutically acceptable carrier or diluent.

In preferred aspects, the pH of the pharmaceutical compositions of the present invention ranges from about 5 to about 8. In specific examples, the pH is about 5, 5.5, 6, 6.5, 7, 7.5, or 8.

In other aspects, a pharmaceutical composition comprising cangrelor and bivalirudin is prepared where the pharmaceutical composition comprises cangrelor, bivalirudin, a stabilizer and a buffering agent in an isotonic solution. In preferred aspects, the stabilizer is a saccharide, a polysaccharide, or an amino acid. In particularly preferred aspects, the stabilizer is sucrose or mannitol. In other preferred aspects, the buffering agent is NaCl, NaOH or sodium citrate. Specific examples include:

| | |
|---|---|
| Cangrelor | 12.5 mg |
| Bivalirudin | 250 mg |
| Mannitol | 125 mg |
| NaOH | 12.5 mg |
| Cangrelor | 25 mg |
| Bivalirudin | 250 mg |
| Mannitol | 125 mg |
| NaOH | 12.5 mg |
| Cangrelor | 50 mg |
| Bivalirudin | 250 mg |
| Mannitol | 125 mg |
| NaOH | 12.5 mg |

In another aspect, a pharmaceutical composition is prepared by combining cangrelor, bivalirudin, a stabilizer and a buffering agent in a sterile vial that is subjected to lyophilization. Such a formulation will be stable and will have a long shelf life, up to at least about one month, six months, one year, or more. Upon use, but prior to administration, the composition will be reconstituted in a pharmaceutically acceptable diluent for injection or infusion, including water for injection, saline (e.g., 0.9% w/v sodium chloride solution for injection) and dextrose (e.g., 5% w/v dextrose solution for infusion). The lyophilized composition may be reconstituted with a pharmaceutically acceptable diluent within about 10, 20, 30, 40, 50 or 60 minutes prior to administration to a subject, or within about 1, 2, 3, 4, 5 or 6 days prior to administration to a subject, or within about 1, 2, 3, 4, 5 or 6 weeks prior to administration to a subject.

Dosage

As used herein, the terms "dose", "dosage", "unit dose", "unit dosage", "effective dose", "effective amount" and related terms refer to physically discrete units that contain a predetermined quantity of cangrelor, or bivalirudin, or both, calculated to produce a desired therapeutic effect. These terms are synonymous with the therapeutically effective amounts and amounts sufficient to achieve the stated goals of the methods disclosed herein.

Particular doses of the pharmaceutical compositions comprising cangrelor, or bivalirudin, or both, of the present invention will vary depending upon the stated goals of the methods (treating, preventing or reducing), the physical characteristics of the subject, the size and location of the thrombus, existence of related or unrelated medical conditions, the composition of the formulation and the means used to administer the drug to the subject. The specific dose for a given subject will generally be set by the judgment of the attending physician.

When administered as an intravenous (IV) formulation, a pharmaceutical composition comprising cangrelor may be administered as a bolus, as a continuous infusion, or as a bolus followed by a continuous infusion. When administered as a bolus, a dose of about 5, 10, 15, 20, 25, 30, 35, 40, 45, 50, 55, 60, 65, 70, 75, 80, 85, 90, 95 or 100 ug/kg cangrelor, or more, is administered to the subject. In preferred embodiments, between about 20 and 40 ug/kg cangrelor is administered, more preferably about 30 ug/kg. When administered as a continuous infusion, cangrelor may be administered at about 0.1, 0.5, 1, 2, 3, 4, 5, 6, 7, 8, 9, 10, 15, 20, 25, 30 ug/kg/min, or more, to the subject. In preferred embodiments, between about 1 and 10 ug/kg/min cangrelor is administered, more preferably about 4 ug/kg/min. The skilled artisan will understand that different dosages may be administered during different points of the stent implantation procedure. Thus the dosages may differ in the periods before implantation, during implantation and after implantation.

Similarly, when administered as an intravenous (IV) formulation, a pharmaceutical composition comprising bivalirudin may be administered as a bolus, as a continuous infusion, or as a bolus followed by a continuous infusion. When administered as a bolus, a dose of about 0.05, 0.1, 0.25, 0.5, 0.75, 1, 5, 10, 15, 20, 25, 30, 35, 40, 45 or 50 mg/kg bivalirudin, or more, is administered to the subject. In preferred embodiments, between about 0.1 and 10 mg/kg bivalirudin is administered, more preferably about 0.75 mg/kg. When administered as a continuous infusion, bivalirudin may be administered at about 0.1, 0.25, 0.5, 0.75, 1, 1.25, 1.5, 1.75, 2, 2.25, 2.5, 2.75, 3, 4, 5, 6, 7, 8, 9, 10, 15, 20, 25, 30 mg/kg/h, or more, to the subject. In preferred embodiments, between about 0.5 and 10 mg/kg/h bivalirudin is administered, more preferably about 1.75 mg/kg/h. The skilled artisan will understand that different dosages may be administered during different points of the stent implantation procedure. Thus the dosages may differ in the periods before implantation, during implantation and after implantation.

IV formulations comprising both cangrelor and bivalirudin may be prepared using the same guidelines above for IV formulations comprising either cangrelor or bivalirudin alone.

In each of the embodiments where the pharmaceutical composition is administered as continuous intravenous infusion, the infusion may continue for at least about 10, 15, 20, 30, 40, 50, 60, 70, 80, 90, 100, 120, 130, 140, 150, 160, 170, 180, 190, 200, 220, 240, 260, 280, 300, 320, 340 or 360 minutes, or more. The skilled artisan will understand that the period of time over which the pharmaceutical composition is administered may be shorter or longer than the indicated times due to the particular characteristics of a subject.

Where the pharmaceutical composition is administered in conjunction with the implantation of a stent, such as during PCI, the bolus may be administered within about 360, 300, 240, 180, 120, 90, 60, 30 or 15 minutes prior to the beginning of the procedure.

When administered orally, cangrelor is administered in an oral dosage of between about 0.5 to about 100 mg per kg body weight of the subject per day to which the oral formulation is being administered, more preferably about 5 to about 30 mg per kg body weight per day, including about 5, 10, 15, 20, 25 and 30 mg per kg body weight per day. Oral administration may be as a single dose (bolus) per day or divided into multiple doses. When multiple doses are administered orally, administration may be once, twice, thrice or more times per day.

When administered orally, bivalirudin is administered in an oral dosage of between about 0.5 to about 100 mg per kg body weight of the subject per day to which the oral formulation is being administered, more preferably about 5 to about 30 mg per kg body weight per day, including about 5, 10, 15, 20, 25 and 30 mg per kg body weight per day. Oral administration may be as a single dose (bolus) per day or divided into multiple doses. When multiple doses are administered orally, administration may be once, twice, thrice or more times per day.

Oral formulations comprising both cangrelor and bivalirudin may be prepared using the same guidelines above for oral formulations comprising either cangrelor or bivalirudin alone.

In addition to the pharmaceutical compositions of the present invention comprising cangrelor and/or bivalirudin, the skilled artisan will understand that one, two, three, four, five or more additional anti-thombotic agents may be used in combination with cangrelor and/or bivalirudin. For example, aspirin (100-500 mg daily) may be administered in conjunction with the pharmaceutical compositions.

Course of Treatment—Single Pharmaceutical Composition

The course of treatment associated with the methods of the present invention will depend on the particular method being practiced.

When the method being practiced is a method of treating stent thrombosis using a pharmaceutical composition, whether comprising cangrelor alone, or both cangrelor and bivalirudin, the course of treatment will generally follow implantation of a stent into a subject, where the subject is suspected of having or known to have developed a thrombus associated with a stent. The pharmaceutical composition comprising cangrelor (and bivalirudin when present) may be in an oral dosage form, a bolus intravenous dosage form or a continuous intravenous infusion dosage form. The course of treatment may last for a period of hours, days, weeks, months or years. The pharmaceutical composition comprising cangrelor (and bivalirudin when present) may thus be administered to a subject to treat stent thrombosis for about 1, 2, 3, 4, 5, 6, or 7 days, for about 1, 2, 3 or 4 weeks, or for about 1, 2, 3, 4, 5, 6, 7, 8, 9, 10, 11, 12 or more months, after the implantation of a vascular stent or after a diagnosis of stent thrombosis. In particular aspects, the pharmaceutical composition may be administered to the subject orally, as an intravenous bolus, as a continuous intravenous infusion, as an intravenous bolus followed by continuous intravenous infusion, or some combination thereof. In a particular example, the pharmaceutical composition is administered to the subject in a continuous intravenous infusion dosage form over a period of at least about 0.5, 1, 1.5, 2, 2.5, 3, 3.5 or 4 hours, or more. The methods of treatment of the present invention include methods wherein the pharmaceutical composition is administered to the subject beginning about 1, 2, 3, 4, 5, 6, 7, 8, 9, 10, 11, 12, 13, 14 or 15 months, or more, after stent implantation. The treatment may be once, twice, thrice or more times a day, once every two days, once every three days, once every four days, once every five days, once every six days, once a week, once every 10 days, once every two weeks, once every three weeks, once a month, or even less frequently.

When the method being practiced is a method of treating myocardial infarction or reducing mortality in a subject experiencing myocardial infarction using a pharmaceutical composition, whether comprising cangrelor alone, or both cangrelor and bivalirudin, the course of treatment will generally follow diagnosis of myocardial infarction or at the onset of symptoms of myocardial infarction. The pharmaceutical composition comprising cangrelor (and bivalirudin when present) may be in an oral dosage form, a bolus intravenous dosage form or a continuous intravenous infusion dosage form. In preferred aspects, the pharmaceutical composition is administered to the subject within about 5, 10, 15, 20, 30, 40, 50, 60, 70, 80 or 90 minutes of the onset of symptoms of myocardial infarction. The course of treatment may last for a period of hours, days or weeks. The pharmaceutical composition comprising cangrelor (and bivalirudin when present) may thus be administered to a subject to treat myocardial infarction or to reduce mortality for about 1, 2, 3, 4, 5 or more hours after diagnosis of myocardial infarction or at the onset of symptoms of myocardial infarction, and be repeated for a number of days or weeks. In particular aspects, the pharmaceutical composition may be administered to the subject orally, as an intravenous bolus, as a continuous intravenous infusion, as an intravenous bolus followed by continuous intravenous infusion, or some combination thereof. In a particular example, the pharmaceutical composition is administered to the subject in a continuous intravenous infusion dosage form over a period of at least about 0.5, 1, 1.5, 2, 2.5, 3, 3.5 or 4 hours, or more. The treatment may be once, twice, thrice or more times a day, once every two days, once every three days, once every four days, once every five days, once every six days, once a week, once every 10 days, once every two weeks, once every three weeks, once a month, or even less frequently.

In the methods of the invention directed to methods of reducing mortality in a subject experiencing myocardial infarction, mortality may be reduced within a period of about 24, 36 or 48 hours after myocardial infarction, within a period of about 30 days after myocardial infarction, within a period of about six months after myocardial infarction, or within a period of about one year after myocardial infarction. In preferred embodiments, mortality is reduced by at least about 0.2%, 0.4%, 0.6%, 0.8%, 1.0% or 1.2% during the period in comparison to a subject not receiving cangrelor.

When the method being practiced is a method of preventing stent thrombosis or reducing mortality in a subject undergoing stent implantation, whether using a pharmaceutical composition comprising cangrelor alone, or both cangrelor and bivalirudin, the course of treatment will generally be associated with a medical procedure in which a stent is being implanted into the subject. The course of treatment may be limited to the administration of a pharmaceutical composition comprising cangrelor (and bivalirudin when present) prior to the beginning of the procedure, during the procedure or after the procedure. Alternatively, the course of treatment may comprise administering the pharmaceutical composition prior to the procedure and during the procedure, or during the procedure and after the procedure, or prior to the procedure and after the procedure. The skilled artisan will also understand that the course of treatment may begin prior to the procedure and continue until some point after the completion of the procedure. The skilled artisan will understand that the pharmaceutical composition may be administered to the subject via different dosage forms, such as via intravenous infusion during the procedure and an oral dosage form for a number of days or months after the procedure has been completed.

When administered before stent implantation, the pharmaceutical composition is preferably administered to the subject in an oral dosage form, a bolus intravenous dosage form, a continuous intravenous infusion dosage form, or as an intravenous bolus followed continuous intravenous infusion, within about 0.5, 1, 1.5, 2, 2.5, 3, 3.5, 4, 4.5, 5, 5.5, 6, 6.5, 7 or 7.5 hours, or more, prior to stent implantation. When administered as a continuous intravenous infusion dosage form, the pharmaceutical composition is preferably administered to the subject as a continuous intravenous infusion over about a 0.5, 1, 1.5, 2, 2.5, 3, 3.5 or 4 hour period, or more.

When administered during stent implantation, the pharmaceutical composition is preferably administered to the subject in an oral dosage form, a bolus intravenous dosage form, a continuous intravenous infusion dosage form, or as an intravenous bolus followed continuous intravenous infusion. When administered as a continuous intravenous infusion, the infusion may continue over about a 0.5, 1, 1.5, 2, 2.5, 3, 3.5 or 4 hour period, or more. The continuous intravenous infusion may also simply last for the duration of the procedure.

When administered after stent implantation, the pharmaceutical composition is preferably administered to the subject in an oral dosage form, a bolus intravenous dosage form, a continuous intravenous infusion dosage form, or as an intravenous bolus followed continuous intravenous infusion, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When administered as a continuous intravenous infusion, the infusion may continue over about a 0.5, 1, 1.5, 2, 2.5, 3, 3.5 or 4 hour period, or more.

When administered both before and during the procedure, the pharmaceutical composition may be administered to the subject in an oral dosage form, a bolus intravenous dosage form, a continuous intravenous infusion dosage form, or as an intravenous bolus followed continuous intravenous infusion, within about 0.5, 1, 1.5, 2, 2.5, 3, 3.5, 4, 4.5, 5, 5.5, 6, 6.5, 7 or 7.5 hours, or more, prior to stent implantation, and administered to the subject in an oral dosage form, a bolus intravenous dosage form, a continuous intravenous infusion dosage form, or as an intravenous bolus followed continuous intravenous infusion, during the procedure. When administered as a continuous intravenous infusion, the infusion may continue over about a 0.5, 1, 1.5, 2, 2.5, 3, 3.5 or 4 hour period, or more. The continuous intravenous infusion may also simply last for the duration of the procedure.

When administered during and after the procedure, the pharmaceutical composition may be administered to the subject in an oral dosage form, a bolus intravenous dosage form, a continuous intravenous infusion dosage form, or as an intravenous bolus followed continuous intravenous infusion, and administered to the subject in an oral dosage form, a bolus intravenous dosage form, a continuous intravenous infusion dosage form, or as an intravenous bolus followed continuous intravenous infusion, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When administered as a continuous intravenous infusion, the infusion may continue over about a 0.5, 1, 1.5, 2, 2.5, 3, 3.5 or 4 hour period, or more.

When administered both before and after the procedure, the pharmaceutical composition may be administered to the subject in an oral dosage form, a bolus intravenous dosage form, a continuous intravenous infusion dosage form, or as an intravenous bolus followed continuous intravenous infusion, within about 0.5, 1, 1.5, 2, 2.5, 3, 3.5, 4, 4.5, 5, 5.5, 6, 6.5, 7 or 7.5 hours, or more, prior to stent implantation, and administered to the subject in an oral dosage form, a bolus intravenous dosage form, a continuous intravenous infusion dosage form, or as an intravenous bolus followed continuous intravenous infusion, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When administered as a continuous intravenous infusion, the infusion may continue over about a 0.5, 1, 1.5, 2, 2.5, 3, 3.5 or 4 hour period, or more.

When administered before, during and after the procedure, the pharmaceutical composition may be administered to the subject (i) in an oral dosage form, a bolus intravenous dosage form, a continuous intravenous infusion dosage form, or as an intravenous bolus followed continuous intravenous infusion, within about 0.5, 1, 1.5, 2, 2.5, 3, 3.5, 4, 4.5, 5, 5.5, 6, 6.5, 7 or 7.5 hours, or more, prior to the procedure, (ii) in an oral dosage form, a bolus intravenous dosage form, a continuous intravenous infusion dosage form, or as an intravenous bolus followed continuous intravenous infusion, during the procedure, and (iii) in an oral dosage form, a bolus intravenous dosage form, a continuous intravenous infusion dosage form, or as an intravenous bolus followed continuous intravenous infusion, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When the dosage form is continuous intravenous infusion, the infusion may continue over about a 0.5, 1, 1.5, 2, 2.5, 3, 3.5 or 4 hour period, or more.

In the methods of the invention directed to methods of reducing mortality in a subject undergoing stent implantation, mortality may be reduced within a period of about 24, 36 or 48 hours after stent implantation, within a period of about 30 days after stent implantation, within a period of about six months after stent implantation, or within a period of about one year after stent implantation. In preferred embodiments, mortality is reduced by at least about 0.2%, 0.4%, 0.6%, 0.8%, 1.0% or 1.2% during the period in comparison to a subject not receiving cangrelor.

When the method being practiced is a method of preventing myocardial infarction using a pharmaceutical composition, whether comprising cangrelor alone, or both cangrelor and bivalirudin, the pharmaceutical composition may be administered to a subject as a prophylaxis against myocardial infarction. Subjects appropriate for such prevention would be any subject suspected of having a vascular thrombus, early symptoms of myocardial infarction or other disease or condition that could lead to myocardial infarction against which the pharmaceutical compositions of the invention would be effective. The pharmaceutical composition comprising cangrelor (and bivalirudin when present) may be in an oral dosage form, a bolus intravenous dosage form or a continuous intravenous infusion dosage form. In preferred aspects, the pharmaceutical composition is administered to the subject within about 5, 10, 15, 20, 30, 40, 50, 60, 70, 80 or 90 minutes of when early or initial symptoms of myocardial infarction are detected. The course of treatment may last for a period of hours, days or weeks. The pharmaceutical composition comprising cangrelor (and bivalirudin when present) may thus be administered to a subject to prevent myocardial infarction for about 1, 2, 3, 4, 5 or more hours after early or initial symptoms of myocardial infarction are detected, and be repeated for a number of days or weeks. In particular aspects, the pharmaceutical composition may be administered to the subject orally, as an intravenous bolus, as a continuous intravenous infusion, as an intravenous bolus followed by continuous intravenous infusion, or some combination thereof. In a particular example, the pharmaceutical composition is administered to the subject in a continuous intravenous infusion dosage form over a period of at least about 0.5, 1, 1.5, 2, 2.5, 3, 3.5 or 4 hours, or more. The treatment may be once, twice, thrice or more times a day, once every two days, once every three days, once every four days, once every five days, once every six days, once a week, once every 10 days, once every two weeks, once every three weeks, once a month, or even less frequently.

Course of Treatment—First and Second Pharmaceutical Compositions

When the method being practiced is a method of treating stent thrombosis using a first and second pharmaceutical composition, the course of treatment will also generally follow implantation of a stent in a subject, where the subject is suspected of having or known to have developed a thrombus associated with a stent. The first pharmaceutical composition comprising cangrelor and the second pharmaceutical composition comprising bivalirudin may independently be administered to the subject in an oral dosage form, a bolus intravenous dosage form, or a continuous intravenous infusion dosage form. The first and second pharmaceutical compositions may be administered to the subject concurrently or sequentially, in either order. As an example, the first and second pharmaceutical compositions may be administered to the subject sequentially, in either order, separated in time by about less than about 15, 30, 60, 75, 90, 105, 120, or more minutes.

The course of treatment may last for a period of days, weeks, months or years. The first and second pharmaceutical compositions may thus be administered to a subject to treat stent thrombosis for about 1, 2, 3, 4, 5, 6, or 7 days, for about 1, 2, 3 or 4 weeks, or for about 1, 2, 3, 4, 5, 6, 7, 8, 9, 10, 11, 12 or more months, after the implantation of a vascular stent or after a diagnosis of stent thrombosis. In particular aspects, the pharmaceutical compositions may each be independently administered to the subject orally, as an intravenous bolus, as a continuous intravenous infusion, as an intravenous bolus followed by continuous intravenous infusion, or some combination thereof. In a particular example, the first and second pharmaceutical compositions are administered to the subject in continuous intravenous infusion dosage forms over a period of at least about 0.5, 1, 1.5, 2, 2.5, 3, 3.5 or 4 hours, or more. The methods of treatment include methods wherein the pharmaceutical compositions are administered to the subject beginning about 1, 2, 3, 4, 5, 6, 7, 8, 9, 10, 11, 12, 13, 14 or 15 months, or more, after stent implantation. The treatment may be once, twice, thrice or more times a day, once every two days, once every three days, once every four days, once every five days, once every six days, once a week, once every 10 days, once every two weeks, once every three weeks, once a month, or even less frequently.

When the method being practiced is a method of treating myocardial infarction or reducing mortality in a subject experiencing myocardial infarction using a first and second pharmaceutical composition, the course of treatment will generally follow diagnosis of myocardial infarction or begin at the onset of symptoms of myocardial infarction. The first pharmaceutical composition comprising cangrelor and the second pharmaceutical composition comprising bivalirudin may independently be administered to the subject in an oral dosage form, a bolus intravenous dosage form, or a continuous intravenous infusion dosage form. The first and second pharmaceutical compositions may be administered to the subject concurrently or sequentially, in either order. As an example, the first and second pharmaceutical compositions may be administered to the subject sequentially, in either order, separated in time by about less than about 15, 30, 60, 75, 90, 105, 120, or more minutes.

In preferred aspects, the pharmaceutical compositions are administered to the subject within about 5, 10, 15, 20, 30, 40, 50, 60, 70, 80 or 90 minutes of the onset of symptoms of myocardial infarction. The course of treatment may last for a period of hours, days or weeks. The pharmaceutical compositions may thus be administered to a subject to treat myocardial infarction for about 1, 2, 3, 4, 5 or more hours after diagnosis of myocardial infarction or at the onset of symptoms of myocardial infarction, and be repeated for a number of days or weeks. In particular aspects, the pharmaceutical compositions may each be independently administered to the subject orally, as an intravenous bolus, as a continuous intravenous infusion, as an intravenous bolus followed by continuous intravenous infusion, or some combination thereof. In a particular example, the pharmaceutical compositions are administered to the subject in continuous intravenous infusion dosage forms over a period of at least about 0.5, 1, 1.5, 2, 2.5, 3, 3.5 or 4 hours, or more. The treatment may be once, twice, thrice or more times a day, once every two days, once every three days, once every four days, once every five days, once every six days, once a week, once every 10 days, once every two weeks, once every three weeks, once a month, or even less frequently.

In the methods of the invention directed to methods of reducing mortality in a subject experiencing myocardial infarction, mortality may be reduced within a period of about 24, 36 or 48 hours after myocardial infarction, within a period of about 30 days after myocardial infarction, within a period of about six months after myocardial infarction, or within a period of about one year after myocardial infarction. In preferred embodiments, mortality is reduced by at least about 0.2%, 0.4%, 0.6%, 0.8%, 1.0% or 1.2% during the period in comparison to a subject not receiving cangrelor and bivalirudin.

When the method being practiced is a method of preventing stent thrombosis or reducing mortality in subjects undergoing stent implantation using a first and second pharmaceutical composition, the course of treatment will again generally be associated with a medical procedure in which a stent is being implanted into the subject. The course of treatment may be limited to the administration of the pharmaceutical compositions prior to the beginning of the procedure, during the procedure or after the procedure. Alternatively, the course of treatment may comprise administering the pharmaceutical compositions prior to the procedure and during the procedure, or during the procedure and after the procedure, or prior to the procedure and after the procedure. The skilled artisan will also understand that the course of treatment may begin prior to the procedure and continue until some point after the completion of the procedure. The skilled artisan will understand that the pharmaceutical compositions may be administered to the subject via different dosage forms, such as via intravenous infusion during the procedure and oral dosage forms for a number of days or months after the procedure has been completed. As the two anti-thrombotic agents are prepared as separate pharmaceutical compositions, the skilled artisan will also understand that the first pharmaceutical composition (comprising cangrelor) and the second pharmaceutical composition (comprising bivalirudin) may be administered at different points during the procedure, e.g., prior to the beginning of the procedure, during the procedure or after the procedure.

In the methods of the invention directed to methods of prevention using a first and second pharmaceutical composition, the first and second pharmaceutical compositions may be independently administered to the subject in an oral dosage form, a bolus intravenous dosage form, a continuous intravenous infusion dosage form, or as an intravenous bolus followed continuous intravenous infusion, concurrently or sequentially, in either order.

When administered before stent implantation, the first and second pharmaceutical compositions are independently administered to the subject in an oral dosage form, a bolus intravenous dosage form, a continuous intravenous infusion dosage form, or as an intravenous bolus followed continuous intravenous infusion, concurrently or sequentially, in either order, within about 0.5, 1, 1.5, 2, 2.5, 3, 3.5, 4, 4.5, 5, 5.5, 6, 6.5, 7 or 7.5 hours, or more, prior to stent implantation. When administered in a continuous intravenous infusion dosage form, the pharmaceutical composition is administered over about a 0.5, 1, 1.5, 2, 2.5, 3, 3.5 or 4 hour period, or more.

When administered during stent implantation, first and second pharmaceutical compositions are independently administered to the subject in an oral dosage form, a bolus intravenous dosage form, a continuous intravenous infusion dosage form, or as an intravenous bolus followed continuous intravenous infusion, concurrently or sequentially, in either order, during the period of stent implantation. When administered as a continuous intravenous infusion, the infusion may continue over about a 0.5, 1, 1.5, 2, 2.5, 3, 3.5 or 4 hour period, or more. The continuous intravenous infusion may also simply last for the duration of the procedure.

When administered after stent implantation, the first and second pharmaceutical compositions are independently administered to the subject in an oral dosage form, a bolus intravenous dosage form, a continuous intravenous infusion dosage form, or as an intravenous bolus followed continuous intravenous infusion, concurrently or sequentially, in either order, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When administered as a continuous intravenous infusion, the infusion may continue over about a 0.5, 1, 1.5, 2, 2.5, 3, 3.5 or 4 hour period, or more.

When administered both before and during the procedure, the first and second pharmaceutical compositions are independently to the subject in an oral dosage form, a bolus intravenous dosage form, a continuous intravenous infusion dosage form, or as an intravenous bolus followed continuous intravenous infusion, concurrently or sequentially, in either order, within about 0.5, 1, 1.5, 2, 2.5, 3, 3.5, 4, 4.5, 5, 5.5, 6, 6.5, 7 or 7.5 hours, or more, prior to stent implantation, and independently administered to the subject in an oral dosage form, a bolus intravenous dosage form, a continuous intravenous infusion dosage form, or as an intravenous bolus followed continuous intravenous infusion, in any order, during the procedure. When administered as a continuous intravenous infusion, the infusion may continue over about a 0.5, 1, 1.5, 2, 2.5, 3, 3.5 or 4 hour period, or more. The continuous intravenous infusion may also simply last for the duration of the procedure.

When administered during and after the procedure, first and second pharmaceutical compositions are independently administered to the subject in an oral dosage form, a bolus intravenous dosage form, a continuous intravenous infusion dosage form, or as an intravenous bolus followed continuous intravenous infusion, concurrently or sequentially, in either order, during the procedure, and independently administered to the subject in an oral dosage form, a bolus intravenous dosage form, a continuous intravenous infusion dosage form, or as an intravenous bolus followed continuous intravenous infusion, concurrently or sequentially, in either order, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When administered as a continuous intravenous infusion, the infusion may continue over about a 0.5, 1, 1.5, 2, 2.5, 3, 3.5 or 4 hour period, or more.

When administered both before and after the procedure, the first and second pharmaceutical compositions are independently to the subject in an oral dosage form, a bolus intravenous dosage form, a continuous intravenous infusion dosage form, or as an intravenous bolus followed continuous intravenous infusion, concurrently or sequentially, in either order, within about 0.5, 1, 1.5, 2, 2.5, 3, 3.5, 4, 4.5, 5, 5.5, 6, 6.5, 7 or 7.5 hours, or more, prior to stent implantation, and independently administered to the subject in an oral dosage form, a bolus intravenous dosage form, a continuous intravenous infusion dosage form, or as an intravenous bolus followed continuous intravenous infusion, concurrently or sequentially, in either order, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When administered as a continuous intravenous infusion, the infusion may continue over about a 0.5, 1, 1.5, 2, 2.5, 3, 3.5 or 4 hour period, or more.

When administered before, during and after the procedure, the first and second pharmaceutical compositions are independently administered to the subject (i) in an oral dosage form, a bolus intravenous dosage form, a continuous intravenous infusion dosage form, or as an intravenous bolus followed continuous intravenous infusion, concurrently or sequentially, in either order, within about 0.5, 1, 1.5, 2, 2.5, 3, 3.5, 4, 4.5, 5, 5.5, 6, 6.5, 7 or 7.5 hours, or more, prior to the procedure, (ii) in an oral dosage form, a bolus intravenous dosage form, a continuous intravenous infusion dosage form, or as an intravenous bolus followed continuous intravenous infusion, concurrently or sequentially, in either order, during the procedure, and (iii) in an oral dosage form, a bolus intravenous dosage form, a continuous intravenous infusion dosage form, or as an intravenous bolus followed continuous intravenous infusion, concurrently or sequentially, in either order, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When the dosage form is continuous intravenous infusion, the infusion may continue over about a 0.5, 1, 1.5, 2, 2.5, 3, 3.5 or 4 hour period, or more.

In alternative aspects, the first and second pharmaceutical compositions may be administered to the subject during different stages of the stent implantation procedure. For example, either the first or second pharmaceutical composition may be administered to the subject in an oral dosage form, a bolus intravenous dosage form, a continuous intravenous infusion dosage form, or as an intravenous bolus followed continuous intravenous infusion, within about 0.5, 1, 1.5, 2, 2.5, 3, 3.5, 4, 4.5, 5, 5.5, 6, 6.5, 7 or 7.5 hours, or more, prior to beginning stent implantation. Of the two second pharmaceutical compositions, the one not utilized in the first step may be administered to the subject in an oral dosage form, a bolus intravenous dosage form, a continuous intravenous infusion dosage form, or as an intravenous bolus followed continuous intravenous infusion, during the period of stent implantation. When administered as a continuous intravenous infusion, the infusion may continue over about a 0.5, 1, 1.5, 2, 2.5, 3, 3.5 or 4 hour period, or more.

Similarly, either the first or second pharmaceutical composition may be administered to the subject in an oral dosage form, a bolus intravenous dosage form, a continuous intravenous infusion dosage form, or as an intravenous bolus followed continuous intravenous infusion, during the period of stent implantation. Of the two second pharmaceutical compositions, the one not utilized in the first step may be administered to the subject in an oral dosage form, a bolus intravenous dosage form, a continuous intravenous infusion dosage form, or as an intravenous bolus followed continuous intravenous infusion, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When administered as a continuous intravenous infusion, the infusion may continue over about a 0.5, 1, 1.5, 2, 2.5, 3, 3.5 or 4 hour period, or more.

Moreover, either the first or second pharmaceutical composition may be administered to the subject in an oral dosage form, a bolus intravenous dosage form, a continuous intravenous infusion dosage form, or as an intravenous bolus followed continuous intravenous infusion, within about 0.5, 1, 1.5, 2, 2.5, 3, 3.5, 4, 4.5, 5, 5.5, 6, 6.5, 7 or 7.5 hours, or more, prior to beginning stent implantation. Of the two second pharmaceutical compositions, the one not utilized in the first step may be administered to the subject in an oral dosage form, a bolus intravenous dosage form, a continuous intravenous infusion dosage form, or as an intravenous bolus followed continuous intravenous infusion, during the period of stent implantation. Either the first or second pharmaceutical composition may then be administered to the subject in an oral dosage form, a bolus intravenous dosage form, a continuous intravenous infusion dosage form, or as an intravenous bolus followed continuous intravenous infusion, for a period of about 0.25, 0.5, 0.75, 1, 1.5, 2, 2.5, 3, 3.5, 4, 4.5, 5, 5.5, 6, 6.5 or 7 hours, or more, after the completion of the procedure. When administered as a continuous intravenous infusion, the infusion may continue over about a 0.5, 1, 1.5, 2, 2.5, 3, 3.5 or 4 hour period, or more.

In the methods of the invention directed to methods of reducing mortality in a subject undergoing stent implantation, mortality may be reduced within a period of about 24, 36 or 48 hours after stent implantation, within a period of about 30 days after stent implantation, within a period of about six months after stent implantation, or within a period of about one year after stent implantation. In preferred embodiments, mortality is reduced by at least about 0.2%, 0.4%, 0.6%, 0.8%, 1.0% or 1.2% during the period in comparison to a subject not receiving cangrelor and bivalirudin.

When the method being practiced is a method of preventing myocardial infarction using the first and second pharmaceutical compositions, the pharmaceutical compositions may be administered to a subject as a prophylaxis against myocardial infarction. Subjects appropriate for such prevention would be any subject suspected of having a vascular thrombus, early symptoms of myocardial infarction or other disease or condition that could lead to myocardial infarction against which the pharmaceutical compositions of the invention would be effective. The first pharmaceutical composition comprising cangrelor and the second pharmaceutical composition comprising bivalirudin may independently be administered to the subject in an oral dosage form, a bolus intravenous dosage form, or a continuous intravenous infusion dosage form. The first and second pharmaceutical compositions may be administered to the subject concurrently or sequentially, in either order. In preferred aspects, the pharmaceutical compositions are administered to the subject within about 5, 10, 15, 20, 30, 40, 50, 60, 70, 80 or 90 minutes of when early or initial symptoms of myocardial infarction are detected. The course of treatment may last for a period of hours, days or weeks. The pharmaceutical compositions may thus be administered to a subject to prevent myocardial infarction for about 1, 2, 3, 4, 5 or more hours after early or initial symptoms of myocardial infarction are detected, and be repeated for a number of days or weeks. In particular aspects, the pharmaceutical compositions may each be independently administered to the subject orally, as an intravenous bolus, as a continuous intravenous infusion, as an intravenous bolus followed by continuous intravenous infusion, or some combination thereof. In a particular example, the administering is administration of the pharmaceutical compositions to the subject in a continuous intravenous infusion dosage form over a period of at least about 0.5, 1, 1.5, 2, 2.5, 3, 3.5 or 4 hours, or more. The treatment may be once, twice, thrice or more times a day, once every two days, once every three days, once every four days, once every five days, once every six days, once a week, once every 10 days, once every two weeks, once every three weeks, once a month, or even less frequently.

Subjects

As used herein, a "subject" upon which the methods of the present invention may be practiced refers to an animal, such as a mammalian or an avian species, including a human, a non-human primate, a horse, a cow, a sheep, a goat, a dog, and a cat. Such subjects may have stent thrombosis, be at risk of developing stent thrombosis, or be undergoing stent implantation. Thus, the subjects encompassed by the methods of the present invention include subjects undergoing vascular stent implantation and subjects having undergone vascular stent implantation.

In view of the fact that the subjects upon which some of the methods of the present invention are being practiced have underlying health conditions that require the implantation of a stent, the skilled artisan will understand that the subjects may have various additional physical characteristics. For example, in each of the embodiments of the present invention, the subject may have a condition selected from the group consisting of ST-segment elevation myocardial infarction (STEMI), non-ST-segment elevation myocardial infarction (NSTEMI), stable angina, unstable angina, and acute coronary syndrome. The subject may be about 75 years of age or less, or the subject may be about 75 years of age or more. The subject may be male or female. The subject may be about 60 kg in weight or less, or the subject may be about 60 kg in weight or more. The subject may have a baseline glomerular filtration rate (GFR) of about 50 or less, or the subject may have a baseline GFR of about 50 or more. The subject may have received a periprocedural glycoprotein IIb/IIIa inhibitor, or the subject may not have received a periprocedural glycoprotein IIb/IIIa inhibitor. The subject may have received periprocedural unfractionated heparin (UFH), or the subject may not have received UFH. The subject may have received periprocedural low-molecular-weight heparin (LMWH), or the subject may not have received periprocedural LMWH. The subject may have received periprocedural bivalirudin, or the subject may not have received periprocedural bivalirudin. The subject may have received periprocedural clopidogrel, or the subject may not have received periprocedural clopidogrel.

To further characterize the subjects to which the methods of the present invention may be applied, it is noted that the subject may have suffered a stroke, or the subject may not have suffered a stroke. The subject may have diabetes mellitus, or the subject may not have diabetes mellitus. The subject may have hypertension, or the subject may not have hypertension. The subject may have hyperlipidemia, or the subject may not have hyperlipidemia. The subject may have suffered a myocardial infarction, or the subject may not have suffered a myocardial infarction. The subject may have a family history of coronary artery disease (CAD), or the subject may not have a family history of CAD. The subject may have undergone percutaneous transluminal coronary angioplasty (PTCA), or the subject may not have undergone PTCA. The subject may have undergone percutaneous coronary intervention (PCI), or the subject may not have undergone PCI. The subject may have undergone coronary artery bypass graft (CABG), or the subject may not have undergone CABG. The subject may have congestive heart failure, or the subject may not have congestive heart failure. The subject may have peripheral arterial disease (PAD), or the subject may not have PAD. The subject may have stent thrombosis in more than one artery or vein.

Results of the Methods

Each of the methods recited in the present invention may include the additional step of measuring the effect or effectiveness of the pharmaceutical composition during or after administration of the compounds. In one example, the additional step of measuring an effect of the pharmaceutical composition may be performed about 0.5, 1, 1.5, 2, 2.5, 3, 3.5, 4, 4.5, 5, 10, 15, 20 or 24 hours, or more, after completion of a method of the invention. The effects that may be measured in the methods of the present invention include an increase in luminal diameter within the stent, a decrease in the size of the stent thrombus, and a decreased incidence of myocardial infarction. Each of these effects would demonstrate the effectiveness of the compounds comprising the pharmaceutical composition.

Example 1—Intravenous Platelet Blockade with Cangrelor Versus Placebo During Percutaneous Coronary Intervention In this example, the efficacy of cangrelor versus placebo was examined when administered to patients during percutaneous coronary intervention (PCI).

Patients were enrolled at 218 sites in 18 countries from October 2006 to May 2009. Patients were randomized in a double-blind, placebo-controlled, double-dummy design to receive either (i) placebo bolus and infusion or (ii) cangrelor 30 µg/kg bolus and 4 µg/kg/min infusion for the duration of PCI, with a minimum infusion duration of 2 hours and a maximum of 4 hours. Patients in the placebo arm of the trial received 600 mg of clopidogrel at the end of the procedure, while patients in the cangrelor arm received 600 mg of clopidogrel after the end of the cangrelor infusion (FIG. 1).

The inclusion criteria for the trial were as follows: age ≥18 years; diagnostic coronary angiography revealing atherosclerotic lesion(s) amenable to PCI with or without stent implantation; and evidence of either non-ST-segment elevation myocardial infarction or unstable angina. Stable angina was initially allowed at the beginning of the trial prior to a protocol amendment. The diagnosis of non-ST-segment elevation myocardial infarction required troponin I or T greater than the upper limit of normal within 24 hours of randomization (or if troponin results were unavailable at that time, creatine kinase-myocardial band isoenzyme [CK-MB] greater than the upper limit of normal). The diagnosis of unstable angina required ischemic chest discomfort occurring at rest and lasting >10 minutes within the 24 hours prior to randomization and dynamic electrocardiographic changes; age ≥65 years and/or diabetes mellitus were also required.

The exclusion criteria included the following: prior thienopyridine use in the past 7 days, planned staged PCI procedure where the second stage would occur <30 days after the first PCI, admission planned for <12 hours following PCI, ST-segment elevation myocardial infarction within 48 hours of randomization, known or suspected pregnancy, lactating females, increased bleeding risk (ischemic stroke within the last year or any previous hemorrhagic stroke), intracranial tumor, cerebral arteriovenous malformation, intracranial aneurysm, recent (<1 month) trauma or major surgery (including coronary artery bypass grafting), current warfarin use, active bleeding, known International Normalized Ratio>1.5, past or present bleeding disorder, platelet count <100,000/µL, severe hypertension (systolic blood pressure >180 mm Hg or diastolic blood pressure >110 mm Hg), fibrinolytic therapy or glycoprotein IIb/IIIa inhibitor use in the 12 hours preceding randomization.

The primary efficacy endpoint was the composite of death, myocardial infarction, or ischemia-driven revascularization at 48 hours. The primary analysis was performed on a modified intent-to-treat population. Confirmatory analyses were performed on an intent-to-treat population. Secondary endpoints included the individual rates of death, myocardial infarction, new Q-wave myocardial infarction, ischemia-driven revascularization, abrupt vessel closure, or stroke at 48 hours. Death at 30 days and 1 year was also recorded. The clinical events committee adjudicated myocardial infarction, Q-wave myocardial infarction, ischemia-driven revascularization, stent thromboses, and stroke (ischemic or hemorrhagic). The definition of stent thrombosis was similar to the Academic Research Consortium definition of definite stent thrombosis. After review of the prespecified analyses, two exploratory endpoints less reliant on periprocedural biomarker ascertainment were examined. The exploratory endpoints, which were composed of prespecified and adjudicated endpoints, were the composite of death, Q-wave myocardial infarction, or ischemia-driven revascularization and the composite of death, Q-wave myocardial infarction, or stent thrombosis. Bleeding and adverse events through 48 hours were compared.

Statistical analyses—All efficacy analyses were performed on the modified intent-to-treat population, defined as all randomized subjects who received at least one dose of study drug and underwent the index PCI. All safety-related analyses were performed on the safety population, which included all patients who received at least one dose of assigned study drug. Patients in the safety analyses were assigned to a treatment arm based on treatment actually received, not as randomized. Intent-to-treat analyses are also presented for full disclosure of results. All statistical tests were two-tailed using a level of significance of 0.05. The primary endpoint comparison between the cangrelor and placebo arms was performed by calculating an odds ratio (OR) with accompanying 95% confidence intervals (CI) using logistic regression. Logistic regression was also used to analyze the majority of the remaining secondary endpoints. The trial had 85% power to detect a 25% reduction in the primary endpoint, assuming a 7.7% event rate in the placebo arm, with a projected sample size of 6400 patients.

Figure 2:
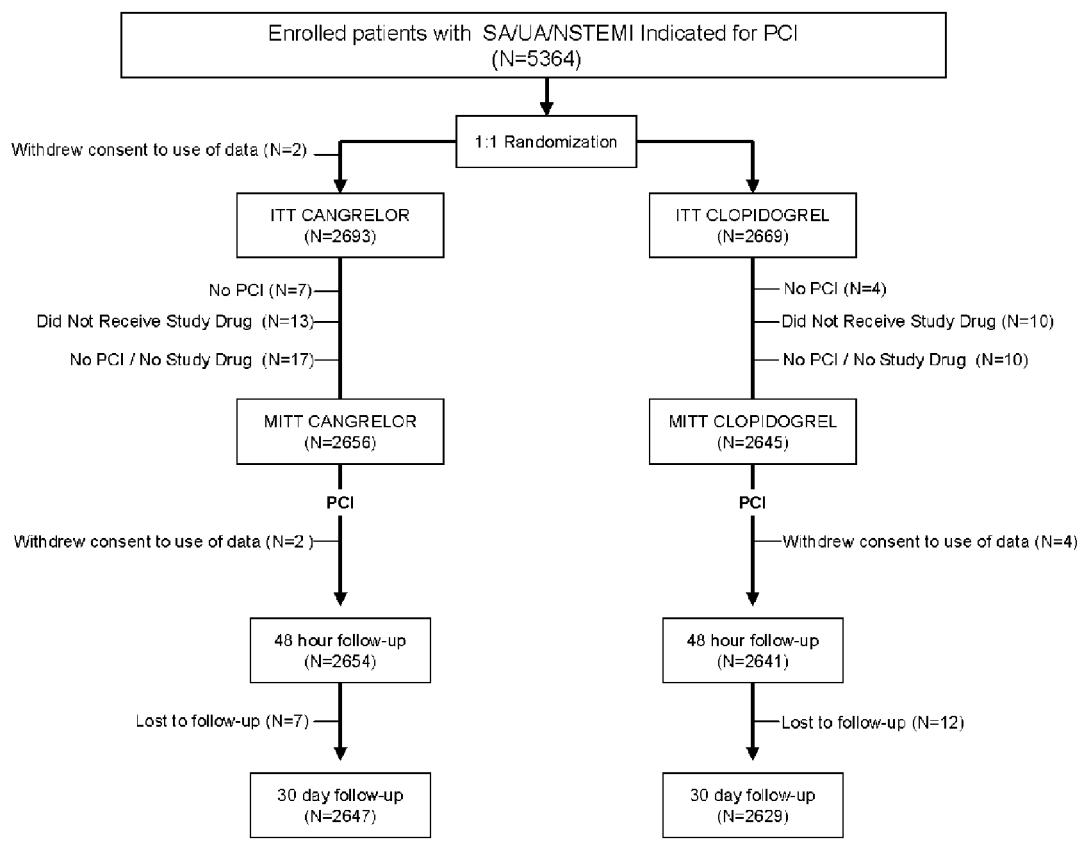
FIG. 2—diagram showing primary modified intent-to-treat analysis population.

A total of 5362 patients were included in the intent-to-treat population; of these, 5301 formed the primary modified intent-to-treat analysis population (FIG. 2). There were 61 patients who were not included because they did not receive study drug or undergo PCI. Baseline characteristics were well-matched in the two groups (Table 1).

TABLE 1

Baseline characteristics for ITT, MITT, and Safety populations

|  | ITT | | MITT |
|---|---|---|---|
|  | Cangrelor (N = 2693) | Clopidogrel (N = 2669) | Cangrelor (N = 2656) |
| Age, yrs | 63.0 (54.0, 71.0) | 63.0 (54.0, 71.0) | 63.0 (54.0, 71.0) |
| Sex, No. (%) | | | |
| Male | 1938 (72.0) | 1877 (70.3) | 1909 (71.9) |
| Female | 755 (28.0) | 792 (29.7) | 747 (28.1) |
| Race, No. (%) | | | |
| White | 2039 (76.0) | 2024 (76.0) | 2015 (76.1) |
| Asian | 482 (18.0) | 476 (17.9) | 475 (17.9) |
| Black | 80 (3.0) | 73 (2.7) | 75 (2.8) |
| Hispanic | 75 (2.8) | 85 (3.2) | 74 (2.8) |
| Other | 8 (0.3) | 5 (0.2) | 8 (0.3) |
| Weight, kg | 80.0 (70.0, 92.0) | 80.0 (70.0, 92.0) | 80.0 (70.0, 92.0) |
| Height, cm | 170.0 (163.0, 176.0) | 170.0 (163.0, 176.0) | 170.0 (163.0, 176.0) |
| Stable angina, No. (%) | 145 (5.4) | 142 (5.3) | 139 (5.2) |
| Unstable angina, No. (%) | 949 (35.2) | 918 (34.4) | 939 (35.4) |
| NSTEMI, No. (%) | 1599 (59.4) | 1609 (60.3) | 1578 (59.4) |
| Medical history, No. (%) | | | |
| Diabetes mellitus | 828 (30.8) | 868 (32.6) | 812 (30.6) |
| Current smoker | 850 (31.8) | 806 (30.4) | 842 (31.9) |
| Hypertension | 1994 (74.3) | 1979 (74.5) | 1972 (74.5) |
| Hyperlipidemia | 1342 (53.5) | 1347 (54.0) | 1324 (53.6) |
| Stroke/TIA | 162 (6.0) | 160 (6.0) | 159 (6.0) |
| Family history of CAD | 918 (36.4) | 901 (36.0) | 902 (36.2) |
| MI | 645 (24.1) | 683 (25.7) | 640 (24.2) |
| PTCA/PCI | 381 (14.2) | 411 (15.5) | 374 (14.1) |
| CABG | 203 (7.5) | 223 (8.4) | 199 (7.5) |
| Congestive HF | 210 (7.8) | 192 (7.2) | 206 (7.8) |
| PAD | 126 (4.8) | 143 (5.5) | 122 (4.7) |
| Periprocedural medications, No (%) | | | |
| Bivalirudin | 565 (21.0) | 561 (21.0) | 559 (21.0) |
| UFH | 1714 (63.7) | 1709 (64.1) | 1699 (64.0) |
| LMWH | 487 (18.1) | 501 (18.8) | 481 (18.1) |
| GP IIb/IIIa | 245 (9.1) | 247 (9.3) | 241 (9.1) |
| Study treatment | | | |
| Number of target vessels, No. (%) | | | |
| 1 | 2231 (83.7) | 2211 (83.3) | 2218 (83.6) |
| 2 | 414 (15.5) | 412 (15.5) | 414 (15.6) |
| 3 | 19 (0.7) | 29 (1.1) | 19 (0.7) |
| Drug-eluting stent, No. (%) | 1037 (38.9) | 1023 (38.6) | 1033 (38.9) |
| Non-drug-eluting stent, No. (%) | 1514 (56.8) | 1515 (57.1) | 1509 (56.9) |

TABLE 1-continued

Baseline characteristics for ITT, MITT, and Safety populations

| | | | |
|---|---|---|---|
| Angiographic complications (site reported) | | | |
| Threatened abrupt closure | 10 (0.4) | 9 (0.3) | 10 (0.4) |
| Unsuccessful procedure | 84 (3.1) | 97 (3.7) | 81 (3.1) |
| Abrupt vessel closure | 13 (0.5) | 16 (0.6) | 13 (0.5) |
| New thrombus or suspected thrombus | 14 (0.5) | 15 (0.6) | 14 (0.5) |
| Acute stent thrombosis | 1 (0.0) | 5 (0.2) | 1 (0.0) |
| Need for urgent CABG | 5 (0.2) | 4 (0.2) | 5 (0.2) |
| IV study drug administered, No. (%) | 2663 (98.9) | 2649 (99.3) | 2656 (100.0) |
| Bolus administered, No. (%) | 2663 (98.9) | 2649 (99.3) | 2656 (100.0) |
| Infusion administered, No. (%) | 2659 (98.7) | 2649 (99.3) | 2654 (99.9) |
| Duration of infusion, hrs | 2.1 (2.0, 2.3) | 2.1 (2.0, 2.3) | 2.1 (2.0, 2.3) |
| Oral study drug administered, No. (%) | 2630 (97.7) | 2626 (98.4) | 2629 (99.0) |

| | MITT | Safety | |
|---|---|---|---|
| | Clopidogrel (N = 2645) | Cangrelor (N = 2662) | Clopidogrel (N = 2650) |
| Age, yrs | 63.0 (54.0, 71.0) | 63.0 (54.0, 71.0) | 63.0 (54.0, 71.0) |
| Sex, No. (%) | | | |
| Male | 1863 (70.4) | 1915 (71.9) | 1866 (70.4) |
| Female | 782 (29.6) | 747 (28.1) | 784 (29.6) |
| Race, No. (%) | | | |
| White | 2006 (76.0) | 2017 (76.0) | 2009 (76.0) |
| Asian | 473 (17.9) | 477 (18.0) | 474 (17.9) |
| Black | 72 (2.7) | 76 (2.9) | 73 (2.8) |
| Hispanic | 84 (3.2) | 75 (2.8) | 84 (3.2) |
| Other | 5 (0.2) | 8 (0.3) | 5 (0.2) |
| Weight, kg | 80.0 (70.0, 92.0) | 80.0 (70.0, 92.0) | 80.0 (70.0, 92.0) |
| Height, cm | 170.0 (163.0, 176.0) | 170.0 (163.0, 176.0) | 170.0 (163.0, 176.0) |
| Stable angina, No. (%) | 140 (5.3) | 138 (5.2) | 141 (5.3) |
| Unstable angina, No. (%) | 909 (34.4) | 940 (35.3) | 911 (34.4) |
| NSTEMI, No. (%) | 1596 (60.3) | 1584 (59.5) | 1598 (60.3) |
| Medical history, No. (%) | | | |
| Diabetes mellitus | 862 (32.6) | 815 (30.6) | 862 (32.6) |
| Current smoker | 799 (30.4) | 845 (31.9) | 799 (30.3) |
| Hypertension | 1962 (74.5) | 1974 (74.4) | 1966 (74.5) |
| Hyperlipidemia | 1332 (53.9) | 1325 (53.5) | 1335 (53.9) |
| Stroke/TIA | 158 (6.0) | 160 (6.0) | 158 (6.0) |
| Family history of CAD | 890 (35.9) | 907 (36.4) | 891 (35.9) |
| MI | 679 (25.8) | 641 (24.2) | 680 (25.7) |
| PTCA/PCI | 409 (15.5) | 377 (14.2) | 409 (15.5) |
| CABG | 221 (8.4) | 200 (7.5) | 221 (8.3) |
| Congestive HF | 191 (7.2) | 208 (7.8) | 191 (7.2) |
| PAD | 142 (5.5) | 124 (4.8) | 142 (5.5) |
| Periprocedural medications, No (%) | | | |
| Bivalirudin | 555 (21.0) | 561 (21.1) | 556 (21.0) |
| UFH | 1695 (64.1) | 1701 (63.9) | 1699 (64.1) |
| LMWH | 497 (18.8) | 484 (18.2) | 497 (18.8) |
| GP IIb/IIIa | 244 (9.2) | 242 (9.1) | 244 (9.2) |
| Study treatment | | | |
| Number of target vessels, No. (%) | | | |
| 1 | 2201 (83.3) | 2217 (83.6) | 2202 (83.3) |
| 2 | 412 (15.6) | 414 (15.6) | 412 (15.6) |
| 3 | 29 (1.1) | 19 (0.7) | 29 (1.1) |
| Drug-eluting stent, No. (%) | 1021 (38.6) | 1032 (38.9) | 1022 (38.7) |
| Non-drug-eluting stent, No. (%) | 1510 (57.1) | 1509 (56.9) | 1510 (57.1) |
| Angiographic complications (site reported) | | | |
| Threatened abrupt closure | 9 (0.3) | 10 (0.4) | 9 (0.3) |
| Unsuccessful procedure | 95 (3.6) | 81 (3.1) | 95 (3.6) |
| Abrupt vessel closure | 16 (0.6) | 13 (0.5) | 16 (0.6) |
| New thrombus or suspected thrombus | 15 (0.6) | 14 (0.5) | 15 (0.6) |
| Acute stent thrombosis | 5 (0.2) | 1 (0.0) | 5 (0.2) |
| Need for urgent CABG | 3 (0.1) | 5 (0.2) | 3 (0.1) |

TABLE 1-continued

Baseline characteristics for ITT, MITT, and Safety populations

| | | | |
|---|---|---|---|
| IV study drug administered, No. (%) | 2645 (100.0) | 2662 (100.0) | 2650 (100.0) |
| Bolus administered, No. (%) | 2645 (100.0) | 2662 (100.0) | 2650 (100.0) |
| Infusion administered, No. (%) | 2645 (100.0) | 2658 (99.8) | 2650 (100.0) |
| Duration of infusion, hrs | 2.1 (2.0, 2.3) | 2.1 (2.0, 2.3) | 2.1 (2.0, 2.3) |
| Oral study drug administered, No. (%) | 2625 (99.2) | 2629 (98.8) | 2627 (99.1) |

Variables are presented as median (25th, 75th) unless otherwise indicated. CABG denotes coronary artery bypass grafting; CAD, coronary artery disease; GP, glycoprotein; HF, heart failure; ITT, intent to treat; IV, intravenous; LMWH, low molecular weight heparin; MI, myocardial infarction; MITT, modified intent to treat; NSTEMI, non-ST-segment elevation myocardial infarction; PAD, peripheral artery disease; PCI, percutaneous coronary intervention; PTCA, percutaneous transluminal coronary angioplasty; TIA, transient ischemic attack; UFH, unfractionated heparin.

Figure 3A:
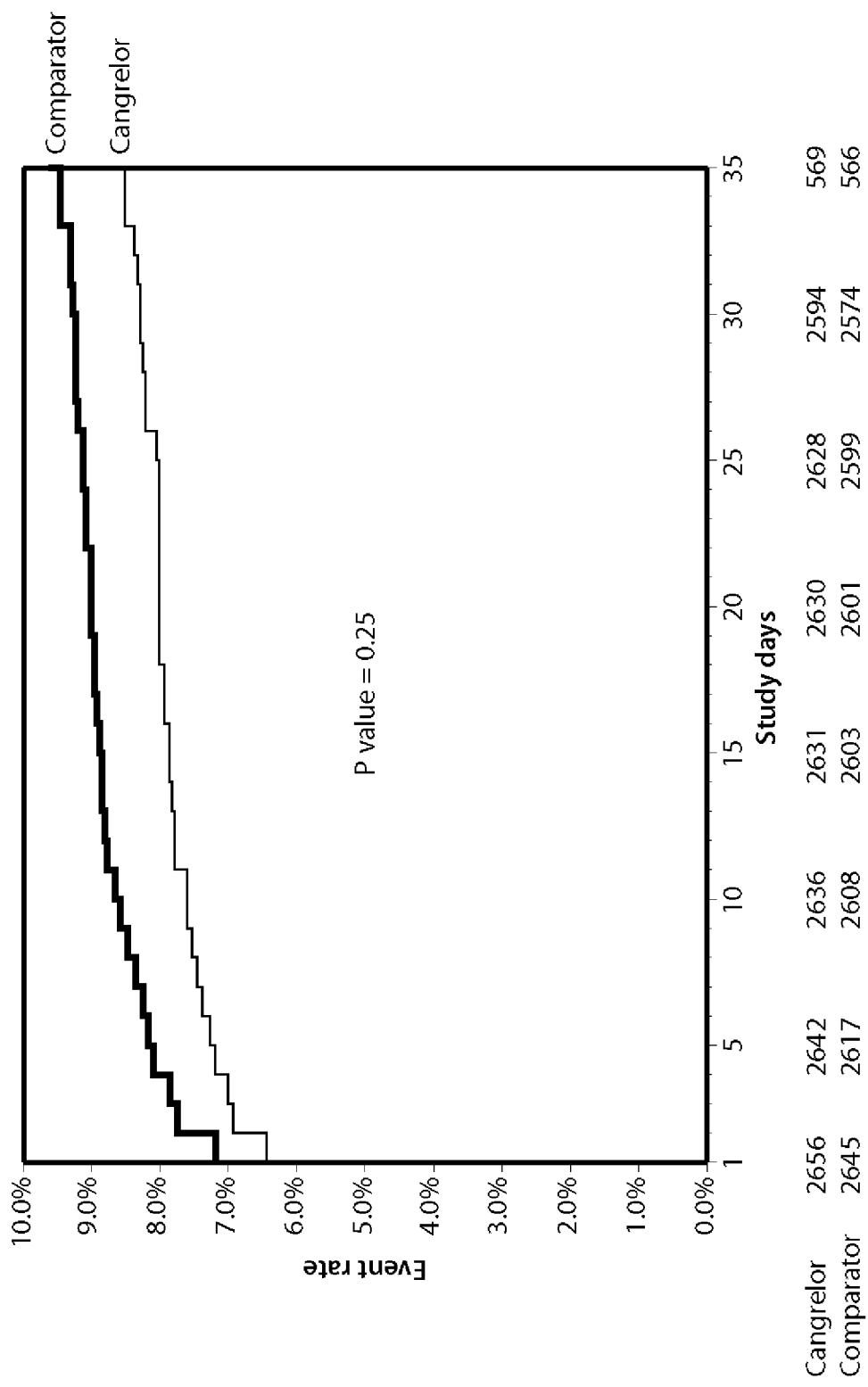
FIGS. 3A, 3B and 3C—landmark analysis of Kaplan-Meier curves for the primary efficacy endpoint (FIG. 3A), stent thrombosis (FIG. 3B), and mortality at 48 hours and 30 days (FIG. 3C).

The majority of patients were enrolled with non-ST-segment elevation myocardial infarction (59.8%). During PCI, unfractionated heparin was the most frequently used antithrombin (63.9%) and glycoprotein IIb/IIIa inhibitors were used sparingly (9.2%). Drug-eluting stents were used less often than bare metal stents (38.7% vs 56.9%). The time from hospital admission to PCI was short (median of 7.9 hours [3.3, 24.1]). The primary endpoint occurred in 7.0% of patients receiving cangrelor and 8.0% of patients receiving placebo (OR 0.87, 95% CI 0.71-1.07; P=0.17) (Table 2, FIG. 3A).

TABLE 2

48-hour endpoints for MITT, ITT, and Safety Populations

| MITT | | | | |
|---|---|---|---|---|
| | Cangrelor (N = 2656) | Clopidogrel (N = 2645) | OR (95% CI) | P Value |
| Adjudicated endpoints | | | | |
| Death/MI/IDR (primary endpoint) | 185 (7.0) | 210 (8.0) | 0.867 (0.706, 1.065) | 0.1746 |
| MI | 177 (6.7) | 191 (7.2) | 0.917 (0.742, 1.133) | 0.4207 |
| IDR | 19 (0.7) | 24 (0.9) | 0.786 (0.430, 1.439) | 0.4354 |
| All-cause mortality | 6 (0.2) | 18 (0.7) | 0.330 (0.131, 0.833) | 0.0190 |
| Stroke | 7 (0.3) | 5 (0.2) | 1.394 (0.442, 4.398) | 0.5708 |
| Stent thrombosis | 5 (0.2) | 16 (0.6) | 0.310 (0.113, 0.847) | 0.0223 |
| Q-wave MI | 4 (0.2) | 8 (0.3) | 0.497 (0.149, 1.652) | 0.2538 |
| Exploratory endpoints | | | | |
| Death/Q-wave MI/IDR | 23 (0.9) | 41 (1.6) | 0.554 (0.332, 0.926) | 0.0243 |
| Death/Q-wave MI/Stent thrombosis | 13 (0.5) | 34 (1.3) | 0.377 (0.199, 0.717) | 0.0029 |

| ITT | | | | |
|---|---|---|---|---|
| | Cangrelor (N = 2693) | Clopidogrel (N = 2669) | OR (95% CI) | P Value |
| Adjudicated endpoints | | | | |
| Death/MI/IDR | 187 (6.9) | 213 (8.0) | 0.859 (0.701, 1.054) | 0.1456 |
| MI | 177 (6.6) | 192 (7.2) | 0.906 (0.734, 1.120) | 0.3632 |
| IDR | 19 (0.7) | 26 (1.0) | 0.721 (0.398, 1.307) | 0.2814 |
| All-cause mortality | 8 (0.3) | 19 (0.7) | 0.415 (0.181, 0.950) | 0.0374 |
| Stroke | 7 (0.3) | 6 (0.2) | 1.155 (0.388, 3.442) | 0.7954 |
| Stent thrombosis | 5 (0.2) | 16 (0.6) | 0.308 (0.113, 0.842) | 0.0218 |
| Q-wave MI | 4 (0.1) | 9 (0.3) | 0.439 (0.135, 1.428) | 0.1713 |
| Exploratory endpoints | | | | |
| Death/Q-wave MI/IDR | 25 (0.9) | 44 (1.7) | 0.558 (0.341, 0.915) | 0.0207 |
| Death/Q-wave MI/Stent thrombosis | 15 (0.6) | 36 (1.4) | 0.409 (0.224, 0.749) | 0.0038 |

| Safety | | | | |
|---|---|---|---|---|
| | Cangrelor (N = 2662) | Clopidogrel (N = 2650) | OR (95% CI) | P Value |
| Adjudicated endpoints | | | | |
| Death/MI/IDR | 185 (7.0) | 212 (8.0) | 0.858 (0.699, 1.053) | 0.1436 |
| MI | 176 (6.6) | 193 (7.3) | 0.901 (0.729, 1.113) | 0.3322 |
| IDR | 19 (0.7) | 25 (0.9) | 0.754 (0.414, 1.373) | 0.3561 |
| All-cause mortality | 7 (0.3) | 18 (0.7) | 0.385 (0.161, 0.924) | 0.0326 |
| Stroke | 7 (0.3) | 5 (0.2) | 1.394 (0.442, 4.396) | 0.5712 |
| Stent thrombosis | 5 (0.2) | 16 (0.6) | 0.310 (0.113, 0.846) | 0.0223 |
| Q-wave MI | 4 (0.2) | 9 (0.3) | 0.441 (0.136, 1.435) | 0.1738 |

TABLE 2-continued 48-hour endpoints for MITT, ITT, and Safety Populations

Exploratory endpoints

| | | | | |
|---|---|---|---|---|
| Death/Q-wave MI/IDR | 24 (0.9) | 42 (1.6) | 0.564 (0.341, 0.935) | 0.0263 |
| Death/Q-wave MI/Stent thrombosis | 14 (0.5) | 35 (1.3) | 0.395 (0.212, 0.735) | 0.0034 |

Figure 3B:
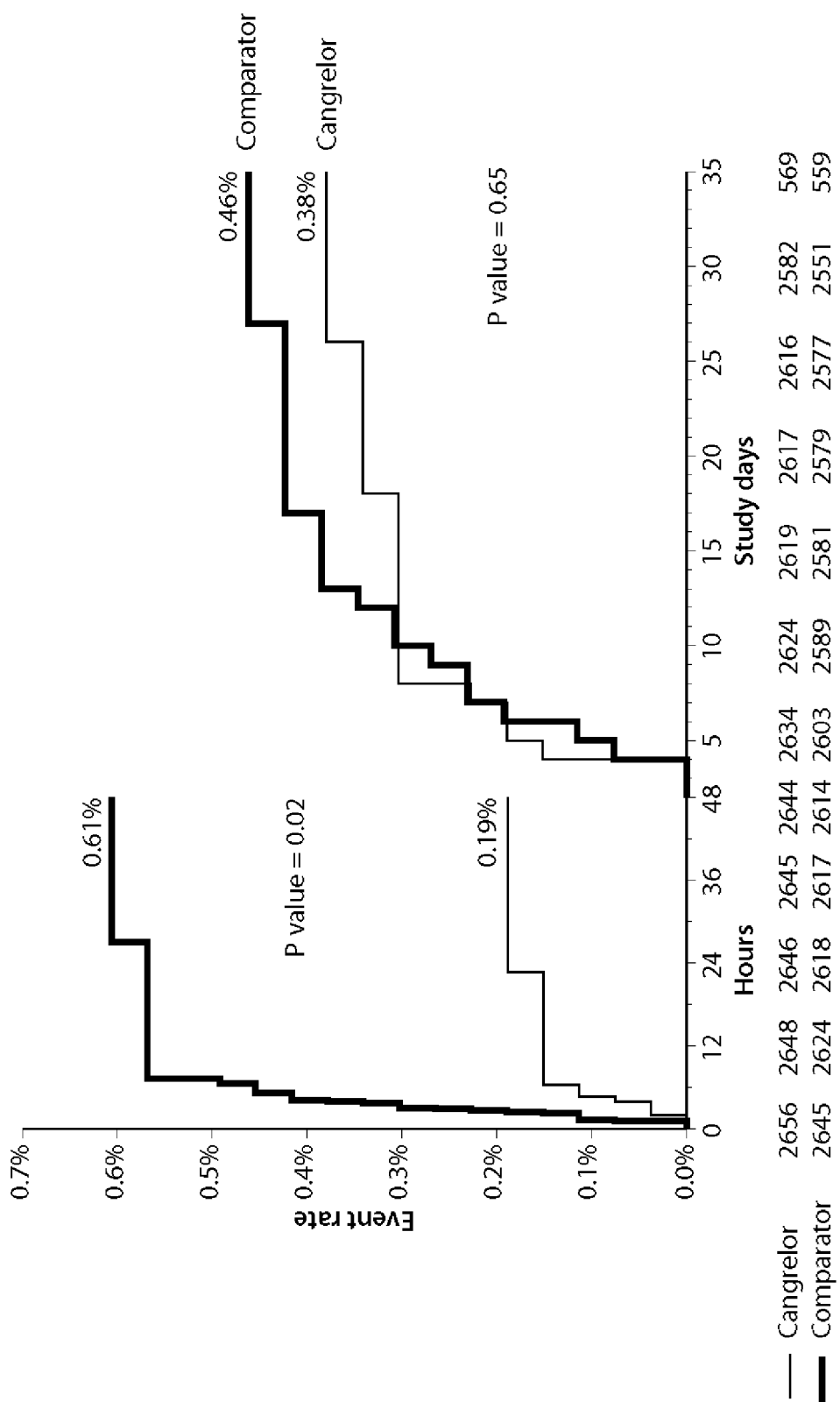
Figure 3C:
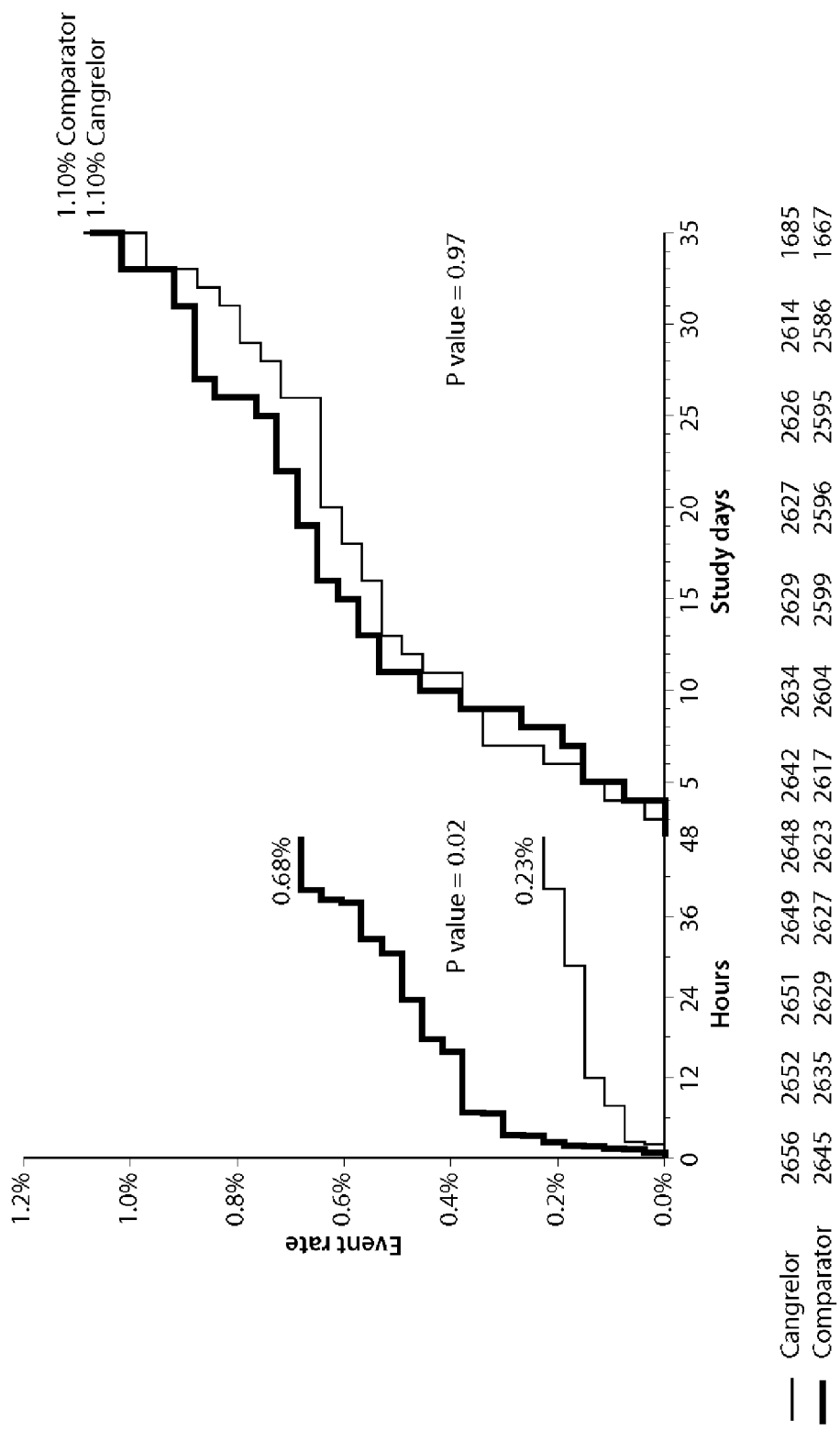

There was no significant difference in overall myocardial infarction, Q-wave myocardial infarction, or ischemia-driven revascularization (Table 2). Rates of stent thrombosis were significantly lower with cangrelor (0.2% vs 0.6% [OR 0.31, 95% CI 0.11-0.85; P=0.022]) (FIG. 3B). The rate of mortality at 48 hours was significantly lower in the cangrelor arm (0.2% vs 0.7% [OR 0.33, 95% CI 0.13-0.83; P=0.019]), though by 30 days, this difference was no longer significant (Table 3, FIG. 3C).

TABLE 3

30-day endpoints for ITT, MITT, and Safety Populations

| | ITT | | | |
|---|---|---|---|---|
| | Cangrelor (N = 2693) | Clopidogrel (N = 2669) | OR (95% CI) | P Value |
| Adjudicated endpoints | | | | |
| Death/MI/IDR | 230 (8.6) | 254 (9.6) | 0.885 (0.734, 1.067) | 0.1999 |
| MI | 190 (7.1) | 202 (7.6) | 0.924 (0.752, 1.135) | 0.4515 |
| IDR | 37 (1.4) | 49 (1.8) | 0.743 (0.483, 1.142) | 0.1752 |
| All-cause mortality | 36 (1.3) | 47 (1.8) | 0.754 (0.487, 1.167) | 0.2048 |
| Stent thrombosis | 15 (0.6) | 29 (1.1) | 0.508 (0.272, 0.950) | 0.0340 |
| Q-wave MI | 8 (0.3) | 15 (0.6) | 0.526 (0.222, 1.242) | 0.1425 |
| Exploratory endpoints | | | | |
| Death/Q-wave MI/IDR | 69 (2.6) | 94 (3.5) | 0.718 (0.524, 0.984) | 0.0396 |
| Death/Q-wave MI/Stent thrombosis | 51 (1.9) | 77 (2.9) | 0.648 (0.453, 0.927) | 0.0174 |

| | MITT | | | |
|---|---|---|---|---|
| | Cangrelor (N = 2656) | Clopidogrel (N = 2645) | OR (95% CI) | P Value |
| Adjudicated endpoints | | | | |
| Death/MI/IDR | 226 (8.5) | 249 (9.5) | 0.892 (0.739, 1.078) | 0.2365 |
| MI | 189 (7.1) | 201 (7.6) | 0.929 (0.756, 1.142) | 0.4831 |
| IDR | 37 (1.4) | 46 (1.7) | 0.796 (0.515, 1.231) | 0.3054 |
| All-cause mortality | 33 (1.2) | 45 (1.7) | 0.725 (0.461, 1.140) | 0.1635 |
| Stent thrombosis | 15 (0.6) | 28 (1.1) | 0.529 (0.282, 0.993) | 0.0477 |
| Q-wave MI | 8 (0.3) | 14 (0.5) | 0.566 (0.237, 1.352) | 0.2003 |
| Exploratory endpoints | | | | |
| Death/Q-wave MI/IDR | 66 (2.5) | 89 (3.4) | 0.730 (0.528, 1.008) | 0.0560 |
| Death/Q-wave MI/Stent thrombosis | 48 (1.8) | 73 (2.8) | 0.647 (0.447, 0.935) | 0.0203 |

| | Safety | | | |
|---|---|---|---|---|
| | Cangrelor (N = 2662) | Clopidogrel (N = 2650) | OR (95% CI) | P Value |
| Adjudicated endpoints | | | | |
| Death/MI/IDR | 226 (8.5) | 251 (9.5) | 0.884 (0.732, 1.067) | 0.1999 |
| MI | 188 (7.1) | 203 (7.7) | 0.913 (0.743, 1.122) | 0.3887 |
| IDR | 37 (1.4) | 47 (1.8) | 0.779 (0.504, 1.202) | 0.2584 |
| All-cause mortality | 34 (1.3) | 45 (1.7) | 0.747 (0.477, 1.170) | 0.2024 |
| Stent thrombosis | 15 (0.6) | 28 (1.1) | 0.529 (0.282, 0.993) | 0.0475 |
| Q-wave MI | 8 (0.3) | 15 (0.6) | 0.528 (0.224, 1.248) | 0.1455 |

TABLE 3-continued

| 30-day endpoints for ITT, MITT, and Safety Populations | | | | |
|---|---|---|---|---|
| Exploratory endpoints | | | | |
| Death/Q-wave MI/IDR | 67 (2.5) | 90 (3.4) | 0.732 (0.531, 1.010) | 0.0572 |
| Death/Q-wave MI/Stent thrombosis | 49 (1.8) | 74 (2.8) | 0.651 (0.452, 0.938) | 0.0212 |

Variables are presented as no. (%) unless otherwise indicated.
CI denotes confidence interval;
IDR, ischemia-driven revascularization;
ITT, intent to treat;
MI, myocardial infarction;
MITT, modified intent to treat;
OR, odds ratio.

Somewhat counterintuitively, in the subgroup of 1659 patients enrolled without baseline troponin elevation, the primary efficacy endpoint was reduced with cangrelor from 7.2% to 4.6% (OR 0.62, 95% CI 0.41, 0.95; P=0.0266).

Therefore, exploratory analyses were performed in the overall study population examining the following two clinical endpoints: death, Q-wave myocardial infarction, or stent thrombosis; and death, Q-wave myocardial infarction, or ischemia-driven revascularization. These endpoints were significantly reduced in favor of cangrelor.

The rates of Thrombolysis in Myocardial Infarction (TIMI) major or minor or Global Utilization of Streptokinase and Tissue Plasminogen Activator for Occluded Coronary Arteries (GUSTO) severe or moderate bleeding were not significantly different between the groups, though the rates of Acute Catheterization and Urgent Intervention Triage Strategy (ACUITY) major and minor bleeding and of GUSTO mild bleeding were significantly higher with cangrelor (Table 4).

TABLE 4

| | | | | |
|---|---|---|---|---|
| 48-hour bleeding events for safety population | | | | |
| Bleeding Events | Cangrelor (N = 2662) | Placebo (N = 2650) | Odds Ratio (95% CI) | P Value |
| Access site bleeding requiring radiologic or surgical intervention | 8 (0.3) | 10 (0.4) | 0.796 (0.314, 2.019) | 0.6307 |
| Hematoma ≥5 cm at puncture site | 115 (4.3) | 71 (2.7) | 1.640 (1.214, 2.216) | 0.0013 |
| Intracranial hemorrhage | 2 (0.1) | 1 (0.0) | 1.992 (0.180, 21.978) | 0.5738 |
| Intraocular | 0 (0.0) | 0 (0.0) | | |
| Reoperation for bleeding | 1 (0.0) | 1 (0.0) | 0.995 (0.062, 15.924) | 0.9975 |
| Retroperitoneal | 2 (0.1) | 1 (0.0) | 1.992 (0.180, 21.978) | 0.5738 |
| Ecchymosis | 95 (3.6) | 57 (2.2) | 1.684 (1.207, 2.349) | 0.0022 |
| Epistaxis | 6 (0.2) | 12 (0.5) | 0.497 (0.186, 1.325) | 0.1622 |
| Hematoma <5 cm at puncture site | 150 (5.6) | 119 (4.5) | 1.270 (0.992, 1.626) | 0.0577 |
| Oozing at puncture site | 125 (4.7) | 91 (3.4) | 1.385 (1.052, 1.825) | 0.0204 |
| Thrombocytopenia | 2 (0.1) | 3 (0.1) | 0.663 (0.111, 3.973) | 0.6532 |
| Hemodynamic compromise | 7 (0.3) | 5 (0.2) | 1.395 (0.442, 4.400) | 0.5704 |
| Any blood transfusion | 26 (1.0) | 16 (0.6) | 1.624 (0.869, 3.034) | 0.1285 |
| Any platelet transfusion | 4 (0.2) | 2 (0.1) | 1.992 (0.365, 10.887) | 0.4263 |
| Any red blood cell transfusion | 25 (0.9) | 15 (0.6) | 1.665 (0.876, 3.166) | 0.1197 |
| Drop in hemoglobin and/or hematocrit | 33 (1.2) | 35 (1.3) | 0.938 (0.581, 1.514) | 0.7927 |
| Bleed scoring criteria | | | | |
| ACUITY criteria | | | | |
| Minor bleeding | 320 (12.0) | 246 (9.3) | 1.335 (1.120, 1.592) | 0.0013 |
| Major bleeding | 147 (5.5) | 93 (3.5) | 1.607 (1.232, 2.096) | 0.0005 |
| GUSTO criteria | | | | |
| Mild bleeding | 427 (16.0) | 310 (11.7) | 1.442 (1.232, 1.688) | <.0001 |
| Moderate bleeding | 20 (0.8) | 13 (0.5) | 1.536 (0.762, 3.093) | 0.2300 |
| Severe/life-threatening bleeding | 9 (0.3) | 6 (0.2) | 1.495 (0.531, 4.205) | 0.4462 |
| TIMI criteria | | | | |
| Minor bleeding | 22 (0.8) | 16 (0.6) | 1.372 (0.719, 2.618) | 0.3376 |
| Major bleeding | 4 (0.2) | 9 (0.3) | 0.442 (0.136, 1.436) | 0.1742 |

Variables are presented as no. (%) unless otherwise indicated.
The bleeding options under each criterion are not mutually exclusive. For example, a patient may have a clinically significant bleed and a minor bleed based on the ACUITY criteria, if more than 1 bleed is present. Each patient was counted only once for each criteria level, regardless of the number of bleeds identified under each criterion. Bleeding listed here included CABG-related bleeding.

Figure 4:
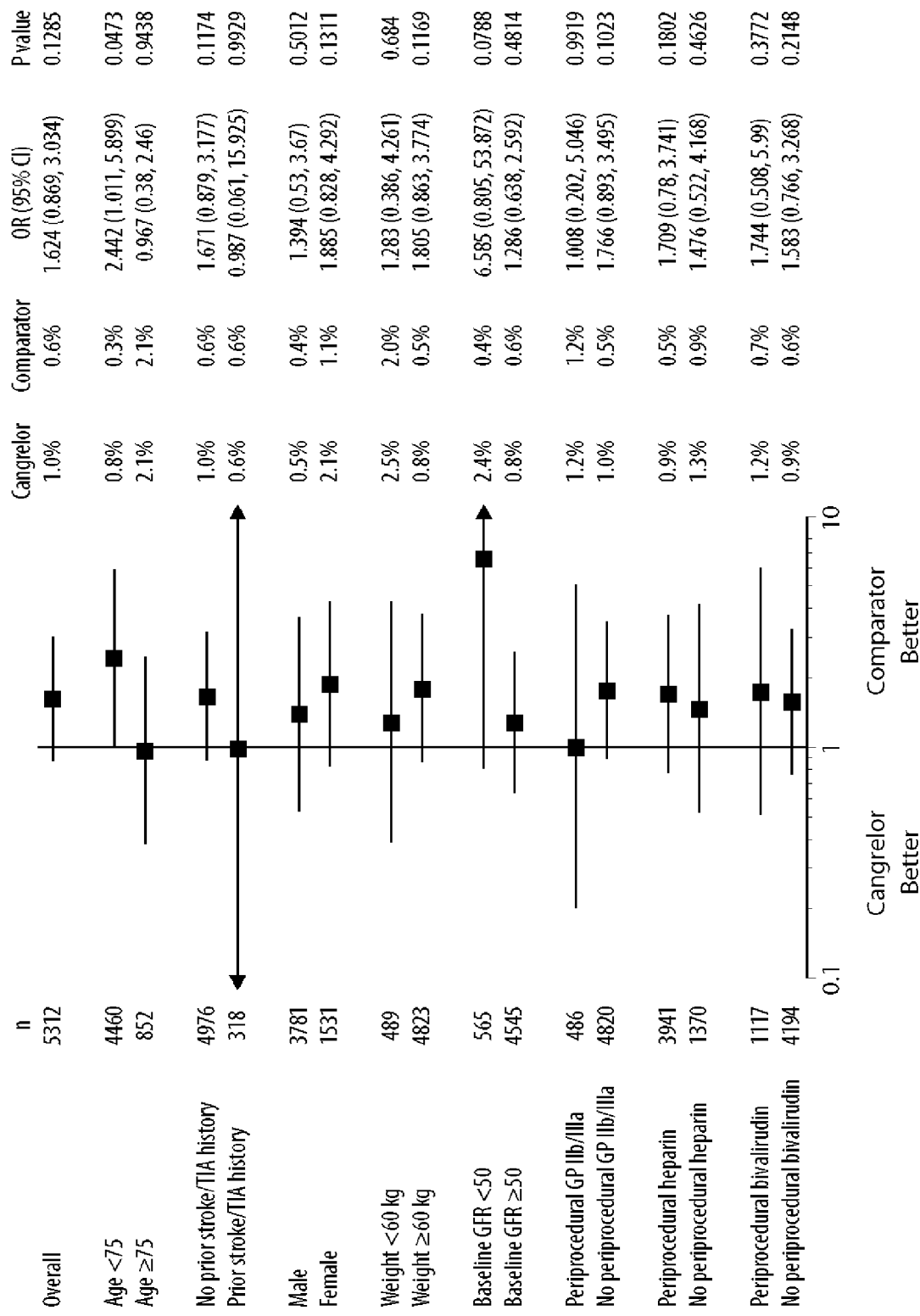
FIG. 4—diagram showing transfusion rates for all patients (including coronary artery bypass graft) in subgroups at high risk of bleeding.

The difference in ACUITY major bleeding was due to an excess of groin hematomas, but not more serious forms of bleeding. The rates of red blood cell transfusion were not significantly different (0.9% with cangrelor vs 0.6% with placebo; P=0.12). Notably, patients at higher risk of bleeding, such as the elderly or those with prior stroke or transient ischemic attack, did not have a higher rate of transfusion with cangrelor (FIG. 4). There was no difference in the rate of arrhythmia (2.3% vs 2.4%; P=0.7664) and the incidence of dyspnea was higher with cangrelor (1.4% [37] vs 0.5% [14]; P=0.0019).

The results demonstrate that important prespecified endpoints, including stent thrombosis and mortality, were significantly reduced by cangrelor.

Example 2—Platelet Inhibition with Cangrelor in Patients with Acute Coronary Syndromes Undergoing Percutaneous Coronary Intervention In this example, the efficacy of cangrelor versus clopidogrel was examined when administered to patients before percutaneous coronary intervention (PCI).

Patients were eligible for enrollment if they had stable angina, unstable angina, or non-ST-segment elevation (NSTE) MI with obstructive coronary artery disease and were scheduled to undergo PCI. An additional 1000 patients with STEMI for whom primary PCI was planned were also eligible. A protocol amendment issued in May 2007 required that patients have definite features of an acute coronary syndrome (either STEMI undergoing planned primary PCI or a NSTE acute coronary syndrome with positive cardiac biomarkers or chest pain with dynamic electrocardiographic changes in patients ≥65 years or with diabetes). Patients could not have received fibrinolysis or glycoprotein IIb/IIIa inhibitors within the prior 12 hours or clopidogrel >75 mg/day in the prior 5 days.

Figure 5:
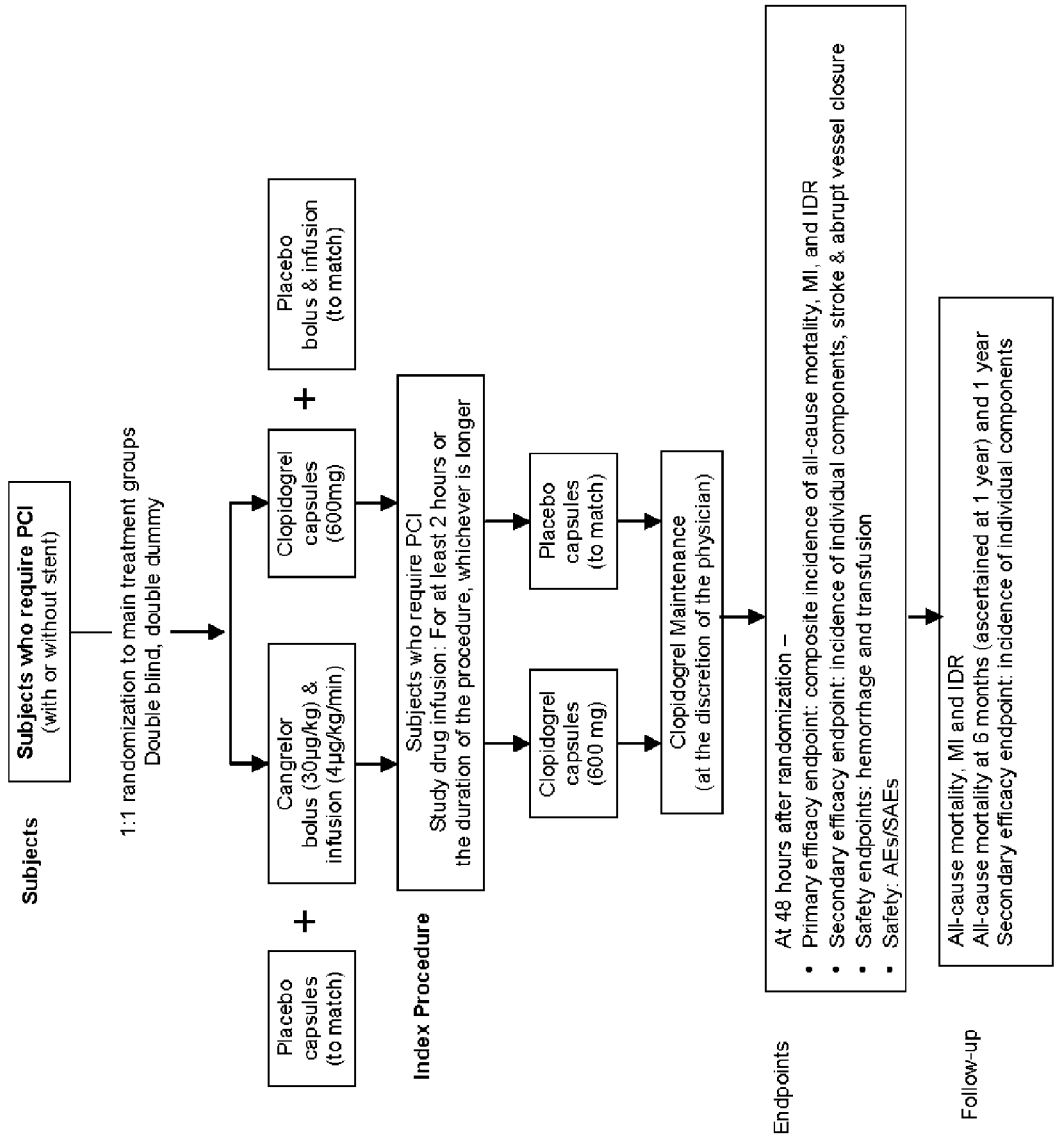
FIG. 5—diagram showing trial design for the study of the efficacy of cangrelor versus placebo administered to patients before percutaneous coronary intervention (PCI).

Patients were randomized in a 1:1 double-blind, double-dummy fashion using an IVRS system to either cangrelor or clopidogrel. All patients received a 30 µg/kg intravenous bolus of cangrelor or placebo followed by a 4 µg/kg/min intravenous infusion (FIG. 5). The infusion began within 30 minutes prior to PCI and continued for at least 2 hours or until the conclusion of the index procedure, whichever was longer. At the treating physician's discretion, the infusion could be continued for 4 hours. Patients received 600 mg encapsulated clopidogrel (four 150 mg capsules) or placebo at the time of infusion. To allow the transition from intravenous cangrelor to oral clopidogrel, patients ingested another four capsules (clopidogrel for cangrelor patients, placebo for clopidogrel patients) at the cessation of study drug infusion. The duration of daily clopidogrel following the procedure was left to the discretion of the treating physician, though additional clopidogrel beyond the pre-scribed study medication was not allowed until the day following the index procedure.

All patients received aspirin 75-325 mg per local site standards. Adjunctive anticoagulants (unfractionated heparin, low molecular weight heparin, bivalirudin, or fonda-parinux) and the procedural use of glycoprotein IIb/IIIa inhibitors were determined by the treating physician.

The primary efficacy endpoint was the 48-hour composite of all-cause mortality, MI, or ischemia-driven revascularization. Prespecified secondary efficacy endpoints included the composite of mortality or MI at 48 hours and 30 days; the composite of mortality, MI, or ischemia-driven revascularization at 30 days; the components of the composite endpoints at 48 hours and 30 days; stroke at 48 hours; abrupt closure, threatened abrupt closure, need for urgent coronary artery bypass grafting, or unsuccessful procedure during the index PCI; acute (24 hours) and subacute (48 hours) stent thrombosis; and all-cause mortality at 6 months and 1 year.

Rates of MI and ischemia-driven revascularization up to 30 days following the index procedure were assessed. Ischemia-driven revascularization was defined as symptoms of myocardial ischemia leading to urgent (within 24 hours of the last episode of ischemia) revascularization, which must have occurred after the index procedure concluded (ie, guidewire removal). New electrocardiographic changes, acute pulmonary edema, ventricular arrhythmias, or hemodynamic instability could also constitute evidence of ischemia.

MI was defined by a new Q wave (duration >0.03 seconds) in two contiguous electrocardiographic leads or elevations in creatine kinase (CK) and CK-MB, including a rise of CK-MB≥3 times the local upper limit or normal and, when biomarkers were elevated prior to PCI, an additional 50% above baseline (Thygesen K. et al, *Circulation* 116: 2634-53 (2007)). One baseline troponin measurement was required for patients undergoing urgent PCI. Measurements of CK-MB were obtained at 2, 10, 17, and 24 hours post-PCI. Stent thrombosis was defined using Academic Research Consortium criteria (Cutlip D. E. et al., *Circulation* 115:2344-51 (2007)).

Bleeding was assessed up to 48 hours using clinical and laboratory definitions. Multiple definitions of bleeding were used for full disclosure of bleeding risks associated with cangrelor: (1) The Global Utilization of Streptokinase and Tissue Plasminogen Activator for Occluded Coronary Arteries (GUSTO) criteria (The GUSTO Investigators. *N Engl J Med* 329:673-82 (1993); mild, moderate, or severe/life-threatening based on transfusion use and presence/absence of hemodynamic compromise); (2) Thrombolysis in Myocardial Infarction (TIMI) criteria (Chesebro J. H. et al., *Circulation* 76:142-54 (1987); minor or major bleeding based on clinical and laboratory findings); (3) Acute Catheterization and Urgent Intervention Triage Strategy (ACUITY) criteria (Stone G. W. et al., *N Engl J Med* 355:2203-16 (2006); using detailed clinical assessment, changes in hemoglobin, hematomas >5 cm, and need for blood transfusion). Investigators reported adverse and serious adverse events according to International Conference on Harmonization guidance (International Conference on Harmonization (ICH) Guidance Documents. U.S. Food and Drug Administration Web site. (Accessed on Oct. 8, 2009, at the FDA website beginning with "www." and ending with "fda.gov/RegulatoryInformation/Guidances/ucm122049.htm")).

An independent clinical events committee reviewed and adjudicated suspected MI, ischemia-driven revascularization, stent thrombosis, and stroke blinded to knowledge of the study medication (Mahaffey K. W. et al., *Am Heart J* 143:242-8 (2002)).

Determination of periprocedural MI can be challenging when most patients have elevated biomarkers and a single baseline sample. After the initial analyses were completed and reviewed, additional post-hoc composites were performed to better understand the potential effect of the drug on periprocedural outcomes less reliant on biomarkers (e.g., death, stent thrombosis, and Q-wave MI).

The sample size was based on the estimated composite incidence of all-cause mortality, MI, and ischemia-driven revascularization at 48 hours. Since there was no prior information about the use of cangrelor in the setting of STEMI and primary PCI and given the challenge of measuring re-infarction in the early hours of STEMI, the primary efficacy endpoint excluded these patients from the analysis, though they were included in analyses of safety. The composite event rate was estimated at 7% in the control clopidogrel arm. The trial was designed as a superiority trial to demonstrate a benefit of cangrelor over 600 mg clopidogrel. Assuming a 22% risk reduction, a sample size of 8000 patients would provide approximately 82% power with an alpha level of 0.05. The plan was to include up to 1000 patients with STEMI, raising the sample size to 9000 patients.

The primary efficacy analysis was to be determined in the modified intent-to-treat (mITT) population, defined as all randomized subjects (excluding STEMI cohort) who received at least one dose of study drug and underwent the index PCI. The safety population consisted of all randomized patients who received any study drug. Patients in the safety analyses were assigned to a treatment arm based on treatment received, not as randomized. The ITT analysis with and without the STEMI cohort is reported.

All statistical tests were two-tailed using a level of significance of 0.05. The primary endpoint comparison between the cangrelor and placebo arms was performed by calculating an odds ratio (OR), with accompanying 95% confidence intervals (CI), using logistic regression. Logistic regression was used to analyze the majority of the remaining secondary endpoints. Continuous variables are summarized by medians and interquartile ranges. Categorical variables are summarized by frequencies and percentages. In the secondary efficacy analyses, there was no attempt to adjust the P values for the multiplicity issue. These analyses were considered exploratory and hypothesis-generating.

At the end of the study, 98% (n=8877) of the expected 9000 patients had been enrolled at 268 sites across 14 countries. For the 48-hour and 30-day endpoints, vital status follow-up was 99.7% and 98.6% complete, respectively.

Baseline demographics on the ITT population are shown in Table 5. Baseline demographics for the mITT and safety populations are shown in Tables 6 and 7.

TABLE 5

Baseline characteristics for ITT Population

| Baseline characteristics | ITT Cangrelor (N = 4433) | ITT Clopidogrel (N = 4444) | ITT Without STEMI Cangrelor (N = 3946) |
|---|---|---|---|
| Age, yrs | 62.0 (54.0, 70.0) | 62.0 (54.0, 71.0) | 63.0 (55.0, 71.0) |
| Sex, No. (%) | | | |
| Male | 3275 (73.9) | 3209 (72.2) | 2891 (73.3) |
| Female | 1158 (26.1) | 1235 (27.8) | 1055 (26.7) |
| Race, No. (%) | | | |
| White | 3658 (82.6) | 3626 (81.7) | 3229 (81.9) |
| Asian | 311 (7.0) | 313 (7.1) | 294 (7.5) |
| Black | 215 (4.9) | 239 (5.4) | 190 (4.8) |
| Hispanic | 209 (4.7) | 218 (4.9) | 197 (5.0) |
| Other | 35 (0.8) | 42 (1.0) | 31 (0.8) |
| Weight, kg | 84.0 (73.0, 97.0) | 84.0 (73.0, 97.0) | 84.0 (73.0, 97.0) |
| Height, cm | 172.0 (165.0, 178.0) | 172.0 (165.0, 178.0) | 172.0 (165.0, 178.0) |
| Stable angina, No. (%) | 668 (15.1) | 665 (15.0) | 668 (16.9) |
| Unstable angina, No. (%) | 1097 (24.7) | 1088 (24.5) | 1097 (27.8) |
| Urgent NSTEMI, No. (%) | 639 (14.4) | 640 (14.4) | 639 (16.2) |
| NSTEMI, No. (%) | 1542 (34.8) | 1542 (34.7) | 1542 (39.1) |
| STEMI, No. (%) | 487 (11.0) | 509 (11.5) | 0 (0.0) |
| Medical history, No. (%) | | | |
| Diabetes mellitus | 1350 (30.5) | 1352 (30.5) | 1248 (31.6) |
| Current smoker | 1247 (28.5) | 1283 (29.1) | 1035 (26.6) |
| Hypertension | 3181 (72.1) | 3139 (71.0) | 2900 (73.8) |
| Hyperlipidemia | 2825 (66.6) | 2777 (65.5) | 2590 (68.4) |
| Stroke/TIA | 223 (5.1) | 227 (5.1) | 208 (5.3) |
| Family history of CAD | 1843 (45.9) | 1873 (46.5) | 1656 (46.1) |
| MI | 1075 (24.6) | 1089 (24.8) | 1003 (25.9) |
| PTCA/PCI | 1266 (28.6) | 1261 (28.5) | 1193 (30.3) |
| CABG | 557 (12.6) | 552 (12.4) | 541 (13.7) |
| Congestive HF | 333 (7.6) | 338 (7.7) | 319 (8.2) |
| PAD | 323 (7.4) | 315 (7.2) | 294 (7.6) |
| Periprocedural medications, No. (%) | | | |
| Bivalirudin | 1313 (29.6) | 1337 (30.1) | 1244 (31.5) |
| UFH | 2437 (55.0) | 2452 (55.3) | 2154 (54.6) |
| LMWH | 368 (8.3) | 340 (7.7) | 322 (8.2) |
| GP IIb/IIIa | 1163 (26.3) | 1183 (26.7) | 909 (23.0) |
| Study treatment Number of target vessels, No. (%) | | | |
| 1 | 3836 (88.0) | 3796 (87.4) | 3406 (87.3) |
| 2 | 484 (11.1) | 509 (11.7) | 457 (11.7) |
| 3 | 38 (0.9) | 36 (0.8) | 38 (1.0) |
| Drug-eluting stent, No. (%) | 2581 (59.2) | 2560 (59.0) | 2422 (62.1) |
| Non-drug-eluting stent, No. (%) | 1640 (37.6) | 1635 (37.7) | 1367 (35.0) |
| Angiographic complications (site reported) | | | |
| Threatened abrupt closure | 13 (0.3) | 12 (0.3) | 9 (0.2) |
| Unsuccessful procedure | 90 (2.1) | 103 (2.4) | 81 (2.1) |
| Abrupt vessel closure | 24 (0.6) | 22 (0.5) | 20 (0.5) |
| New thrombus or suspected thrombus | 17 (0.4) | 23 (0.5) | 16 (0.4) |
| Acute stent thrombosis | 2 (0.0) | 5 (0.1) | 2 (0.1) |
| Need for urgent CABG | 10 (0.2) | 7 (0.2) | 8 (0.2) |

TABLE 5-continued

Baseline characteristics for ITT Population

| | | | |
|---|---|---|---|
| IV study drug administered, No. (%) | 4367 (98.5) | 4355 (98.0) | 3904 (99.0) |
| Bolus administered, No. (%) | 4367 (98.5) | 4354 (98.0) | 3904 (99.0) |
| Infusion administered, No. (%) | 4364 (98.5) | 4353 (98.0) | 3901 (98.9) |
| Duration of infusion, hrs | 2.1 (2.0, 2.2) | 2.1 (2.0, 2.2) | 2.1 (2.0, 2.2) |
| Oral study drug administered, No. (%) | 4351 (98.2) | 4345 (97.8) | 3896 (98.8) |

| | ITT Without STEMI | ITT With STEMI | |
|---|---|---|---|
| Baseline characteristics | Clopidogrel (N = 3935) | Cangrelor (N = 487) | Clopidogrel (N = 509) |
| Age, yrs | 62.0 (54.0, 71.0) | 58.0 (51.0, 67.0) | 61.0 (52.0, 70.0) |
| Sex, No. (%) | | | |
| Male | 2831 (71.9) | 384 (78.9) | 378 (74.3) |
| Female | 1104 (28.1) | 103 (21.1) | 131 (25.7) |
| Race, No. (%) | | | |
| White | 3184 (81.0) | 429 (88.1) | 442 (87.0) |
| Asian | 300 (7.6) | 17 (3.5) | 13 (2.6) |
| Black | 208 (5.3) | 25 (5.1) | 31 (6.1) |
| Hispanic | 204 (5.2) | 12 (2.5) | 14 (2.8) |
| Other | 34 (0.9) | 4 (0.8) | 8 (1.6) |
| Weight, kg | 84.0 (73.0, 98.0) | 83 (72.0, 95.0) | 82.0 (72.0, 95.0) |
| Height, cm | 172.0 (165.0, 178.0) | 173.0 (167.6, 178.0) | 172.0 (165.0, 178.0) |
| Stable angina, No. (%) | 665 (16.9) | 0 (0.0) | 0 (0.0) |
| Unstable angina, No. (%) | 1088 (27.6) | 0 (0.0) | 0 (0.0) |
| Urgent NSTEMI, No. (%) | 640 (16.3) | 0 (0.0) | 0 (0.0) |
| NSTEMI, No. (%) | 1542 (39.2) | 0 (0.0) | 0 (0.0) |
| STEMI, No. (%) | 0 (0.0) | 487 (100.0) | 509 (100.0) |
| Medical history, No. (%) | | | |
| Diabetes mellitus | 1263 (32.1) | 102 (20.9) | 89 (17.5) |
| Current smoker | 1076 (27.6) | 212 (43.7) | 207 (41.2) |
| Hypertension | 2839 (72.4) | 281 (58.1) | 300 (60.0) |
| Hyperlipidemia | 2536 (67.4) | 235 (51.5) | 241 (50.8) |
| Stroke/TIA | 205 (5.2) | 15 (3.1) | 22 (4.4) |
| Family history of CAD | 1686 (47.1) | 187 (43.7) | 187 (41.6) |
| MI | 1007 (26.0) | 72 (14.9) | 82 (16.2) |
| PTCA/PCI | 1198 (30.6) | 73 (15.0) | 63 (12.4) |
| CABG | 532 (13.5) | 16 (3.3) | 20 (3.9) |
| Congestive HF | 322 (8.3) | 14 (2.9) | 16 (3.2) |
| PAD | 290 (7.5) | 29 (6.0) | 25 (5.0) |
| Periprocedural medications, No. (%) | | | |
| Bivalirudin | 1250 (31.8) | 69 (14.2) | 87 (17.1) |
| UFH | 2155 (54.8) | 283 (58.2) | 297 (58.5) |
| LMWH | 298 (7.6) | 46 (9.5) | 42 (8.3) |
| GP IIb/IIIa | 927 (23.6) | 254 (52.3) | 256 (50.4) |
| Study treatment | | | |
| Number of target vessels, No. (%) | | | |
| 1 | 3360 (86.5) | 430 (94.1) | 436 (95.2) |
| 2 | 488 (12.6) | 27 (5.9) | 21 (4.6) |
| 3 | 35 (0.9) | 0 (0.0) | 1 (0.2) |
| Drug-eluting stent, No. (%) | 2383 (61.4) | 159 (34.8) | 177 (38.6) |
| Non-drug-eluting stent, No. (%) | 1380 (35.5) | 273 (59.7) | 255 (55.7) |
| Angiographic complications (site reported) | | | |
| Threatened abrupt closure | 10 (0.3) | 4 (0.9) | 2 (0.4) |
| Unsuccessful procedure | 92 (2.4) | 9 (2.0) | 11 (2.4) |
| Abrupt vessel closure | 19 (0.5) | 4 (0.9) | 3 (0.7) |
| New thrombus or suspected thrombus | 16 (0.4) | 1 (0.2) | 7 (1.5) |
| Acute stent thrombosis | 5 (0.1) | 0 (0.0) | 0 (0.0) |
| Need for urgent CABG | 7 (0.2) | 2 (0.4) | 0 (0.0) |
| IV study drug administered, No. (%) | 3883 (98.7) | 463 (95.1) | 472 (92.7) |
| Bolus administered, No. (%) | 3883 (98.7) | 463 (95.1) | 471 (92.5) |
| Infusion administered, No. (%) | 3882 (98.7) | 463 (95.1) | 471 (92.5) |
| Duration of infusion, hrs | 2.1 (2.0, 2.2) | 2.0 (2.0, 2.2) | 2.1 (2.0, 2.2) |
| Oral study drug administered, No. (%) | 3882 (98.7) | 455 (93.4) | 463 (91.0) |

Variables are presented as median (25th, 75th) unless otherwise indicated. CABG denotes coronary artery bypass grafting; CAD, coronary artery disease; GP, glycoprotein; HF, heart failure; ITT, intent to treat; IV, intravenous; LMWH, low molecular weight heparin; MI, myocardial infarction; NSTEMI, non-ST-segment elevation myocardial infarction; PAD, peripheral artery disease; PCI, percutaneous coronary intervention; PTCA, percutaneous transluminal coronary angioplasty; STEMI, ST-segment elevation myocardial infarction; TIA, transient ischemic attack; UFH, unfractionated heparin.

TABLE 6

MITT and MITT NSTEMI Population

| Baseline characteristics | MITT | | MITT NSTEMI | |
|---|---|---|---|---|
| | Cangrelor (N = 4347) | Clopidogrel (N = 4320) | Cangrelor (N = 3897) | Clopidogrel (N = 3871) |
| Age, yrs | 62.0 (54.0, 70.0) | 62.0 (54.0, 71.0) | 63.0 (55.0, 70.0) | 62.0 (54.0, 71.0) |
| Sex, No. (%) | | | | |
| Male | 3212 (73.9) | 3124 (72.3) | 2854 (73.2) | 2786 (72.0) |
| Female | 1135 (26.1) | 1196 (27.7) | 1043 (26.8) | 1085 (28.0) |
| Race, No. (%) | | | | |
| White | 3589 (82.7) | 3516 (81.5) | 3193 (82.0) | 3127 (80.9) |
| Asian | 306 (7.0) | 312 (7.2) | 289 (7.4) | 299 (7.7) |
| Black | 208 (4.8) | 230 (5.3) | 185 (4.8) | 205 (5.3) |
| Hispanic | 205 (4.7) | 214 (5.0) | 194 (5.0) | 201 (5.2) |
| Other | 34 (0.8) | 42 (1.0) | 31 (0.8) | 34 (0.9) |
| Weight, kg | 84.0 (73.0, 97.0) | 84.0 (73.0, 97.0) | 84.0 (73.0, 97.0) | 84.0 (73.0, 97.0) |
| Height, cm | 172.0 (165.0, 178.0) | 172.0 (165.0, 178.0) | 172.0 (165.0, 178.0) | 172.0 (165.0, 178.0) |
| Stable angina, No. (%) | 659 (15.2) | 645 (14.9) | 659 (16.9) | 645 (16.7) |
| Unstable angina, No. (%) | 1088 (25.0) | 1071 (24.8) | 1088 (27.9) | 1071 (27.7) |
| Urgent NSTEMI, No. (%) | 627 (14.4) | 632 (14.6) | 627 (16.1) | 632 (16.3) |
| NSTEMI, No. (%) | 1523 (35.0) | 1523 (35.3) | 1523 (39.1) | 1523 (39.3) |
| STEMI, No. (%) | 450 (10.4) | 449 (10.4) | 0 (0.0) | 0 (0.0) |
| Medical history, No. (%) | | | | |
| Diabetes mellitus | 1327 (30.5) | 1313 (30.4) | 1233 (31.7) | 1238 (32.0) |
| Current smoker | 1229 (28.6) | 1245 (29.0) | 1025 (26.6) | 1057 (27.5) |
| Hypertension | 3122 (72.2) | 3045 (70.9) | 2865 (73.8) | 2788 (72.3) |
| Hyperlipidemia | 2771 (66.6) | 2705 (65.7) | 2555 (68.3) | 2491 (67.3) |
| Stroke/TIA | 220 (5.1) | 218 (5.1) | 206 (5.3) | 201 (5.2) |
| Family history of CAD | 1809 (45.9) | 1825 (46.6) | 1637 (46.1) | 1656 (47.1) |
| MI | 1059 (24.7) | 1054 (24.7) | 991 (25.9) | 983 (25.8) |
| PTCA/PCI | 1247 (28.8) | 1229 (28.6) | 1181 (30.4) | 1172 (30.4) |
| CABG | 546 (12.6) | 537 (12.4) | 533 (13.7) | 521 (13.5) |
| Congestive HF | 325 (7.5) | 326 (7.6) | 314 (8.1) | 311 (8.1) |
| PAD | 320 (7.5) | 304 (7.2) | 292 (7.6) | 282 (7.4) |
| Periprocedural medications, No. (%) | | | | |
| Bivalirudin | 1298 (29.9) | 1316 (30.5) | 1232 (31.6) | 1232 (31.8) |
| UFH | 2399 (55.2) | 2404 (55.7) | 2134 (54.8) | 2132 (55.1) |
| LMWH | 364 (8.4) | 334 (7.7) | 319 (8.2) | 297 (7.7) |
| GP IIb/IIIa | 1148 (26.4) | 1160 (26.9) | 903 (23.2) | 921 (23.8) |
| Study treatment | | | | |
| Number of target vessels, No. (%) | | | | |
| 1 | 3818 (88.0) | 3772 (87.4) | 3395 (87.3) | 3345 (86.5) |
| 2 | 482 (11.1) | 506 (11.7) | 455 (11.7) | 485 (12.5) |
| 3 | 38 (0.9) | 36 (0.8) | 38 (1.0) | 35 (0.9) |
| Drug-eluting stent, No. (%) | 2572 (59.3) | 2547 (59.0) | 2415 (62.1) | 2375 (61.4) |
| Non-drug-eluting stent, No. (%) | 1632 (37.6) | 1628 (37.7) | 1362 (35.0) | 1375 (35.6) |
| Angiographic complications (site reported) | | | | |
| Threatened abrupt closure | 13 (0.3) | 12 (0.3) | 9 (0.2) | 10 (0.3) |
| Unsuccessful procedure | 90 (2.1) | 103 (2.4) | 81 (2.1) | 92 (2.4) |
| Abrupt vessel closure | 24 (0.6) | 22 (0.5) | 20 (0.5) | 19 (0.5) |
| New thrombus or suspected thrombus | 17 (0.4) | 22 (0.5) | 16 (0.4) | 16 (0.4) |
| Acute stent thrombosis | 2 (0.0) | 5 (0.1) | 2 (0.1) | 5 (0.1) |
| Need for urgent CABG | 8 (0.2) | 6 (0.1) | 7 (0.2) | 6 (0.1) |
| IV study drug administered, No. (%) | 4345 (100.0) | 4317 (99.9) | 3895 (99.9) | 3868 (99.9) |
| Bolus administered, No. (%) | 4345 (100.0) | 4316 (99.9) | 3895 (99.9) | 3868 (99.9) |
| Infusion administered, No. (%) | 4344 (99.9) | 4317 (99.9) | 3894 (99.9) | 3868 (99.9) |

TABLE 6-continued

MITT and MITT NSTEMI Population

| | MITT | | MITT NSTEMI | |
|---|---|---|---|---|
| Baseline characteristics | Cangrelor (N = 4347) | Clopidogrel (N = 4320) | Cangrelor (N = 3897) | Clopidogrel (N = 3871) |
| Duration of infusion, hrs | 2.1 (2.0, 2.2) | 2.1 (2.0, 2.2) | 2.1 (2.0, 2.2) | 2.1 (2.0, 2.2) |
| Oral study drug administered, No. (%) | 4329 (99.6) | 4305 (99.7) | 3884 (99.7) | 3863 (99.8) |

Variables are presented as median (25th, 75th) unless otherwise indicated.
CABG denotes coronary artery bypass grafting;
CAD, coronary artery disease;
GP, glycoprotein;
HF, heart failure;
IV, intravenous;
LMWH, low molecular weight heparin;
MI, myocardial infarction;
MITT, modified intent to treat;
NSTEMI, non-ST-segment elevation myocardial infarction;
PAD, peripheral artery disease;
PCI, percutaneous coronary intervention;
PTCA, percutaneous transluminal coronary angioplasty;
STEMI, ST-segment elevation myocardial infarction;
TIA, transient ischemic attack;
UFH, unfractionated heparin.

TABLE 7

Safety Population

| Baseline characteristics | Cangrelor (N = 4374) | Clopidogrel (N = 4365) |
|---|---|---|
| Age, yrs | 62.0 (54.0, 70.0) | 62.0 (54.0, 71.0) |
| Sex, No. (%) | | |
| Male | 3229 (73.8) | 3149 (72.1) |
| Female | 1145 (26.2) | 1216 (27.9) |
| Race, No. (%) | | |
| White | 3610 (82.6) | 3558 (81.6) |
| Asian | 309 (7.1) | 312 (7.2) |
| Black | 208 (4.8) | 233 (5.3) |
| Hispanic | 206 (4.7) | 215 (4.9) |
| Other | 36 (0.8) | 41 (1.0) |
| Weight, kg | 84.0 (73.0, 97.0) | 84.0 (73.0, 97.0) |
| Height, cm | 172.0 (165.0, 178.0) | 172.0 (165.0, 178.0) |
| Stable angina, No. (%) | 661 (15.1) | 654 (15.0) |
| Unstable angina, No. (%) | 1091 (24.9) | 1074 (24.6) |
| Urgent NSTEMI, No. (%) | 629 (14.4) | 634 (14.5) |
| NSTEMI, No. (%) | 1529 (35.0) | 1529 (35.0) |
| STEMI, No. (%) | 463 (10.6) | 475 (10.9) |
| Medical history, No. (%) | | |
| Diabetes mellitus | 1337 (30.6) | 1325 (30.4) |
| Current smoker | 1233 (28.5) | 1257 (29.0) |
| Hypertension | 3143 (72.2) | 3083 (71.0) |
| Hyperlipidemia | 2787 (66.6) | 2728 (65.6) |
| Stroke/TIA | 220 (5.1) | 221 (5.1) |
| Family history of CAD | 1818 (45.8) | 1838 (46.5) |
| MI | 1064 (24.7) | 1067 (24.8) |
| PTCA/PCI | 1253 (28.7) | 1237 (28.4) |
| CABG | 550 (12.6) | 540 (12.4) |
| Congestive HF | 328 (7.6) | 332 (7.7) |
| PAD | 321 (7.5) | 309 (7.2) |
| Periprocedural medications, No. (%) | | |
| Bivalirudin | 1299 (29.7) | 1320 (30.2) |
| UFH | 2413 (55.2) | 2424 (55.5) |
| LMWH | 365 (8.4) | 340 (7.8) |
| GP IIb/IIIa | 1154 (26.4) | 1170 (26.8) |
| Study treatment | | |
| Number of target vessels, No. (%) | | |
| 1 | 3819 (88.0) | 3771 (87.4) |
| 2 | 482 (11.1) | 506 (11.7) |

TABLE 7-continued

Safety Population

| Baseline characteristics | Cangrelor (N = 4374) | Clopidogrel (N = 4365) |
|---|---|---|
| 3 | 38 (0.9) | 36 (0.8) |
| Drug-eluting stent, No. (%) | 2572 (59.3) | 2547 (59.0) |
| Non-drug-eluting stent, No. (%) | 1633 (37.6) | 1627 (37.7) |
| Angiographic complications (site reported) | | |
| Threatened abrupt closure | 13 (0.3) | 12 (0.3) |
| Unsuccessful procedure | 90 (2.1) | 103 (2.4) |
| Abrupt vessel closure | 24 (0.6) | 22 (0.5) |
| New thrombus or suspected thrombus | 17 (0.4) | 22 (0.5) |
| Acute stent thrombosis | 2 (0.0) | 5 (0.1) |
| Need for urgent CABG | 8 (0.2) | 6 (0.1) |
| IV study drug administered, No. (%) | 4368 (99.9) | 4354 (99.7) |
| Bolus administered, No. (%) | 4368 (99.9) | 4353 (99.7) |
| Infusion administered, No. (%) | 4365 (99.8) | 4352 (99.7) |
| Duration of infusion, hrs | 2.1 (2.0, 2.2) | 2.1 (2.0, 2.2) |
| Oral study drug administered, No. (%) | 4352 (99.5) | 4344 (99.5) |

Variables are presented as median (25th, 75th) unless otherwise indicated.
CABG denotes coronary artery bypass grafting;
CAD, coronary artery disease;
GP, glycoprotein;
HF, heart failure;
IV, intravenous;
LMWH, low molecular weight heparin;
MI, myocardial infarction;
NSTEMI, non-ST-segment elevation myocardial infarction;
PAD, peripheral artery disease;
PCI, percutaneous coronary intervention;
PTCA, percutaneous transluminal coronary angioplasty;
STEMI, ST-segment elevation myocardial infarction;
TIA, transient ischemic attack;
UFH, unfractionated heparin.

There were no significant differences regarding baseline characteristics. Enrolled patients were typical of a contemporary PCI population, being mostly men and having a median age of 62 years (54.0, 71.0). Diabetes was noted in 30.5% while hypertension or hyperlipidemia was present in the majority of patients. Previous cardiac events included MI in 24.7% and revascularization in 41.1% (28.6% PCI, 12.5% bypass grafting). Almost half (49%) of enrolled patients had NSTEMI at baseline while stable angina and unstable angina were the baseline diagnoses in 15.0% and 24.6%, respectively. The STEMI cohort included 996 (11.2%) patients.

During the index procedure, a majority of patients (55.1%) received unfractionated heparin, and 29.9% received bivalirudin. Glycoprotein IIb/IIIa inhibitors were used in 26.5% with most receiving eptifibatide (75.0%). Almost all (98%) patients in the ITT population received study drug. Sites were instructed to start PCI within 30 minutes of clopidogrel capsules.

PCI was attempted in all but 161 patients (1.8%), 65 in the cangrelor group (1.5%) and 96 in the clopidogrel group (2.2%). The median duration of PCI was 0.4 hours (0.2, 0.6) and the median time from hospital admission to PCI was 6.3 hours (2.6, 23.7). Most procedures involved single-vessel or two-vessel PCI (87.7% and 11.4%, respectively). Drug-eluting stents were used in the majority of interventions (59.1%), bare-metal stents were used in 37.6%.

Cangrelor was equivalent to 600 mg clopidogrel in the primary composite of all-cause mortality, MI, or ischemia-driven revascularization at 48 hours (7.5% vs 7.1%; OR 1.05, 95% CI 0.88, 1.24; P=0.59) (Table 8).

TABLE 8

48-hour endpoints for MITT Without STEMI Population

| | MITT Without STEMI | | | |
|---|---|---|---|---|
| | Cangrelor (N = 3897) | Clopidogrel (N = 3871) | OR (95% CI) | P Value |
| Adjudicated endpoints | | | | |
| Death/MI/IDR (primary endpoint) | 290 (7.5) | 276 (7.1) | 1.05 (0.88, 1.24) | 0.59 |
| MI | 278 (7.1) | 256 (6.6) | 1.09 (0.91, 1.29) | 0.36 |
| IDR | 13 (0.3) | 23 (0.6) | 0.56 (0.28, 1.11) | 0.10 |
| All-cause mortality | 8 (0.2) | 5 (0.1) | 1.59 (0.52, 4.87) | 0.42 |
| Stent thrombosis | 7 (0.2) | 11 (0.3) | 0.63 (0.25, 1.63) | 0.34 |
| Stroke | 6 (0.2) | 7 (0.2) | 0.85 (0.29, 2.54) | 0.77 |
| Q-wave MI | 4 (0.1) | 10 (0.3) | 0.40 (0.12, 1.27) | 0.12 |
| Exploratory endpoints | | | | |
| Death/Q-wave MI/IDR | 23 (0.6) | 34 (0.9) | 0.67 (0.39, 1.14) | 0.14 |
| Death/Q-wave MI/Stent thrombosis | 18 (0.5) | 23 (0.6) | 0.78 (0.42, 1.44) | 0.42 |

Figure 6A:
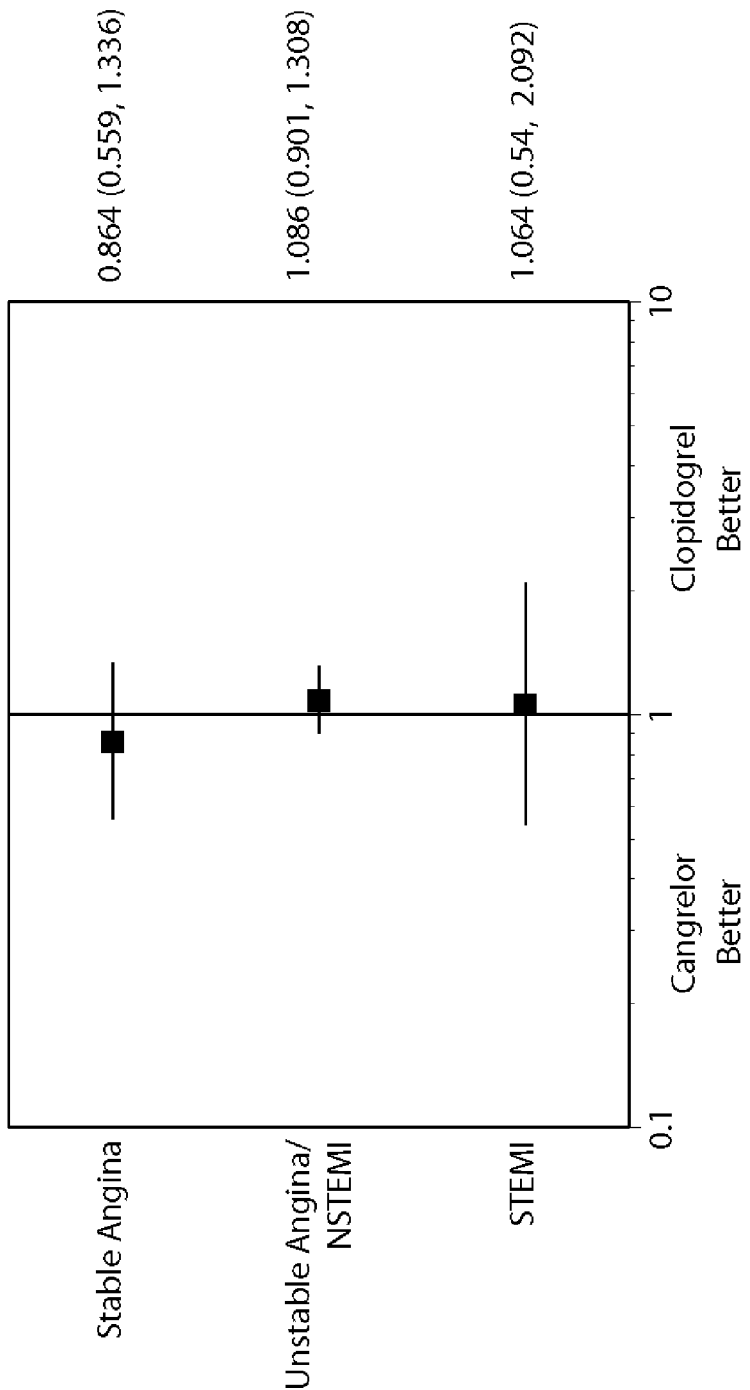
FIGS. 6A and 6B—display the primary endpoint OR data for key subgroups in the efficacy study of cangrelor versus placebo administered to patients before percutaneous coronary intervention (PCI).
Figure 6B:
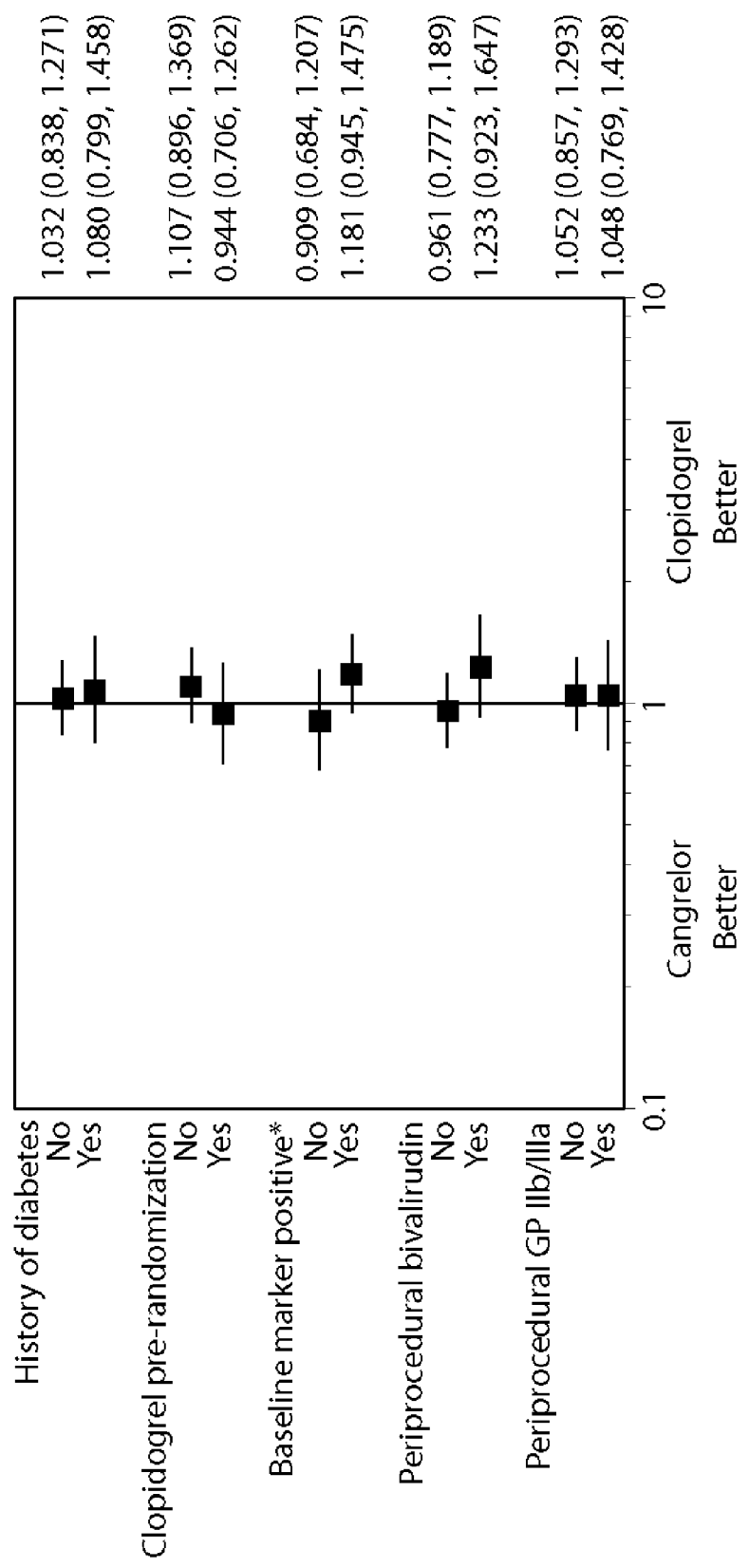

The primary efficacy composite did not differ at 30 days (Table 9). FIGS. 6A and 6B display the primary endpoint OR data for key subgroups.

TABLE 9

30-day endpoints for ITT, MITT, and Safety Populations

ITT

| | Cangrelor (N = 4433) | Clopidogrel (N = 4444) | OR (95% CI) | P Value |
|---|---|---|---|---|
| Death/MI/IDR | 381 (8.7) | 373 (8.5) | 1.026 (0.884, 1.192) | 0.7332 |
| MI | 318 (7.3) | 293 (6.7) | 1.095 (0.929, 1.291) | 0.2799 |
| IDR | 62 (1.4) | 69 (1.6) | 0.899 (0.637, 1.271) | 0.5475 |
| All-cause mortality | 40 (0.9) | 47 (1.1) | 0.852 (0.558, 1.301) | 0.4583 |
| Stent thrombosis | 27 (0.6) | 30 (0.7) | 0.902 (0.535, 1.519) | 0.6973 |
| Q-wave MI | 9 (0.2) | 15 (0.3) | 0.601 (0.263, 1.374) | 0.2273 |
| Death/Q-wave MI/IDR | 102 (2.3) | 119 (2.7) | 0.856 (0.655, 1.119) | 0.2550 |
| Death/Q-wave MI/Stent thrombosis | 68 (1.6) | 82 (1.9) | 0.829 (0.599, 1.146) | 0.2560 |

ITT Without STEMI

| | Cangrelor (N = 3946) | Clopidogrel (N = 3935) | OR (95% CI) | P Value |
|---|---|---|---|---|
| Death/MI/IDR | 345 (8.8) | 332 (8.6) | 1.037 (0.886, 1.215) | 0.6481 |
| MI | 298 (7.6) | 276 (7.1) | 1.081 (0.912, 1.281) | 0.3718 |
| IDR | 46 (1.2) | 54 (1.4) | 0.846 (0.569, 1.257) | 0.4072 |
| All-cause mortality | 32 (0.8) | 31 (0.8) | 1.027 (0.626, 1.687) | 0.9148 |
| Stent thrombosis | 20 (0.5) | 20 (0.5) | 0.995 (0.535, 1.852) | 0.9877 |
| Q-wave MI | 7 (0.2) | 15 (0.4) | 0.463 (0.189, 1.138) | 0.0933 |
| Death/Q-wave MI/IDR | 79 (2.0) | 88 (2.3) | 0.891 (0.656, 1.211) | 0.4620 |
| Death/Q-wave MI/Stent thrombosis | 54 (1.4) | 56 (1.4) | 0.959 (0.658, 1.397) | 0.8276 |

ITT With STEMI

| | Cangrelor (N = 487) | Clopidogrel (N = 509) | OR (95% CI) | P Value |
|---|---|---|---|---|
| Death/MI/IDR | 36 (7.6) | 41 (8.2) | 0.929 (0.582, 1.480) | 0.7553 |
| MI | 20 (4.2) | 17 (3.4) | 1.263 (0.653, 2.441) | 0.4882 |
| IDR | 16 (3.4) | 15 (3.0) | 1.139 (0.557, 2.331) | 0.7210 |
| All-cause mortality | 8 (1.7) | 16 (3.2) | 0.524 (0.222, 1.235) | 0.1397 |
| Stent thrombosis | 7 (1.5) | 10 (2.0) | 0.741 (0.280, 1.962) | 0.5460 |
| Q-wave MI | 2 (0.4) | 0 (0.0) | — | — |
| Death/Q-wave MI/IDR | 23 (4.9) | 31 (6.2) | 0.778 (0.447, 1.355) | 0.3760 |
| Death/Q-wave MI/Stent thrombosis | 14 (3.0) | 26 (5.2) | 0.560 (0.289, 1.085) | 0.0859 |

MITT

| | Cangrelor (N = 4347) | Clopidogrel (N = 4320) | OR (95% CI) | P Value |
|---|---|---|---|---|
| Death/MI/IDR | 376 (8.7) | 360 (8.4) | 1.042 (0.895, 1.211) | 0.5979 |
| MI | 315 (7.3) | 292 (6.8) | 1.078 (0.914, 1.271) | 0.3747 |
| IDR | 60 (1.4) | 66 (1.5) | 0.902 (0.634, 1.283) | 0.5660 |
| All-cause mortality | 40 (0.9) | 38 (0.9) | 1.046 (0.670, 1.635) | 0.8419 |
| Stent thrombosis | 27 (0.6) | 30 (0.7) | 0.894 (0.530, 1.506) | 0.6728 |
| Q-wave MI | 9 (0.2) | 15 (0.4) | 0.595 (0.260, 1.362) | 0.2194 |
| Death/Q-wave MI/IDR | 100 (2.3) | 107 (2.5) | 0.927 (0.703, 1.222) | 0.5904 |
| Death/Q-wave MI/Stent thrombosis | 68 (1.6) | 73 (1.7) | 0.924 (0.663, 1.290) | 0.6439 |

MITT Without STEMI

| | Cangrelor (N = 3897) | Clopidogrel (N = 3871) | OR (95% CI) | P Value |
|---|---|---|---|---|
| Death/MI/IDR | 342 (8.9) | 326 (8.5) | 1.044 (0.891, 1.224) | 0.5950 |
| MI | 297 (7.7) | 276 (7.2) | 1.072 (0.905, 1.272) | 0.4208 |
| IDR | 44 (1.1) | 52 (1.4) | 0.837 (0.559, 1.254) | 0.3882 |
| All-cause mortality | 32 (0.8) | 27 (0.7) | 1.177 (0.704, 1.967) | 0.5355 |
| Stent thrombosis | 20 (0.5) | 20 (0.5) | 0.991 (0.533, 1.846) | 0.9783 |
| Q-wave MI | 7 (0.2) | 15 (0.4) | 0.462 (0.188, 1.134) | 0.0917 |
| Death/Q-wave MI/IDR | 77 (2.0) | 82 (2.1) | 0.930 (0.679, 1.273) | 0.6489 |
| Death/Q-wave MI/Stent thrombosis | 54 (1.4) | 52 (1.4) | 1.030 (0.702, 1.511) | 0.8799 |

TABLE 9-continued 30-day endpoints for ITT, MITT, and Safety Populations

MITT With STEMI

|  | Cangrelor (N = 450) | Clopidogrel (N = 449) | OR (95% CI) | P Value |
|---|---|---|---|---|
| Death/MI/IDR | 34 (7.8) | 34 (7.7) | 1.015 (0.619, 1.665) | 0.9534 |
| MI | 18 (4.1) | 16 (3.6) | 1.146 (0.577, 2.278) | 0.6965 |
| IDR | 16 (3.7) | 14 (3.2) | 1.165 (0.561, 2.416) | 0.6825 |
| All-cause mortality | 8 (1.8) | 11 (2.5) | 0.732 (0.292, 1.838) | 0.5072 |
| Stent thrombosis | 7 (1.6) | 10 (2.3) | 0.705 (0.266, 1.869) | 0.4821 |
| Q-wave MI | 2 (0.5) | 0 (0.0) | — | — |
| Death/Q-wave MI/IDR | 23 (5.3) | 25 (5.6) | 0.929 (0.519, 1.663) | 0.8039 |
| Death/Q-wave MI/Stent thrombosis | 14 (3.2) | 21 (4.7) | 0.665 (0.334, 1.325) | 0.2464 |

Safety

|  | Cangrelor (N = 4374) | Clopidogrel (N = 4365) | OR (95% CI) | P Value |
|---|---|---|---|---|
| Death/MI/IDR | 379 (8.8) | 365 (8.5) | 1.040 (0.895, 1.209) | 0.6074 |
| MI | 318 (7.4) | 293 (6.8) | 1.090 (0.925, 1.285) | 0.3039 |
| IDR | 60 (1.4) | 67 (1.6) | 0.893 (0.628, 1.268) | 0.5257 |
| All-cause mortality | 40 (0.9) | 41 (0.9) | 0.974 (0.629, 1.508) | 0.9053 |
| Stent thrombosis | 27 (0.6) | 30 (0.7) | 0.898 (0.533, 1.513) | 0.6858 |
| Q-wave MI | 9 (0.2) | 15 (0.3) | 0.598 (0.262, 1.368) | 0.2236 |
| Death/Q-wave MI/IDR | 100 (2.3) | 111 (2.6) | 0.897 (0.682, 1.179) | 0.4364 |
| Death/Q-wave MI/Stent thrombosis | 68 (1.6) | 76 (1.8) | 0.892 (0.641, 1.240) | 0.4954 |

Variables are presented as no. (%) unless otherwise indicated.
CI denotes confidence interval;
IDR, ischemia-driven revascularization;
ITT, intent to treat;
MI, myocardial infarction;
MITT, modified intent to treat;
OR, odds ratio;
STEMI, ST-segment elevation myocardial infarction.

Forty-eight-hour bleeding events as observed in the safety population (including those with STEMI) are in Table 10. Reported adverse events were comparable between the groups (26.4% cangrelor, 25.7% clopidogrel) and discontinuation of study drug due to an adverse event was unusual in both groups (0.5% in both). Serious adverse events were infrequent and similar between the groups (2.7% in both). Dyspnea was reported in 1.0% of cangrelor patients compared with 0.4% of clopidogrel patients (P=0.001).

TABLE 10

48-hour bleeding events for safety population

| Bleeding events | Cangrelor (N = 4374) | Clopidogrel (N = 4365) | OR (95% CI) | P Value |
|---|---|---|---|---|
| Access site bleeding requiring radiologic or surgical intervention | 6 (0.1) | 10 (0.2) | 0.60 (0.22, 1.65) | 0.32 |
| Hematoma ≥5 cm at puncture site | 85 (1.9) | 76 (1.7) | 1.12 (0.82, 1.53) | 0.48 |
| Intracranial hemorrhage | 1 (0.0) | 0 (0.0) |  |  |
| Intraocular | 2 (0.0) | 0 (0.0) |  |  |
| Reoperation for bleeding | 1 (0.0) | 1 (0.0) | 1.00 (0.06, 15.96) | 1.00 |
| Retroperitoneal | 15 (0.3) | 10 (0.2) | 1.50 (0.67, 3.34) | 0.32 |
| Ecchymosis | 284 (6.5) | 234 (5.4) | 1.23 (1.03, 1.47) | 0.03 |
| Epistaxis | 9 (0.2) | 22 (0.5) | 0.41 (0.19, 0.89) | 0.02 |
| Hematoma <5 cm at puncture site | 251 (5.7) | 222 (5.1) | 1.14 (0.94, 1.37) | 0.18 |
| Oozing at puncture site | 400 (9.1) | 319 (7.3) | 1.28 (1.10, 1.49) | 0.002 |
| Thrombocytopenia | 6 (0.1) | 7 (0.2) | 0.86 (0.29, 2.55) | 0.78 |
| Hemodynamic compromise | 9 (0.2) | 11 (0.3) | 0.82 (0.34, 1.97) | 0.65 |
| Any blood transfusion | 46 (1.1) | 42 (1.0) | 1.09 (0.72, 1.67) | 0.68 |
| Any platelet transfusion | 6 (0.1) | 5 (0.1) | 1.20 (0.37, 3.93) | 0.77 |
| Drop in hemoglobin and/or hematocrit | 91 (2.1) | 63 (1.4) | 1.45 (1.05, 2.01) | 0.02 |
| Bleed scoring criteria |  |  |  |  |
| ACUITY criteria |  |  |  |  |
| Minor bleeding | 768 (17.6) | 663 (15.2) | 1.19 (1.06, 1.33) | 0.003 |
| Major bleeding | 158 (3.6) | 126 (2.9) | 1.26 (0.99, 1.60) | 0.06 |

TABLE 10-continued 48-hour bleeding events for safety population

| Bleeding events | Cangrelor (N = 4374) | Clopidogrel (N = 4365) | OR (95% CI) | P Value |
|---|---|---|---|---|
| GUSTO criteria | | | | |
| Mild bleeding | 858 (19.6) | 739 (16.9) | 1.20 (1.07, 1.34) | 0.001 |
| Moderate bleeding | 41 (0.9) | 34 (0.8) | 1.21 (0.76, 1.90) | 0.42 |
| Severe/life-threatening bleeding | 10 (0.2) | 11 (0.3) | 0.91 (0.39, 2.14) | 0.82 |
| TIMI criteria | | | | |
| Minor bleeding | 36 (0.8) | 26 (0.6) | 1.39 (0.84, 2.30) | 0.21 |
| Major bleeding | 19 (0.4) | 14 (0.3) | 1.36 (0.68, 2.71) | 0.39 |

Variables are presented as no. (%) unless otherwise indicated.
The bleeding options under each criterion are not mutually exclusive. For example, a patient may have a clinically significant bleed and a minor bleed based on the ACUITY criteria, if more than 1 bleed is present. Each patient will be counted once for each criteria level, regardless of the number of bleeds identified under each criterion.

Key secondary and composite exploratory (post-hoc) endpoints are displayed in Table 11.

TABLE 11

48-hour endpoints for ITT, MITT, and Safety Populations

| | MITT Without STEMI | | | |
|---|---|---|---|---|
| | Cangrelor (N = 3897) | Clopidogrel (N = 3871) | OR (95% CI) | P Value |
| Death/MI/IDR (Prespecified primary endpoint) | 290 (7.5) | 276 (7.1) | 1.048 (0.883, 1.243) | 0.5929 |
| MI | 278 (7.1) | 256 (6.6) | 1.085 (0.910, 1.294) | 0.3616 |
| IDR | 13 (0.3) | 23 (0.6) | 0.560 (0.283, 1.108) | 0.0957 |
| All-cause mortality | 8 (0.2) | 5 (0.1) | 1.591 (0.520, 4.869) | 0.4155 |
| Stent thrombosis | 7 (0.2) | 11 (0.3) | 0.632 (0.245, 1.631) | 0.3427 |
| Stroke | 6 (0.2) | 7 (0.2) | 0.852 (0.286, 2.536) | 0.7730 |
| Q-wave MI | 4 (0.1) | 10 (0.3) | 0.397 (0.124, 1.267) | 0.1186 |
| Death/Q-wave MI/IDR | 23 (0.6) | 34 (0.9) | 0.670 (0.394, 1.140) | 0.1399 |
| Death/Q-wave MI/Stent thrombosis | 18 (0.5) | 23 (0.6) | 0.777 (0.419, 1.442) | 0.4233 |

| | ITT | | | |
|---|---|---|---|---|
| | Cangrelor (N = 4433) | Clopidogrel (N = 4444) | OR (95% CI) | P Value |
| Death/MI/IDR | 312 (7.1) | 297 (6.7) | 1.058 (0.898, 1.248) | 0.4990 |
| MI | 294 (6.7) | 265 (6.0) | 1.122 (0.945, 1.331) | 0.1899 |
| IDR | 21 (0.5) | 31 (0.7) | 0.678 (0.389, 1.182) | 0.1710 |
| All-cause mortality | 9 (0.2) | 11 (0.2) | 0.821 (0.340, 1.983) | 0.6607 |
| Stent thrombosis | 11 (0.2) | 15 (0.3) | 0.735 (0.337, 1.603) | 0.4393 |
| Stroke | 6 (0.1) | 8 (0.2) | 0.752 (0.261, 2.170) | 0.5986 |
| Q-wave MI | 4 (0.1) | 10 (0.2) | 0.401 (0.126, 1.279) | 0.1226 |
| Death/Q-wave MI/IDR | 32 (0.7) | 48 (1.1) | 0.667 (0.425, 1.045) | 0.0770 |
| Death/Q-wave MI/Stent thrombosis | 23 (0.5) | 33 (0.7) | 0.698 (0.409, 1.191) | 0.1869 |

| | ITT Without STEMI | | | |
|---|---|---|---|---|
| | Cangrelor (N = 3946) | Clopidogrel (N = 3935) | OR (95% CI) | P Value |
| Death/MI/IDR | 292 (7.4) | 277 (7.1) | 1.056 (0.890, 1.252) | 0.5323 |
| MI | 278 (7.1) | 256 (6.5) | 1.090 (0.914, 1.299) | 0.3378 |
| IDR | 15 (0.4) | 23 (0.6) | 0.649 (0.338, 1.246) | 0.1943 |
| All-cause mortality | 8 (0.2) | 6 (0.2) | 1.331 (0.461, 3.839) | 0.5969 |
| Stent thrombosis | 7 (0.2) | 11 (0.3) | 0.634 (0.246, 1.638) | 0.3469 |
| Stroke | 6 (0.2) | 7 (0.2) | 0.855 (0.287, 2.546) | 0.7784 |
| Q-wave MI | 4 (0.1) | 10 (0.3) | 0.398 (0.125, 1.272) | 0.1202 |
| Death/Q-wave MI/IDR | 25 (0.6) | 35 (0.9) | 0.711 (0.425, 1.190) | 0.1941 |
| Death/Q-wave MI/Stent thrombosis | 18 (0.5) | 24 (0.6) | 0.747 (0.405, 1.379) | 0.3511 |

TABLE 11-continued 48-hour endpoints for ITT, MITT, and Safety Populations

ITT With STEMI

| | Cangrelor (N = 487) | Clopidogrel (N = 509) | OR (95% CI) | P Value |
|---|---|---|---|---|
| Death/MI/IDR | 20 (4.1) | 20 (3.9) | 1.054 (0.560, 1.985) | 0.8703 |
| MI | 16 (3.3) | 9 (1.8) | 1.900 (0.831, 4.341) | 0.1280 |
| IDR | 6 (1.2) | 8 (1.6) | 0.786 (0.271, 2.283) | 0.6584 |
| All-cause mortality | 1 (0.2) | 5 (1.0) | 0.209 (0.024, 1.793) | 0.1534 |
| Stent thrombosis | 4 (0.8) | 4 (0.8) | 1.052 (0.262, 4.321) | 0.9428 |
| Stroke | 0 (0.0) | 1 (0.2) | — | — |
| Q-wave MI | 0 (0.0) | 0 (0.0) | — | — |
| Death/Q-wave MI/IDR | 7 (1.5) | 13 (2.6) | 0.560 (0.222, 1.416) | 0.2204 |
| Death/Q-wave MI/Stent thrombosis | 5 (1.0) | 9 (1.8) | 0.580 (0.193, 1.743) | 0.3320 |

MITT

| | Cangrelor (N = 4347) | Clopidogrel (N = 4320) | OR (95% CI) | P Value |
|---|---|---|---|---|
| Death/MI/IDR | 308 (7.1) | 293 (6.8) | 1.049 (0.889, 1.238) | 0.5709 |
| MI | 292 (6.7) | 264 (6.1) | 1.107 (0.932, 1.315) | 0.2451 |
| IDR | 19 (0.4) | 30 (0.7) | 0.628 (0.353, 1.118) | 0.1140 |
| All-cause mortality | 9 (0.2) | 9 (0.2) | 0.995 (0.394, 2.508) | 0.9910 |
| Stent thrombosis | 11 (0.3) | 15 (0.3) | 0.729 (0.334, 1.588) | 0.4261 |
| Stroke | 6 (0.1) | 7 (0.2) | 0.852 (0.286, 2.538) | 0.7742 |
| Q-wave MI | 4 (0.1) | 10 (0.2) | 0.397 (0.125, 1.268) | 0.1190 |
| Death/Q-wave MI/IDR | 30 (0.7) | 45 (1.0) | 0.661 (0.416, 1.051) | 0.0801 |
| Death/Q-wave MI/Stent thrombosis | 23 (0.5) | 31 (0.7) | 0.737 (0.429, 1.265) | 0.2681 |

MITT With STEMI

| | Cangrelor (N = 450) | Clopidogrel (N = 449) | OR (95% CI) | P Value |
|---|---|---|---|---|
| Death/MI/IDR | 18 (4.0) | 17 (3.8) | 1.064 (0.541, 2.092) | 0.8578 |
| MI | 14 (3.1) | 8 (1.8) | 1.778 (0.739, 4.282) | 0.1991 |
| IDR | 6 (1.3) | 7 (1.6) | 0.857 (0.286, 2.571) | 0.7833 |
| All-cause mortality | 1 (0.2) | 4 (0.9) | 0.249 (0.028, 2.235) | 0.2143 |
| Stent thrombosis | 4 (0.9) | 4 (0.9) | 1.002 (0.249, 4.033) | 0.9975 |
| Stroke | 0 (0.0) | 0 (0.0) | — | — |
| Q-wave MI | 0 (0.0) | 0 (0.0) | — | — |
| Death/Q-wave MI/IDR | 7 (1.6) | 11 (2.5) | 0.632 (0.243, 1.645) | 0.3473 |
| Death/Q-wave MI/Stent thrombosis | 5 (1.1) | 8 (1.8) | 0.622 (0.202, 1.917) | 0.4084 |

Safety

| | Cangrelor (N = 4374) | Clopidogrel (N = 4365) | OR (95% CI) | P Value |
|---|---|---|---|---|
| Death/MI/IDR | 310 (7.1) | 294 (6.7) | 1.058 (0.896, 1.248) | 0.5073 |
| MI | 294 (6.7) | 265 (6.1) | 1.116 (0.940, 1.325) | 0.2091 |
| IDR | 19 (0.4) | 30 (0.7) | 0.631 (0.355, 1.123) | 0.1175 |
| All-cause mortality | 9 (0.2) | 9 (0.2) | 0.999 (0.396, 2.519) | 0.9984 |
| Stent thrombosis | 11 (0.3) | 15 (0.3) | 0.732 (0.336, 1.595) | 0.4326 |
| Stroke | 6 (0.1) | 7 (0.2) | 0.856 (0.288, 2.550) | 0.7803 |
| Q-wave MI | 4 (0.1) | 10 (0.2) | 0.399 (0.125, 1.273) | 0.1207 |
| Death/Q-wave MI/IDR | 30 (0.7) | 45 (1.0) | 0.664 (0.417, 1.056) | 0.0834 |
| Death/Q-wave MI/Stent thrombosis | 23 (0.5) | 31 (0.7) | 0.740 (0.431, 1.271) | 0.2751 |

Variables are presented as no. (%) unless otherwise indicated.
CI denotes confidence interval;
IDR, ischemia-driven revascularization;
ITT, intent to treat;
MI, myocardial infarction;
MITT, modified intent to treat;
OR, odds ratio;
STEMI, ST-segment elevation myocardial infarction.

A substudy was conducted at 15 sites to evaluate platelet function during infusion and to assess whether the administration of a cangrelor infusion prior to administration of clopidogrel 600 mg has any effect on platelet inhibition by clopidogrel. Patients in the substudy were required to be clopidogrel naïve and could not have received glycoprotein IIb/IIIa inhibition during the procedure. Platelet function parameters were measured using the VerifyNow $P2Y_{12}$ Assay (Accumetrics, San Diego, Calif.). Samples were taken before study drug administration, at approximately 2 hours (during cangrelor/placebo infusion), and 10 hours or next day following randomization.

The median baseline $P2Y_{12}$ reaction units (PRU) from the VerifyNow $P2Y_{12}$ assay were 335 in the cangrelor arm (264, 384; n=97) and 329 in the clopidogrel arm (285.5, 376.5; n=100). During the study drug infusion, the median PRU was significantly lower in the cangrelor arm (93.5; 40.0, 173.5; n=64) compared with the clopidogrel arm during the same time period (277; 206.0, 355.0; n=74). At 12-24 hours after discontinuation of the cangrelor infusion, the median PRU was 228 in the cangrelor arm (156.0, 298.0; n=87) and 206 in the clopidogrel arm (135.0, 274.0; n=87).

The results of this study demonstrated that the benefits of cangrelor infusion were equivalent to those of 600 mg clopidogrel using the predefined primary endpoint, although significantly higher levels of periprocedural platelet inhibition were achieved with cangrelor.

Example 3—Compatibility of Cangrelor Injection with Bivalirudin

Cangrelor is an investigational anti-platelet agent undergoing clinical development. In addition to cangrelor, patients may be administered other drugs parenterally via Y-site co-administration. The physical compatibility of cangrelor injection with bivalirudin during simulated Y-site co-administration was evaluated by visual observation, electronic turbidity measurement, and particulate content assessment.

Cangrelor for injection was supplied in 50 mg lyophilized single-use vials (The Medicines Company, Parsippany, N.J.). Each vial was reconstituted with 5 mL of sterile water for injection to yield a 10 mg/mL solution. The 5 mL contents of each vial was removed using a syringe and needle and transferred to a 50 mL bag of 0.9% sodium chloride injection, USP (B. Braun, Bethlehem, Pa.) yielding a diluted concentration of 1 mg/mL. Bivalirudin was prepared separately in 0.9% sodium chloride injection or 5% dextrose injection (Baxter Healthcare, Deerfield, Ill.) to a final concentration of 5 mg/mL.

5 mL samples of the cangrelor 1 mg/mL diluted solution were separately combined with 5 mL samples of the bivalirudin dilutions in colorless 15-mL borosilicate glass screw-cap culture tubes (Kimble, Division of Owens-Illinois, Toledo, Ohio) with polypropylene caps (Kimble, Division of Owens-Illinois) as described in Trissel L. A. et al., *Am J Hosp Pharm* 50:2359-63 (1993). Each of the sample solutions was passed through a 0.22-um filter (Millex-GV, Millipore Products, Bedford, Mass.) as it was introduced into the tube. Each combination was prepared in duplicate, reversing the order of drug addition between the two samples.

As controls, cangrelor 1 mg/mL in 0.9% sodium chloride injection and the bivalirudin solutions were each diluted with an equal volume of 0.9% sodium chloride injection and separately with 5% dextrose injection to a concentration of 0.5 mg/mL to simulate test sample preparations.

Incompatibility in the cangrelor-bivalirudin combinations was defined as any visible particulate matter, substantial haze or turbidity change from that in the controls, or a color change, microprecipitate formation, or gas evolution. All samples were examined visually with the unaided eye in normal laboratory fluorescent light. Combinations with no obvious visible incompatibility were examined further using a Tyndall beam (high-intensity monodirectional light source, Dolan-Jenner Industries, Woburn, Mass.) as described in Trissel L. A. et al., *Am J Hosp Pharm* 50:2359-63 (1993). Inspections were performed over the first 15 minutes after sample preparation and at intervals of one and four hours after sample preparation. The samples were stored at room temperature (approximately 23° C.).

The samples were also assessed immediately after preparation and at one and four hours after preparation using a color-correcting turbidimeter (Model 2100AN, Hach Company, Loveland, Colo.) as previously described in Trissel L. A. et al., Am J Hosp Pharm 49:1716-9 (1992); Trissel L. A. et al., Am J Hosp Pharm 50:300-4 (1993). Triplicate determinations were made on each of the samples. The particle content of the samples was quantified after four hours using a light obscuration particle sizer/counter (Model 9703, Hiac-Royco, Division of Pacific Scientific Company, Grants Pass, Oreg.) to determine particle content in the size range of 2.04 to 112 um (the validated detection limits of the particle sizer/counter) to verify the absence of unacceptable amounts of microparticulates. Triplicate determinations were again made using the light obscuration particle sizer/counter on these samples for particulate determinations. Physical instability was defined as visible particulate matter, haze, color change or a change (increase or decrease) in measured turbidity change of 0.5 nephelometric turbidity unit or more (Trissel L. A. et al., Am J Hosp Pharm 50:2359-63 (1993); Trissel L. A. et al., Am J Hosp Pharm 49:1716-9 (1992); Trissel L. A. et al., Am J Hosp Pharm 50:300-4 (1993)).

Cangrelor 1 mg/mL in 0.9% sodium chloride injection, USP, visually appeared in normal room light and when viewed using a Tyndall beam as a clear, colorless free-flowing liquid. The initial 1 mg/mL dilution was essentially without turbidity having a very low measured turbidity near 0.13 nephelometric turbidity units (NTU). When diluted to 0.5 mg/mL with an equal amount of 0.9% sodium chloride injection, USP, or 5% dextrose injection, USP, in a manner identical to mixing with each of the secondary test drugs, the measured turbidity level remained near 0.13 NTU.

The cangrelor dilution in sodium chloride 0.9% was found to be physically compatible with bivalirudin. The combinations exhibited no observable changes, such as visible precipitation or turbidity formation, microparticulate formation or increased measured haze, and they appeared visually to be very similar in clarity to the cangrelor solution diluted with an equal quantity of a simple aqueous solution as well as exhibiting similar measured turbidities.

All documents, books, manuals, papers, patents, published patent applications, guides, abstracts, and other references cited herein are incorporated by reference in their entirety. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A method of treating stent thrombosis in a subject in need thereof, comprising administering to the subject an effective amount of a pharmaceutical composition comprising cangrelor, thereby treating stent thrombosis in a subject, wherein the pharmaceutical composition is administered intravenously as bolus in a dose of about 30 µg/kg cangrelor followed by a continuous infusion and wherein stent thrombosis is induced by implantation of a bare metal stent or a drug eluting stent into the subject.

2. The method of claim 1, wherein the pharmaceutical composition further comprises bivalirudin.

3. A method of reducing mortality in a subject undergoing stent implantation, comprising parenterally administering to the subject an effective amount of a pharmaceutical composition comprising cangrelor and an effective amount of a pharmaceutical composition comprising bivalirudin, thereby reducing mortality in a subject undergoing stent implantation, wherein the pharmaceutical composition comprising cangrelor is administered intravenously as bolus in a dose of about 30 μg/kg cangrelor followed by a continuous infusion, and wherein a likelihood of mortality is reduced in comparison to a likelihood of mortality in a subject not receiving the pharmaceutical composition comprising cangrelor that is administered intravenously as bolus in a dose of about 30 μg/kg cangrelor followed by a continuous infusion.

4. The method of claim 3, wherein the cangrelor and the bivalirudin are in the same pharmaceutical composition.

5. A method of treating or preventing myocardial infarction in a subject in need thereof, comprising administering to the subject an effective amount of a pharmaceutical composition comprising cangrelor, thereby treating or preventing myocardial infarction in a subject, wherein the pharmaceutical composition is administered intravenously as bolus in a dose of about 30 μg/kg cangrelor followed by a continuous infusion.

6. The method of claim 5, wherein the pharmaceutical composition further comprises bivalirudin.

7. The method of claim 1, wherein stent thrombosis is intraprocedural stent thrombosis, acute stent thrombosis, sub-acute stent thrombosis, late stent thrombosis or very late stent thrombosis.

8. The method of claim 3, wherein stent implantation is implantation of a bare-metal stent or a drug-eluting stent into the subject.

9. The method of claim 3, wherein stent implantation is during percutaneous coronary intervention (PCI).

10. The method of claim 3, wherein the pharmaceutical composition comprising cangrelor is administered before stent implantation, during stent implantation, or a combination thereof.

11. The method of claim 3, wherein the pharmaceutical composition comprising bivalirudin is administered before stent implantation, during stent implantation, or a combination thereof.

12. The method of claim 3, wherein the pharmaceutical composition comprising cangrelor is administered to the subject prior to stent implantation and said administration is continued during the period of stent implantation.

13. The methods of claim 3 or 4, wherein mortality is reduced over a period of about one year after stent implantation.

14. The method of claim 1, 3, or 5, wherein the pharmaceutical composition comprises about 1 mg/mL cangrelor.

15. The method of claim 1, 3, or 5, wherein the pharmaceutical composition comprises about 5 mg/mL cangrelor.

16. The method of claim 2, 4, or 6, wherein the pharmaceutical composition comprises about 1 mg/mL cangrelor and about 1 mg/mL bivalirudin.

17. The method of claim 2, 4, or 6, wherein the pharmaceutical composition comprises about 1 mg/mL cangrelor and about 5 mg/mL bivalirudin.

18. The method of claim 2, 4, or 6, wherein the pharmaceutical composition comprises about 5 mg/mL cangrelor and about 1 mg/mL bivalirudin.

19. The method of claim 2, 4, or 6, wherein the pharmaceutical composition comprises about 5 mg/mL cangrelor and about 5 mg/mL bivalirudin.

20. The method of claim 12, wherein the continuous intravenous infusion is administered at about 4 μg/kg/min cangrelor.

21. The method of claim 3, wherein the pharmaceutical composition comprising bivalirudin is administered to the subject as an intravenous bolus, as a continuous intravenous infusion, or as an intravenous bolus followed by a continuous intravenous infusion prior to stent implantation and said administration is continued during the period of stent implantation.

22. The method of claim 21, wherein the intravenous bolus is administered in a dose of about 0.75 mg/kg bivalirudin.

23. The method of claim 21, wherein the continuous intravenous infusion is administered at about 1.75 mg/kg/h bivalirudin.

24. The method of claim 3, wherein the pharmaceutical composition comprising cangrelor and the pharmaceutical composition comprising bivalirudin are administered concurrently.

25. The method of claim 9, wherein the pharmaceutical composition comprising bivalirudin is administered periprocedurally to PCI.

26. A method of preventing stent thrombosis in a subject in need thereof, comprising administering to the subject an effective amount of a pharmaceutical composition comprising cangrelor, thereby preventing stent thrombosis in a subject, wherein the pharmaceutical composition is administered intravenously as bolus in a dose of about 30 μg/kg cangrelor followed by a continuous infusion, wherein preventing stent thrombosis is prevention during percutaneous coronary intervention or other vascular stent implantation.

27. The method of claim 3, wherein the pharmaceutical composition comprising cangrelor is administered after stent implantation.

* * * * *